US008304206B2

(12) United States Patent
Smith et al.

(10) Patent No.: US 8,304,206 B2
(45) Date of Patent: Nov. 6, 2012

(54) MASS SPECTROMETRY ASSAYS FOR IDENTIFYING COMPOUNDS THAT ACTIVATE DEACETYLASES

(75) Inventors: Jesse Smith, Watham, MA (US); Jill Milne, Brookline, MA (US); Amy Lynch, Boston, MA (US); David Carney, Derry, NH (US); Andre Iffland, Cambridge, MA (US); Olivier Boss, Boston, MA (US)

(73) Assignee: Sirtris Pharmaceuticals, Inc., Cambridge, MA (US)

( * ) Notice: Subject to any disclaimer, the term of this patent is extended or adjusted under 35 U.S.C. 154(b) by 332 days.

(21) Appl. No.: 12/085,839

(22) PCT Filed: Dec. 1, 2006

(86) PCT No.: PCT/US2006/046021
§ 371 (c)(1),
(2), (4) Date: Feb. 19, 2009

(87) PCT Pub. No.: WO2007/064902
PCT Pub. Date: Jun. 7, 2007

(65) Prior Publication Data
US 2009/0221020 A1 Sep. 3, 2009

Related U.S. Application Data

(60) Provisional application No. 60/741,783, filed on Dec. 2, 2005, provisional application No. 60/792,126, filed on Apr. 14, 2006, provisional application No. 60/859,371, filed on Nov. 15, 2006.

(51) Int. Cl.
*C12Q 1/34* (2006.01)
(52) U.S. Cl. .......................... 435/18; 435/375
(58) Field of Classification Search .................... 435/18, 435/375
See application file for complete search history.

(56) References Cited

U.S. PATENT DOCUMENTS

| 7,544,497 | B2 * | 6/2009 | Sinclair et al. ............... 435/183 |
|---|---|---|---|
| 2003/0082668 | A1 | 5/2003 | Tamai et al. |
| 2003/0107325 | A1 | 6/2003 | Birkhead |
| 2003/0149261 | A1 | 8/2003 | Schramm et al. |
| 2003/0199002 | A1 | 10/2003 | Hekimi et al. |
| 2003/0224469 | A1 | 12/2003 | Buchholz et al. |
| 2003/0224473 | A1 | 12/2003 | McCafferty |
| 2004/0005574 | A1 | 1/2004 | Guarente et al. |
| 2004/0028607 | A1 | 2/2004 | Verdin et al. |
| 2004/0091950 | A1 | 5/2004 | Ansorge et al. |
| 2004/0180905 | A1 | 9/2004 | Munchhof |
| 2005/0287597 | A1 | 12/2005 | Ott et al. |
| 2006/0014705 | A1 | 1/2006 | Howitz et al. |
| 2006/0084135 | A1 * | 4/2006 | Howitz et al. ................... 435/29 |
| 2007/0099830 | A1 | 5/2007 | Guarente et al. |
| 2008/0293081 | A1 | 11/2008 | Milne et al. |
| 2009/0143376 | A1 * | 6/2009 | Milburn et al. ............ 514/233.2 |
| 2009/0163476 | A1 * | 6/2009 | Milburn et al. ............... 514/218 |
| 2010/0168084 | A1 | 7/2010 | Huber et al. |
| 2010/0215632 | A1 * | 8/2010 | Boss et al. ................... 424/94.1 |

FOREIGN PATENT DOCUMENTS

| WO | WO-02/14543 | 2/2002 |
|---|---|---|
| WO | WO-03/066889 | 8/2003 |
| WO | WO-2006/094233 | 9/2006 |
| WO | WO 2006/094239 | 9/2006 |
| WO | WO2006094233 | 9/2006 |
| WO | WO-2006094235 A1 | 9/2006 |

OTHER PUBLICATIONS

Blander et al. "Sirt1 Shows No Substrate Specificity in Vitro" Journal of Biological Chemistrry 2005, 280P:11, 9780-9785.
Bonin et al. "Development of a Fluorescence Polarization Assay for Peptidyl-Trna Hydrolase," Analytical Biochemistry 306(1):8-16 (2002).
DeWitt et al. Proc. Natl. Acad. Sci. USA 90,6909, 1993.
Garsek and Denu "SIRT1 Top 40 Hits: Use of One-Bead, One-Compound Acetyl-Peptide Libraries and Quantum Dots to Probe Deacetylase Specificity" Biochemistry 2006, 45, 94-101.
Hoffmann et al., Nucleic Acids Res. 1999, 27, 2057-8.
Karas et al. Int. J. Mass Spectrom. Ion Processes 78:53, 1987.
Levine et al. "Measurement of Specific Protease Activity Utilizing Fluorescence Polarization," Analytical Biochemistry 247(1):83-88 (1997).
Marcotte, P.S. et al. "Fluorescence Assay of SIRT Protein Deacetylases Using an Acetylated Peptide Substrate and a Secondary Trypsin Reaction," Analytical Biochemistry 332(2004):90-99.
Milne et al. "Small molecule activators of SIRT1 as therapeutics for the treatment of type 2 diabetes," Nature v. 450:29;712-716 (2007).
Nikiforov et al. "Application of fluorescence polarization to enzyme assays and single nucleotide polymorphism genotyping: some recent developments," Current Topics in Medicinal Chemistry 6(3):201-212(2003).
Ozbal et al. (Assay and Drug Development Technologies, 2 (4), 2004).
Smith, C. M. "Quantification of Acetylation at Proximal Lysine Residues Using Isotopic Labeling and Tandem Mass Spectrometry," Methods 36:4 395-403, 2005.
Tanner et al., J. Biol. Chem, 1999, 274, 18157-18160.
Wegener et al. "Improved fluorogenic histone deacetylase assay for high-throughput-screening applications," Analytical Biochemistry 321(2):202-208 (2003).
Mohammed et al., Fluorescence polarization: an analytical tool for immunoassay and drug discovery. Combinatorial Chemistry and High Throughput Screening. vol. 2, No. 4 pp. 177-190 (1999).
Howitz, K., et al., "Small molecule activators of sirtuins extend *Saccharomyces cerevisiae* lifespan," Nature, 425:191-196 (2003).

(Continued)

*Primary Examiner* — Ralph Gitomer
(74) *Attorney, Agent, or Firm* — James T. Olesen; Jeffrey A. Sutton

(57) ABSTRACT

Provided are methods for determining the activity of proteins that modulate the acetylation state of a protein substrate. The methods may be used for determining both acetyltransferase activity and deacetylase activity. The methods utilize mass spectrometry for determining the acetylation state of a substrate peptide. The methods may also be used to identify compounds that modulate the activity of a protein having acetyltransferase or deacetylase activity. In some embodiments, a compound that modulates a deacetylase is an activator of the deacetylase.

15 Claims, 16 Drawing Sheets

OTHER PUBLICATIONS

Kim, J. Y., "Probing Lysine Acetylation with a Modification-Specific Marker Ion Using High-Performance Liquid Chromatography/Electrospray-Mass Spectrometry with Collision-Induced Dissociation," Analytical Chemistry, 74(21):5443-5449 (2002).

Pacholec, M., et al., "SRT1720, SRT2183, SRT1460, and Resveratrol are not Direct Activators of SIRT1," Journal of Biological Chemistry, 285(11):8340-8351 (2010).

Papers of the Week, "A Resveratrol Reversal," downloaded from www.jbc.org at Harvard Libraries, on Mar. 10, 2010.

Blum, C. A., et al., "SIRT1 Modulation as a Novel Approach to the Treatment of Diseases of Aging," J. Med. Chem., 54:417-432 (2011).

Dai, H., et al., "SIRT1 Activation by Small Molecules, Kinetic and Biophysical Evidence for Direct Interaction of Enzyme and Activator," Journal of Biological Chemistry, 285(43):32695-32703 (Oct. 22, 2010).

DeVane R et al: "A molecular dynamics method for calculating molecular volume changes appropriate for biomolecular simulation" Biophysical Journal 85(5): 2801-2807 (2003).

Huber, J. L., "SIRT1-independent mechanisms of the putative sirtuin enzyme activators SRT1720 and SRT2183," Future Med. Chem., 2(12):1751-1759 (2010).

Sterner et al. "Acetylation of histones and transcription-related factors" Microbiology and Molecular Biology Reviews. 64(2): 435-459 (2000).

Aherne et al., "Assays for the identification and evaluation of histone acetyltransferase inhibitors" Methods 26: 245-253 (2002).

Ait-Si-Ali et al., "A rapid and sensitive assay for histone acetyltransferase activity" Nucleic Acids Research (26)16: 3869-3870 (1998).

Bitterman et al, "Inhibition of Silencing and Accelerated Aging by Nicotinamide, a Putative Negative Regulator of Yeast Sir2 and Human SIRT1." The Journal of Biological Chemistry (277)47: 45099-45107 (2002).

Beher et al., "Resveratrol is not a Direct Activator of SIRT1 Enzyme Activity" Chem. Biol. Drug Des, 74: 619-624 (2009).

Borra et al., "Mechanism of Human SIRT1 Activation by Resveratrol", J. Biol. Chem. 280(17):17187-195 (2005).

Hoffmann et al. "Fluorescence-Labeled Octapeptides as Substrates for Histone Deacetylase" Bioconjug Chem. 12: 51-5 (2001).

Hoffmann et al. "Improvement and Validation of the Fluorescence-Based Histone Deacetylase Assay Using an Internal Standard" Arch. Pharm. Pharm. Med. Chem 334: 248-252 (2001).

Inoue and Fujimoto, "Histone deacetylase from calf thymus." Biochimica et Biophysica Acta 220:307-316 (1970).

Kaeberlein et al., "Substrate-specific Activation of Sirtuins by Resveratrol" The Journal of Biological Chemistry (280)17: 17038-17045 (2005).

Kim et al. "A Continuous, Nonradioactive Assay for Histone Acetyltransferases." Analytical Biochemistry 280:308-314 (2000).

Kumke, et al. "Hybridization of fluorescein-labeled DNA oligomers detected by fluorescence anisotropy with protein binding enhancement" Anal. Chem. 67:3945-3951 (1995).

Nare et al., "Development of a Scintillation Proximity Assay for Histone Deacetylase Using a Biotinylated Peptide Derived from Histone-H4." Analytical Biochemistry 267:390-396 (1999).

Pfister et al., "Opposing Effects of Sirtuins on Neuronal Survival: SIRT1-Mediated Neuroprotection is Independent of its Deacetylase Activity" PLOS One 3(12):1-8 (2008).

Bauer et al., "dSir2 and Dmp53 Interact to Mediate Aspects of CR-dependent Life Span Extension in D. Melanogaster," AGING, 1(1):1-11 (2009).

Burnett et al., "Absence of Effects of Sir2 Overexpression on Lifespan in C. elegans and Drosophila," Nature, 477:482-486 (2011).

Cantó et al., "Don't Write Sirtuins Off," Nature, 477:411 (2011).

Couzin-Frankel, "Aging Genes: The Sirtuin Story Unravels," Science, 334:1194-1198 (2011).

Fersht, Chapters 3 and 6 of "Enzyme Structure and Metabolism" W.H.Freeman & Co Ltd.

Ledford, "Much Ado About Ageing," Nature, 464:480-481 (2010).

Lombard et al., "A Valuable Background Check," Nature, 477:410 (2011).

Minor et al., "SRT17290 Improves Survival and Healthspan of Obese Mice," Scientific Reports, 48 pages (2011).

Pacholec et al., "SRT1720, SRT2183 and SRT1460 Do Not Activate Sirt1 with Native Substrates", FASEB Summer Research Conferences; NAD Metabolism and Signaling, Jun. 21-26, 2009.

Pacholec et al., "SRT1720, SRT2183, SRT1460, and Resveratrol are not Direct Activators of SIRT1", JBC Papers in Press, Manuscript M109.088682, Jan. 8, 2010.

Stünkel et al., "Sirtuin 1 (SIRT1): The Misunderstood HDAC," J. of Biomolecular Screening, 16(10); 1153-1169 (2011).

Timmers et al., "Calorie Restriction-like Effects of 30 Days of Resveratrol Supplementation on Energy Metabolism and Metabolic Profile in Obese Humans," Cell Metabolism, 14:612-622 (2011).

Tissenbaum et al. "Increased dosage of a sir-2 gene extens lifespan iin Caenorhabditis elegans," Nature, 410: 227-230 (2001).

Viswanathan & Guarente "Regulation of Caenorhabditis elegans Lifespan by Sir-2.1 Transgenes," Nature, 477:E1-E2 (2011).

Buck, et al. J. Leukocyte Biology, 75: 939-950 (2004).

Kaeberlein, et al. Aging Cell, 6: 415-416 (2007).

Porcu, et al. TRENDS in Pharmacological Sciences, 26(2): 94-103 (2005).

\* cited by examiner

MASS SPECTROMETRY ASSAYS FOR IDENTIFYING COMPOUNDS THAT ACTIVATE DEACETYLASES

RELATED APPLICATIONS

This application is a national stage filing under 35 U.S.C. §371 of International Application No. PCT/US2006/046021, filed Dec. 1, 2006, which claims the benefit of U.S. Provisional Application Nos. 60/741,783, filed Dec. 2, 2005, 60/792,126, filed Apr. 14, 2006, and 60/859,371, filed Nov. 15, 2006, which applications are hereby incorporated by reference in their entireties. International Application PCT/US2006/043503 was published under PCT Article 21(2) in English.

BACKGROUND

Acetylation and deacetylation of histone proteins, transcription factors, and related proteins play a major role in the control of cellular processes. In particular, the acetylation state of histones controls how tightly the histone proteins interact with DNA, and therefore how accessible the DNA is to transcription factors. Enzymes that add acetyl groups to histones or other proteins are called histone acetyltransferases (HATs). Enzymes that remove the acetyl groups fall into two families: the histone deacetylases (HDACs) and the Sir2 family of deacetylases. Currently there are eleven known members of the mammalian HDAC family (Gray and Ekstrom, Exper. Cell Res. 2001, 262, 75-83; Zhou, et al. Proc. Natl. Acad. Sci. USA 2001, 98, 10572-10577; Kao et al. J. Biol. Chem. 2002, 277, 187-193; Gao et al. J. Biol. Chem. 2002, 277, 25748-25755) and seven members of the Sir2 family (Gray and Ekstrom, Exper. Cell Res. 2001, 262, 75-83).

Histone acetyltransferases catalyze the transfer of an acetyl group from acetyl-CoA to the $\epsilon$-amino group of a lysine residue on the target protein. Many HAT enzymes have been characterized from eukaryotic organisms (Sterner and Berger, Microbiol. Mol. Biol. Rev. 2000, 64, 435-459). HDAC enzymes utilize a zinc ion at the active site of the protein to catalyze the removal of the acetyl group from acetyllysine in the form of acetate. Members of the Sir2 family of enzymes use NAD as a cofactor in the hydrolysis of acetyllysine.

The acetylation state of histone proteins plays a major role in gene expression and in cell-cycle control, and appears to play a role in certain forms of cancer. In particular, abnormal recruitment of histone deacetylases by corepressor proteins has been shown to promote the development of promyelocytic leukemia. In tumor cell lines, several studies have shown that treatment with HDAC inhibitors can lead to growth inhibition, growth arrest, terminal differentiation, and/or apoptosis. In vivo studies have demonstrated growth inhibition of tumors and a reduction in tumor metastasis as a result of treatment with HDAC inhibitors (Kramer et al. Trends Endocrinol. Metab. 2001, 12, 294-300).

Effective study of the enzymology and modulation of HATs, HDACs, and Sir2 enzymes depends on the availability of robust assays capable of being performed in a high-throughput manner. Several assay methodologies have been developed for these enzymes, with varying degrees of utility for inhibitor and activator screening.

Histone acetyltransferase assays are typically radioactivity-based. In these formats, acetyl-CoA radiolabeled on the acetyl group is reacted with a peptide corresponding to a histone amino acid sequence. Transfer of radiolabeled acetate to the peptide is quantified by binding of the peptide to affinity resin (Ait-Si-Ali et al. Nucleic Acids Res. 1998, 26, 3869-3870), phosphocellulose paper (Tanner et al. J. Biol. Chem. 1999, 274, 18157-18160), or scintillation microplates (Wynne Aherne et al. Methods 2002, 26, 245-53) and measurement of the associated radioactivity. In a non-radioactive coupled assay format, the free CoA formed in the acetyltransferase reaction serves as a substrate for $\alpha$-ketoglutarate dehydrogenase or pyruvate dehydrogenase. Formation of NADH serves as a measure of the rate of acetyltransferase activity (Kim et al. Anal. Biochem. 2000, 280, 308-314).

The most common deacetylase assay methodology involves labeling lysine groups in histone peptides with radiolabeled acetate. The deacetylase enzyme removes the acetyl group as acetate, which is subsequently isolated by extraction and quantified on the basis of its radioactivity (Inoue and Fujimoto, Biochim. Biophys. Acta 1970, 220, 307-316). In a variant of this approach, a scintillation proximity assay, peptides derivatized with radiolabeled acetyl groups are attached to a bead containing scintillant that emits light upon exposure to radiation. In this assay format, cleavage of the acetyl groups causes a decrease in the light emission from the scintillant (Nare, et al., Anal. Biochem. 1999, 267, 390-396). A non-radioactivity-based assay uses peptides containing an acetyllysine group and a fluorescent tag. Reactivity is measured by high-performance liquid chromatography, using the difference in retention time of the acetylated and non-acetylated peptides to isolate and quantify the reaction products (Hoffmann et al. Nucleic Acids Res. 1999, 27, 2057-8; Hoffmann et al. Bioconjug Chem. 2001, 12, 51-5; Hoffmann et al. Arch Pharm (Weinheim) 2001, 334, 248-52). A commercial assay uses a two-step detection protocol. In the first step, a peptide containing an acetyllysine is reacted with a deacetylase for a given period of time. Following this, the reaction is quenched and the exposed lysine is reacted with a developing agent that produces a fluorophore, and the amount of deacetylated lysine is quantified using the fluorescence of the product (Biomol, Plymouth Meeting, Pa., USA). More recently, a two-step, protease-coupled assay was reported, in which a peptide was designed containing a fluorescence resonance energy transfer (FRET) donor-quencher pair and an acetyllysine. After the deacetylase reaction has been allowed to run, the reaction is quenched and the amount of deacetylated peptide is quantified by reaction of the deacetylated peptide with a protease enzyme that cleaves specifically after lysine residues (Frey et al. Presented at 224th National Meeting of the American Chemical Society, Boston, Mass., August 2002; paper MEDI-121, Marcotte et al., Anal. Biochem., 332: 90 (2004)).

Features of the above assay formats limit their utility. Assays based on radioactivity tend to be costly, and require special handling precautions. Also, they are often difficult to perform in a high-throughput manner. Accordingly, improved assays for measuring the activity of acetyltransferases or deacetylases are needed.

SUMMARY

Provided herein are methods for identifying compounds that modulate the activity of an acetyltransferase or deacetylase.

In one aspect, the invention provides a method for determining the activity of a deacetylase, comprising: (a) contacting a peptide substrate pool with a deacetylase, wherein the members of said peptide substrate pool comprise at least one acetylated lysine residue; and (b) determining the level of acetylation of the peptide substrate pool, wherein a decrease in the level of acetylation of the peptide substrate pool is indicative of deacetylase activity.

In certain embodiments, the deacetylase may be, for example, a histone deacetylase (HDAC) or a sirtuin. In certain embodiments, the sirtuin may be, for example, a SIRT1 protein. In certain embodiments, the deacetylase may be a purified protein or provided as part of a mixture, such as a cell or tissue lysate.

In certain embodiments, the sequence of the peptide substrate may be derived from a histone, an HMG protein, p53, c-Myb, GATA-1, EKLF, MyoD, E2F, dTCF, or HIV Tat, or a fragment thereof.

In certain embodiments, the mass spectrometry may be electrospray ionization (ESI) mass spectrometry or matrix-assisted laser desorption/ionization (MALDI) mass spectrometry.

In one aspect, the invention provides, a method for identifying a compound that modulates a deacetylase, comprising: (a) contacting a peptide substrate pool with a deacetylase in the presence of a test compound, wherein the members of said peptide substrate pool comprise at least one acetylated lysine residue; and (b) determining the level of acetylation of the peptide substrate pool using mass spectrometry, wherein a change of the level of acetylation in the peptide substrate pool in the presence of the test compound as compared to a control is indicative of a compound that modulates a deacetylase.

In certain embodiments, the deacetylase may be, for example, a histone deacetylase (HDAC) or a sirtuin. In certain embodiments, the sirtuin may be, for example, a SIRT1 protein. In certain embodiments, the deacetylase may be a purified protein or provided as part of a mixture, such as a cell or tissue lysate.

In certain embodiments, the sequence of the peptide substrate may be derived from a histone, an HMG protein, p53, c-Myb, GATA-1, EKLF, MyoD, E2F, dTCF, or HIV Tat, or a fragment thereof.

In certain embodiments, a compound that increases the activity of the deacetylase is identified. In such embodiments, a decrease in the level of acetylation in the substrate pool in the presence of the test compound as compared to a control is indicative of a compound that increases the activity of the deacetylase.

In certain embodiments, a compound that inhibits the activity of the deacetylase is identified. In such embodiments, an increase in the level of acetylation in the substrate pool in the presence of the test compound as compared to a control is indicative of a compound that inhibits the activity of the deacetylase.

In certain embodiments, the concentration of peptide substrate in the peptide substrate pool may be below the Km of the deacetylase for the peptide substrate. In certain embodiments, the concentration of peptide substrate in the peptide substrate pool may be at least about 2-fold, 5-fold, 10-fold, 20-fold, 25-fold, or more, below the Km of the deacetylase for the peptide substrate.

In certain embodiments, a compound that activates a sirtuin to a greater extent than resveratrol may be identified. In certain embodiments, a compound that has sirtuin activating activity at least about, 2-fold, 5-fold, 10-fold, 20-fold, 50-fold, 100-fold, or more, greater than the sirtuin activating activity of resveratrol may be identified.

In certain embodiments, the mass spectrometry may be electrospray ionization (ESI) mass spectrometry or matrix-assisted laser desorption/ionization (MALDI) mass spectrometry.

In certain embodiments, the compound is a small molecule

In certain embodiments, the method for identifying a compound that modulates a deacetylase may further comprise one or more of the following: (i) preparing a quantity of the compound, or an analog thereof; (ii) conducting therapeutic profiling of the compound, or an analog thereof, for efficacy and toxicity in animals; (iii) formulating the compound, or analog thereof, in a pharmaceutical formulation; (iv) manufacturing a pharmaceutical preparation of a compound, or an analog thereof, having a suitable animal toxicity profile; (v) marketing a pharmaceutical preparation of a compound, or an analog thereof, having a suitable animal toxicity profile to healthcare providers.

In another aspect, the invention provides a method for determining the activity of an acetyltransferase, comprising: (a) contacting a peptide substrate pool with an acetyltransferase, wherein the members of said peptide substrate pool comprise at least one lysine residue; and (b) determining the level of acetylation of the peptide substrate pool, wherein an increase in the level of acetylation of the peptide substrate pool is indicative of acetyltransferase activity.

In certain embodiments, the acetyltransferase may be, for example, Gcn5 or p300/CBP. In certain embodiments, the acetyltransferase may be a purified protein or provided as part of a mixture, such as a cell or tissue lysate.

In certain embodiments, the sequence of the peptide substrate may be derived from a histone, an HMG protein, p53, c-Myb, GATA-1, EKLF, MyoD, E2F, dTCF, or HIV Tat, or a fragment thereof.

In certain embodiments, the mass spectrometry may be electrospray ionization (ESI) mass spectrometry or matrix-assisted laser desorption/ionization (MALDI) mass spectrometry.

In another aspect, the invention provides a method for identifying a compound that modulates an acetyltransferase, comprising: (a) contacting a peptide substrate pool with an acetyltransferase in the presence of a test compound, wherein the members of said peptide substrate pool comprise at least one lysine residue; and (b) determining the level of acetylation of the peptide substrate pool, wherein a change in the level of acetylation of the peptide substrate pool in the presence of the test compound as compared to a control is indicative of a compound that modulates the activity of the acetyltransferase.

In certain embodiments, the acetyltransferase may be, for example, Gcn5 or p300/CBP. In certain embodiments, the acetyltransferase may be a purified protein or provided as part of a mixture, such as a cell or tissue lysate.

In certain embodiments, the sequence of the peptide substrate may be derived from a histone, an HMG protein, p53, c-Myb, GATA-1, EKLF, MyoD, E2F, dTCF, or HIV Tat, or a fragment thereof.

In certain embodiments, a compound that inhibits the activity of the acetyltransferase is identified. In such embodiments, a decrease in the level of acetylation of the peptide substrate pool upon contact with the acetyltransferase in the presence of the test compound as compared to a control is indicative of a compound that inhibits the activity of the acetyltransferase.

In certain embodiments, a compound that increases the activity of the acetyltransferase is identified. In such embodiments, an increase in the level of acetylation of the peptide substrate pool upon contact with the acetyltransferase in the presence of the test compound as compared to a control is indicative of a compound that increases the activity of the acetyltransferase.

In certain embodiments, the mass spectrometry may be electrospray ionization (ESI) mass spectrometry or matrix-assisted laser desorption/ionization (MALDI) mass spectrometry.

In certain embodiments, the compound is a small molecule.

In certain embodiments, the method for identifying a compound that modulates an acetyltransferase may further comprise one or more of the following: (i) preparing a quantity of the compound, or an analog thereof; (ii) conducting therapeutic profiling of the compound, or an analog thereof, for efficacy and toxicity in animals; (iii) formulating the compound, or analog thereof, in a pharmaceutical formulation; (iv) manufacturing a pharmaceutical preparation of a compound, or an analog thereof, having a suitable animal toxicity profile; (v) marketing a pharmaceutical preparation of a compound, or an analog thereof, having a suitable animal toxicity profile to healthcare providers.

In another aspect, the invention provides a method for determining the activity of an enzyme that modulates acetylation of a peptide substrate, comprising: (a) contacting a peptide substrate pool with an enzyme that modulates acetylation; and (b) determining the level of acetylation of the peptide substrate pool, wherein a change in the level of acetylation of the peptide substrate pool is indicative of activity of the enzyme that modulates acetylation.

In certain embodiments, the enzyme that modulates acetylation may be a purified protein or provided as part of a mixture, such as a cell or tissue lysate.

In another aspect, the invention provides a method for identifying a compound that modulates the activity of an enzyme that modulates acetylation of a peptide substrate, comprising: (a) contacting a peptide substrate pool with an enzyme that modulates acetylation in the presence of a test compound; and (b) determining the level of acetylation of the peptide substrate pool, wherein a change in the level of acetylation of the peptide substrate pool in the presence of the test compound is indicative of a compound that modulates the activity of the enzyme that modulates acetylation.

In certain embodiments, the enzyme that modulates acetylation may be a purified protein or provided as part of a mixture, such as a cell or tissue lysate.

In another aspect, the invention provides a method for identifying a compound that activates a deacetylase, comprising: (a) contacting a peptide substrate pool with a deacetylase in the presence of a test compound, wherein members of said peptide substrate pool comprise at least one acetylated lysine residue, and (b) determining the level of acetylation of the peptide substrate pool using mass spectrometry, wherein a decrease in the level of acetylation of the peptide substrate pool in the presence of the test compound as compared to a control is indicative of a compound that activates a deacetylase.

In certain embodiments, the concentration of peptide substrate in the peptide substrate pool may be below the Km of the deacetylase for the peptide substrate. In certain embodiments, the concentration of peptide substrate in the peptide substrate pool may be at least 10 fold below the Km of the deacetylase for the peptide substrate.

In certain embodiments, the sequence of the peptide substrate may be derived from a histone, an HMG protein, p53, c-Myb, GATA-1, EKLF, MyoD, E2F, dTCF, or HIV Tat, or a fragment thereof.

In certain embodiments, the substrate peptide pool may comprise a single peptide species. In other embodiments, the substrate peptide pool may comprise a mixture of two or more peptides.

In certain embodiments, the deacetylase is a histone deacetylase (HDAC) or a sirtuin. In certain embodiments, a sirtuin may be, for example, a SIRT1 protein. certain embodiments, the deacetylase may be a purified protein or provided as part of a mixture, such as a cell or tissue lysate.

In certain embodiments, a compound that activates a sirtuin to a greater extent than resveratrol may be identified. In certain embodiments, a compound that has sirtuin activating activity at least 5-fold greater than the sirtuin activating activity of resveratrol may be identified.

In certain embodiments, the mass spectrometry may be electrospray ionization (ESI) mass spectrometry or matrix-assisted laser desorption/ionization (MALDI) mass spectrometry.

In certain embodiments, the compound is a small molecule.

In certain embodiments, the method for identifying a compound that modulates an acetyltransferase may further comprise one or more of the following: (i) preparing a quantity of the compound, or an analog thereof; (ii) conducting therapeutic profiling of the compound, or an analog thereof, for efficacy and toxicity in animals; (iii) formulating the compound, or analog thereof, in a pharmaceutical formulation; (iv) manufacturing a pharmaceutical preparation of a compound, or an analog thereof, having a suitable animal toxicity profile; (v) marketing a pharmaceutical preparation of a compound, or an analog thereof, having a suitable animal toxicity profile to healthcare providers.

In another aspect; the invention provides a method for identifying a compound that modulates the activity of a sirtuin protein, comprising (a) contacting a sample of cells with a putative sirtuin modulating compound, (b) determining the number of viable cells in the sample, and (c) determining the level of ATP in the sample, wherein a change in the average ATP level per viable cell in the presence of the putative sirtuin modulating compound as compared to a control is indicative of a compound that modulates the activity of the sirtuin.

In certain embodiments, the method for identifying a compound that modulates the activity of a sirtuin protein may further comprise assaying the compound for sirtuin modulating activity using an in vitro assay. Such in vitro assays may be conducted, for example, using mass spectrometry and/or fluorescent substrate to determine sirtuin activity. In certain embodiments, the in vitro assay may be carried out before contacting the sample of cells with the putative sirtuin modulating compound. In certain embodiments, the methods may further comprise comparing the results of the in vitro assay to the average ATP level per viable cell.

In certain embodiments, the sample of cells may comprise NCI-H358 and/or MCF7 cells.

In certain embodiments, the average ATP level per viable cell may be determined about 36-60 hours, or about 48 hours, after contacting the sample of cells with the putative sirtuin modulating compound.

In certain embodiments, the sirtuin may be, for example, a SIRT1 protein.

In certain embodiments, a compound that increases the activity of the sirtuin is identified. In such embodiments, an increase in the average ATP level per viable cell in the presence of the test compound as compared to a control is indicative of a compound that increases the activity of the sirtuin.

In certain embodiments, a compound that inhibits the activity of the sirtuin may be identified. In such embodiments, a decrease in the average ATP level per viable cell in the presence of the test compound as compared to a control is indicative of a compound that inhibits the activity of the sirtuin.

In certain embodiments, the compound is a small molecule.

In certain embodiments, the method for identifying a compound that modulates an acetyltransferase may further comprise one or more of the following: (i) preparing a quantity of the compound, or an analog thereof; (ii) conducting therapeutic profiling of the compound, or an analog thereof, for efficacy and toxicity in animals; (iii) formulating the compound, or analog thereof, in a pharmaceutical formulation; (iv) manufacturing a pharmaceutical preparation of a compound, or an analog thereof, having a suitable animal toxicity profile; (v) marketing a pharmaceutical preparation of a compound, or an analog thereof, having a suitable animal toxicity profile to healthcare providers.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

DETAILED DESCRIPTION

1. Definitions

Figure 1:
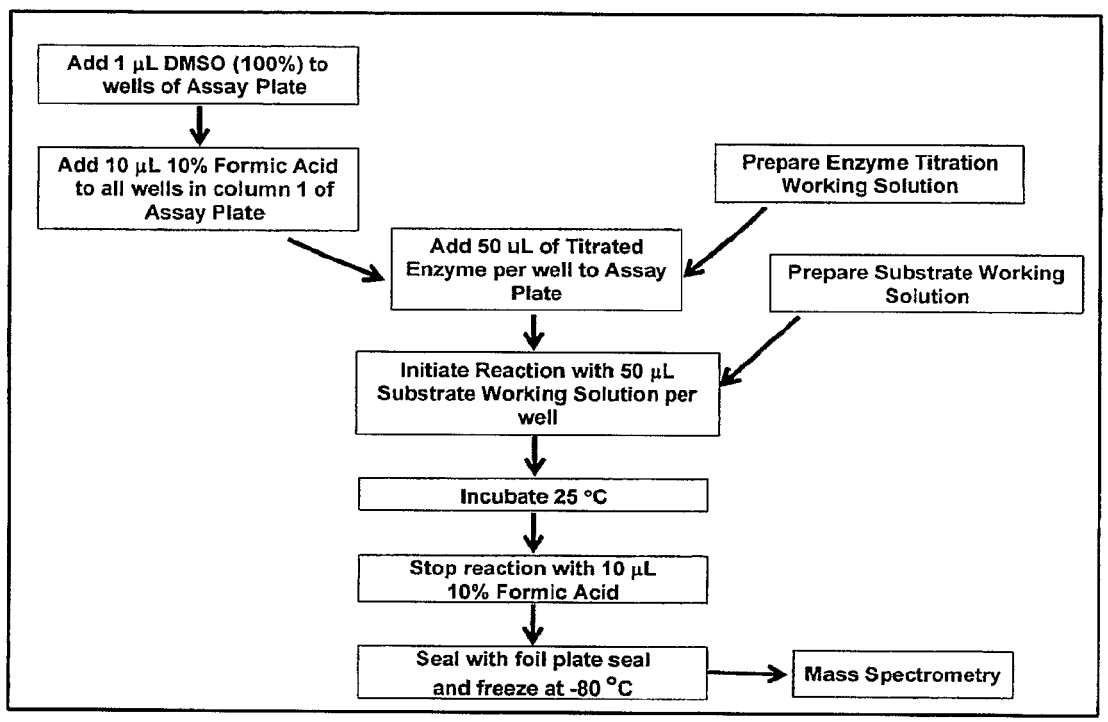
FIG. 1 shows a schematic outline of a SIRT1 titration mass spectrometry assay.

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The terms "comprise" and "comprising" are used in the inclusive, open sense, meaning that additional elements may be included.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, G. E. and R. H. Schirmer., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). One example of a set of amino acid groups defined in this manner include: (i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

The term "including" is used to mean "including but not limited to". "Including" and "including but not limited to" are used interchangeably.

The term "mammal" is known in the art, and exemplary mammals include humans, primates, livestock animals (including bovines, porcines, etc.), companion animals (e.g., canines, felines, etc.) and rodents (e.g., mice and rats).

The term "modulate", when used in reference to the activity of an acetyltransferase or deacetylase, refers to the up regulation (e.g., activation or stimulation), down regulation (e.g., inhibition or suppression), or other change in a quality of such acetyltransferase or deacetylase activity.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "substantially homologous" when used in connection with amino acid sequences, refers to sequences which are substantially identical to or similar in sequence with each other, giving rise to a homology of conformation and thus to retention, to a useful degree, of one or more biological (including immunological) activities. The term is not intended to imply a common evolution of the sequences.

The term "synthetic" is art-recognized and refers to production by in vitro chemical or enzymatic synthesis.

The term "therapeutic agent" is art-recognized and refers to any chemical moiety that is a biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art.

2. Mass Spectrometry Assays for Acetyltransferase/Deacetylase Activity

Provided herein are methods for determining the activity of acetyltransferase (acetylase) and deacetylase enzymes. The methods may involve, for example, contacting a substrate peptide pool with an acetyltransferase or deacetylase enzyme and determining the aceylation level of the substrate pool using mass spectrometry. In other embodiments, the invention provides methods for identifying compounds that modulate the activity of an acetyltransferase or deacetylase enzyme. The methods may involve, for example, contacting a substrate peptide pool with an acetyltransferase or deacetylase enzyme in the presence of a test compound and determining the acetylation level of the substrate pool using mass spectrometry.

In certain embodiments, the activity of an acetyltransferase (or acetylase) enzyme may be determined using the methods described herein. An acetylase is an enzyme that catalyzes a reaction by which an acetyl group ($CH_3CO—$) is transferred from a certain substance (for example, acetyl-CoA) to a peptide. Exemplary acetylases include, for example, members of the GNAT (Gcn5-realted N-acetyltransferase) superfamily, such as, for example, Hat1, Gcn5, PCAF, Elp3, and Hpa2;

members of the MYST (MOZ, Ybf2/Sas3, Sas2, and Tip60) family, such as, for example, Sas2, Sas3, Esa1, MOF, Tip60, MOZ, MORF, and HBO1; p300/CBP; nuclear receptor coactivators, such as, for example, SRC-1, ACTR, and TIF2; TAF$_{II}$1250; TFIIIC proteins, such as, for example, TFIIIC220, TFIIIC110 and TFIIIC90. Homologs, e.g., orthologs and paralogs, domains, fragments, variants and derivatives of the foregoing may also be used in accordance with the methods described herein. Acetylases and their substrates are reviewed, for example, in Sterner and Berger, Microbiol. Mol. Biol. Rev., 64: 453-459 (2000).

In other embodiments, the activity of a deacetylase enzyme may be determined using the methods described herein. A deacetylase is an enzyme that releases an acetyl group from an acetylated peptide. Exemplary deacetylase enzymes include, for example, histone deacetylases (HDACs) class I or II and HDACs class III (or sirtuins). Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Both Class I and II HDACs are inhibited by hydroxamic acid-based HDAC inhibitors, such as SAHA. Class III HDACs form a structurally distant class of NAD dependent enzymes that are related to the yeast SIR2 proteins and are not inhibited by hydroxamic acid-based HDAC inhibitors.

Exemplary HDAC class I or II enzymes that may be used in accordance with the methods described herein include, for example, human HDACs 1-8, e.g., HDAC-1 (GenBank Accession No. AAC50475 (nucleotide), U50079 (amino acid)), HDAC-2 (GenBank Accession No. AAC50814 (nucleotide), U31814 (amino acid)), HDAC-3 (GenBank Accession No. AAB88241 (nucleotide), U75697 (amino acid)), HDAC-4 (GenBank Accession No. BAA22957 (nucleotide), AB006626 (amino acid)), HDAC-5 (GenBank Accession No. BAA25526 (nucleotide), AB011172 (amino acid)), HDAC-6 (GenBank Accession No. AAD29048 (nucleotide), AJ011972 (amino acid)), HDAC-7 (GenBank Accession No. AAF63491.1 (nucleotide), AF239243 (amino acid)), or HDAC-8 (GenBank Accession No. AAF73076.1 (nucleotide), AF230097 (amino acid)), as well as homologs, e.g., orthologs and paralogs, domains, fragments, variants and derivatives of the foregoing.

In other embodiments, a deacetylase that may be used in accordance with the methods described herein is a sirtuin protein. A sirtuin protein refers to a member of the sirtuin deacetylase protein family, or preferably to the sir2 family, which include yeast Sir2 (GenBank Accession No. P53685), *C. elegans* Sir-2.1 (GenBank Accession No. NP_501912), and human SIRT1 (GenBank Accession No. NM_012238 and NP_036370 (or AF083106)) and SIRT2 (GenBank Accession No. NM_012237, NM_030593, NP_036369, NP_085096, and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273). Homologs, e.g., orthologs and paralogs, domains, fragments, variants and derivatives of the foregoing may also be used in accordance with the methods described herein.

In an exemplary embodiment, the methods described herein may be used to determine the activity of a SIRT1 protein. A SIRT1 protein refers to a member of the sir2 family of sirtuin deacetylases. In one embodiment, a SIRT1 protein includes yeast Sir2 (GenBank Accession No. P53685), *C. elegans* Sir-2.1 (GenBank Accession No. NP_501912), human SIRT1 (GenBank Accession No. NM_012238 or NP_036370 (or AF083106)), and human SIRT2 (GenBank Accession No. NM_012237, NM_030593, NP_036369, NP_085096, or AF083107) proteins, and equivalents and fragments thereof. In another embodiment, a SIRT1 protein includes a polypeptide comprising a sequence consisting of, or consisting essentially of, the amino acid sequence set forth in GenBank Accession Nos. NP_036370, NP_501912, NP_085096, NP_036369, or P53685. SIRT1 proteins include polypeptides comprising all or a portion of the amino acid sequence set forth in GenBank Accession Nos. NP_036370, NP_501912, NP_085096, NP_036369, or P53685; the amino acid sequence set forth in GenBank Accession Nos. NP_036370, NP_501912, NP_085096, NP_036369, or P53685 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. NP_036370, NP_501912, NP_085096, NP_036369, or P53685, and functional fragments thereof. SIRT1 proteins also include homologs (e.g., orthologs and paralogs), variants, or fragments, of GenBank Accession Nos. NP_036370, NP_501912, NP_085096, NP_036369, or P53685.

In one embodiment, the methods described herein may be used to determine the activity of a SIRT3 protein. A SIRT3 protein refers to a member of the sirtuin deacetylase protein family and/or to a homolog of a SIRT1 protein. In one embodiment, a SIRT3 protein includes human SIRT3 (GenBank Accession No. AAH01042, NP_036371, or NP_001017524) and mouse SIRT3 (GenBank Accession No. NP_071878) proteins, and equivalents and fragments thereof. In another embodiment, a SIRT3 protein includes a polypeptide comprising a sequence consisting of, or consisting essentially of, the amino acid sequence set forth in GenBank Accession Nos. AAH01042, NP_036371, NP_001017524, or NP_071878. SIRT3 proteins include polypeptides comprising all or a portion of the amino acid sequence set forth in GenBank Accession AAH01042, NP_036371, NP_001017524, or NP_071878; the amino acid sequence set forth in GenBank Accession Nos. AAH01042, NP_036371, NP_001017524, or NP_071878 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. AAH01042, NP_036371, NP_001017524, or NP_071878, and functional fragments thereof. SIRT3 proteins also include homologs (e.g., orthologs and paralogs), variants, or fragments, of GenBank Accession Nos. AAH01042, NP_036371, NP_001017524, or NP_071878.

In another embodiment, a biologically active portion of a sirtuin may be used in accordance with the methods described herein. A biologically active portion of a sirtuin refers to a portion of a sirtuin protein having a biological activity, such as the ability to deacetylate. Biologically active portions of sirtuins may comprise the core domain of a sirtuin. Biologically active portions of SIRT1 having GenBank Accession No. NP_036370 that encompass the NAD+ binding domain and the substrate binding domain, for example, may include without limitation, amino acids 62-293 of GenBank Accession No. NP_036370, which are encoded by nucleotides 237 to 932 of GenBank Accession No. NM_012238. Therefore, this region is sometimes referred to as the core domain. Other biologically active portions of SIRT1, also sometimes referred to as core domains, include about amino acids 261 to 447 of GenBank Accession No. NP_036370, which are encoded by nucleotides 834 to 1394 of GenBank Accession No. NM_012238; about amino acids 242 to 493 of GenBank Accession No. NP_036370, which are encoded by nucleotides 777 to 1532 of GenBank Accession No. NM_012238; or about amino acids 254 to 495 of GenBank Accession No. NP_036370, which are encoded by nucleotides 813 to 1538 of GenBank Accession No. NM_012238. In another embodiment, a biologically active portion of a sirtuin may be a fragment of a SIRT3 protein that is produced by cleavage with a mitochondrial matrix processing peptidase (MPP) and/or a mitochondrial intermediate peptidase (MIP).

Acetyltransferase and deacetylase enzymes that may be used in accordance with the methods described herein may be endogenous proteins, recombinant proteins, purified proteins, or proteins present in a mixture, such as a cell or tissue lysate. In certain embodiments, suitable enzymes for use in accordance with the methods described herein may be purchased commercially or purified using standard procedures. For example, human SIRT1 (Catalog #SE-239), human SIRT2 (Catalog #SE-251) and human SIRT3 (Catalog #SE-270) may be purchased from Biomol International (Plymouth Meeting, Pa.). Methods for expression and purification of human SIRT1 and human SIRT3 are described, for example, in PCT Publication No. WO 2006/094239. In other embodiments, suitable enzymes for use in accordance with the methods described herein may be provided as part of a mixture, such as, for example, a cell or tissue lysate or fractionated lysate. Suitable lysates include raw lysates including all components of the cell or tissue or lysates from which one or more components have been removed, such as, for example, nucleic acids, insoluble materials, membrane materials, etc. The lysate may be obtained from a variety of sources such as a blood cell sample, tissue sample, cell culture, etc.

A wide variety of peptide substrates may be used in accordance with the methods described herein. When determining the activity of an acetyltransferase, the peptide substrate utilized in the reaction comprises at least one non-acetylated lysine residue. When determining the activity of a deacetylase, the peptide substrate utilized in the reaction comprises at least one acetylated lysine residue.

In certain embodiments, the sequence of the peptide substrate may be obtained, or derived, from a protein that may be acetylated or deacetylated by an acetyltransferase or deacetylase, respectively. Exemplary substrates for acetyltransferases and deacetylases include, for example, histones (e.g., H1, H2, H2A, H2B, H3 and H4), nonhistone chromatin proteins (e.g., HMG1, HMG2, Yeast Sin1, HMG14, HMG17, and HMG I(Y)), transcriptional activators (e.g., p53, c-Myb, GATA-1, EKLF, MyoD, E2F, dTCF, and HIV Tat), nuclear receptor coactivators (e.g., ACTR, SRC-1, TIF2), general transcription factors (e.g., TFIIE and TFIIF), importin-α7, Rch1, and α-tubulin. Substrate peptides used in accordance with the methods described herein may comprise an entire substrate protein or a portion thereof containing at least one lysine residue. In certain embodiments, it may be desirable to modify the sequence of a substrate protein, or a fragment thereof, to add, remove and/or change the location of one or more lysine residues. For example, it may be desirable to have a substrate peptide that contains one or more lysine residues located only in desired locations within the substrate peptide, e.g., toward the center of the substrate, toward an end of the substrate (e.g., N-terminal or C-terminal end), having multiple lysine residues clustered together, having lysine residues spread across the peptide, etc. In certain embodiments, it may be desirable to have a substrate peptide that contains only a single lysine residue. One or more lysine residues may be removed from a peptide substrate sequence by replacing the amino acid residue with a different amino acid residue or by deleting the amino acid residue from the sequence without substitution of a different amino acid. In certain embodiments, one or more lysine residues may be replaced using a conservative amino acid substitution.

In exemplary embodiments, the invention provides a method for identifying compounds that activate a sirtuin protein, such as, for example, a SIRT1 protein. In such embodiments, the methods utilize a substrate peptide that is a sirtuin activatable substrate peptide. A sirtuin activatable substrate peptide is a peptide substrate that is suitable for use in a mass spectrometry based assay to identify activators of sirtuin activity. A sirtuin activatable substrate peptide may be identified using a variety of sirtuin assays, including for example, the mass spectrometry assay described herein and the other sirtuin activity assays described herein below. Exemplary sirtuin activatable substrate peptides are provided herein in Tables 1 and 2 below. In certain embodiments, the sequence of a sirtuin activatable substrate peptide is derived from a known sirtuin substrate, such as, for example, an HMG protein, p53, c-Myb, GATA-1, EKLF, MyoD, E2F, dTCF, or HIV Tat, or a fragment thereof. In certain embodiments, a sirtuin activatable substrate peptide may be from about 5-100, about 10-100, about 10-75, about 10-50, about 20-100, about 20-75, about 20-50, about 20-30, or about 20-25 amino acids in length. In certain embodiments, a sirtuin activatable substrate peptide comprises at least one hydrophobic region. In certain embodiments, a hydrophobic region may be located at or near one or both ends of the sirtuin activatable substrate peptide, e.g., the N-terminal and/or C-terminal ends. A hydrophobic region may be naturally occurring in the sequence of the sirtuin activatable substrate peptide, e.g., at least a portion of a sirtuin substrate protein comprising a hydrophobic region may be used as the substrate peptide. In the alternative, or in addition, a hydrophobic region may be added to a sirtuin activatable substrate peptide. For example, a hydrophobic region may be added to a substrate peptide by modifying the sequence of the peptide to increase the number of hydrophobic amino acid residues in a desired region, e.g., by adding 1, 2, 3, 4, 5, 6, 7, 8, 9, 10, or more, hydrophobic amino acid residues to a peptide either by the addition of new amino acid residues or by the replacement of existing non-hydrophobic (or less hydrophobic) amino acid residues with hydrophobic (or more strongly hydrophobic) amino acid residues. In certain embodiments, a hydrophobic region may be region of about 2, 3, 4, 5, 6, 7, 8, 9, 10 or more hydrophobic amino acid residues in a contiguous or substantially contiguous stretch within the peptide. Hydrophobic amino acid residues include alanine, phenylalanine, glycine, isoleucine, leucine, methionine, proline, valine, and tryptophan. In exemplary embodiments, hydrophobic regions comprise one or more tryptophan, alanine and/or phenylalanine amino acid residues. Alternatively, a hydrophobic region may be added to a substrate peptide by chemically modifying the peptide to increase its hydrophobicity. For example, a hydrophobic region may be introduced into a peptide by covalently attaching a hydrophobic chemical moiety to the peptide. Examples of chemical moieties include, for example, fluorophores, such as, AF 350, AF 430, AF 488, AF 532, AF 546, AF 568, AF 594, AF 633, AF 647, AF 660, AF 680, dintrophenyl, AMCA, Cascade Blue, Marina Blue, Fluorescein/FITC, Oregon Green 488, Rhodamine Green, BODIPY FL, BODIPY TMR, BODIPY TR, Oregon Green 514, Rhodamine Red, Tetramethylrhodamine, Texas Red, BODIIPY 630/650, BODTPY 650/665, QSY 7, Fluor X, Cy2 bis, Cy3 mono, Cy3.5 mono, Cy5 mono, Cy5.5 mono, Cy7 mono, DEAC, R6G, TAMRA, and MR121. Methods for covalently modifying a peptide with a chemical moiety such as a fluorophore are known in the art, and thus, can be conducted according to conventional methods. In exemplary embodiments, the hydrophobic chemical moiety may be covalently linked or conjugated to the peptide so as not to interfere with acetylation or deacetylation of the lysine residue(s).

Substrate peptides that may be used in accordance with the methods described herein can be synthesized according to conventional methods. The substrate peptides may include naturally occurring peptides, peptides prepared by genetic recombination techniques, and synthetic peptides. The peptides may be fused with other peptides (for example, glutathione-S-transferase, HA tag, FLAG tag, etc.) for convenience of purification, etc. Further, the peptide may comprise structural units other than amino acids so long as it serves as a substrate for a deacetylase or acetyltransferase. Typically, the synthesis of a peptide is achieved by adding amino acids, residue by residue, from the carboxyl terminus of the amino acid sequence of interest. Further, some of the peptide fragments synthesized in that way may be linked together to from a larger peptide molecule. For measuring deacetylase activity, the substrate peptide needs to be acetylated before the reaction is conducted. An exemplary method of amino acid acetylation includes acetylation of amino acids, whose α-amino groups and side-chain amino groups are blocked with protecting groups, with acetic anhydride, N-hydroxysuccinimide acetate, or similar reagents. These acetylated amino acids are then used to synthesize peptides comprising acetylated lysine residues, for example, using the solid-phase method. Generally, acetylated peptides can be synthesized using a peptide synthesizer according to the Fmoc method. For example, commercial suppliers, who provide custom peptide synthesis services, can synthesize peptides having specified amino acid sequences comprising residues acetylated at predetermined positions.

Exemplary peptide substrates for Sirt1, Sirt2 and Sirt3 deacetylases that may be used in accordance with the methods described herein are shown below in Tables 1 and 2.

TABLE 1

Sirt1, Sirt2 and Sirt3 peptide substrates having covalently attached chemical moieties.

| Enzyme/Basis for Peptide sequence | Sequence | SEQ ID NO |
|---|---|---|
| Sirt1/p53 | Ac-EEKGQSTSSHS-K(Ac)-Nle-STEG-K(MR121)-EE-NH$_2$ | SEQ ID NO: 1 |
| Sirt1/p53 | Ac-EEKGQSTSSHS-K(Ac)-Nle-STEG-K(5-TMR)-EE-NH$_2$ | SEQ ID NO: 2 |
| Sirt1/PGC1alpha | TNPAIV-K(Ac)-TENS-K(MR121)-NH$_2$ | SEQ ID NO: 3 |
| Sirt1/PGC1alpha | TNPAIV-K(Ac)-TENS-K(5-TMR)-NH$_2$ | SEQ ID NO: 4 |
| Sirt1/PGC1alpha | QHLQA-K(Ac)-PTTLS-K(MR121)-NH$_2$ | SEQ ID NO: 5 |
| Sirt1/PGC1alpha | QHLQA-K(Ac)-PTTLS-K(5-TMR)-NH$_2$ | SEQ ID NO: 6 |
| Sirt2/alpha-Tubulin | MPSD-K(Ac)-TIGG-K(MR121)-NH$_2$ | SEQ ID NO: 7 |
| Sirt2/alpha-Tubulin | MPSD-K(Ac)-TIGG-K(5-TMR)-NH$_2$ | SEQ ID NO: 8 |
| Sirt2/alpha-Tubulin | Nle-PSD-K(Ac)-TIGG-K(MR121)-NH$_2$ | SEQ ID NO: 9 |
| Sirt2/alpha-Tubulin | Nle-PSD-K(Ac)-TIGG-K(5-TMR)-NH$_2$ | SEQ ID NO: 10 |
| Sirt2/alpha-Tubulin | GQ-Nle-PSD-K(Ac)-TIGG-K(MR121)-NH$_2$ | SEQ ID NO: 11 |
| Sirt2/alpha-Tubulin | GQ-Nle-PSD-K(Ac)-TIGG-K(5-TMR)-NH$_2$ | SEQ ID NO: 12 |
| Sirt3/Acetyl CoA Synthase 2 | SG-K(Ac)-IM-K(MR121)-NH$_2$ | SEQ ID NO: 13 |
| Sirt3/Acetyl CoA Synthase 2 | SG-K(Ac)-IM-K(5-TMR)-NH$_2$ | SEQ ID NO: 14 |
| Sirt3/Acetyl CoA Synthase 2 | TSSG-K(Ac)-I-Nle-S-K(MR121)-NH$_2$ | SEQ ID NO: 15 |

TABLE 1-continued

Sirt1, Sirt2 and Sirt3 peptide substrates having covalently attached chemical moieties.

| Enzyme/Basis for Peptide sequence | Sequence | SEQ ID NO |
|---|---|---|
| Sirt3/Acetyl CoA Synthase 2 | TSSG-K(Ac)-I-Nle-S-K(5-TMR)-NH$_2$ | SEQ ID NO: 16 |
| Sirt3/Acetyl CoA Synthase 2 | PSTSSG-K(Ac)-I-Nle-SS-K(MR121)-NH$_2$ | SEQ ID NO: 17 |
| Sirt3/Acetyl CoA Synthase 2 | PSTSSG-K(Ac)-I-Nle-SS-K(5-TMR)-NH$_2$ | SEQ ID NO: 18 |
| Sirt3/Histone H4 | SGSG-K(Ac)-GGS-K(MR121)-NH$_2$ | SEQ ID NO: 19 |
| Sirt3/Histone H4 | SGSG-K(Ac)-GGS-K(5-TMR)-NH$_2$ | SEQ ID NO: 20 |
| Sirt3/Histone H4 | GSGGA-K(Ac)-SHS-K(MR121)-NH$_2$ | SEQ ID NO: 21 |
| Sirt3/Histone H4 | GSGGA-K(Ac)-SHS-K(5-TMR)-NH$_2$ | SEQ ID NO: 22 |
| Sirt3/Histone H4 | GASSHS-K(Ac)-VL-K(MR121)-NH$_2$ | SEQ ID NO: 23 |
| Sirt3/Histone H4 | GASSHS-K(Ac)-VL-K(5-TMR)-NH$_2$ | SEQ ID NO: 24 |

TABLE 2

Sirtuin peptide substrates having hydrophobic amino acid regions.

| Enzyme/Basis for Peptide sequence | Sequence | SEQ ID NO |
|---|---|---|
| p53 | Ac-EEKGQSTSSHS-K(Ac)-Nle-STEGKWEE-NH$_2$ | SEQ ID NO: 25 |
| p53 | Ac-EEKGQSTSSHS-K(Ac)-Nle-STEGKWAWEE-NH$_2$ | SEQ ID NO: 26 |
| p53 | Ac-EEKGQSTSSHS-K(Ac)-Nle-STEGKWWFEE-NH$_2$ | SEQ ID NO: 27 |
| p53 | Ac-EEKGQSTSSHS-K(Ac)-Nle-STEGKWWWEE-NH$_2$ | SEQ ID NO: 28 |
| p53 | Ac-EEKGQSTSSHS-K(Ac)-Nle-STEGWEE-NH$_2$ | SEQ ID NO: 29 |
| p53 | Ac-EEKGQSTSSHS-K(Ac)-Nle-STEGWAWEE-NH$_2$ | SEQ ID NO: 30 |
| p53 | Ac-EEKGQSTSSHS-K(Ac)-Nle-STEGWWFEE-NH$_2$ | SEQ ID NO: 31 |
| p53 | Ac-EEKGQSTSSHS-K(Ac)-Nle-STEGWWWEE-NH$_2$ | SEQ ID NO: 32 |
| p53 | Ac-EEKGQSTSSHS-K(Ac)-Nle-STEGKWWWWEE-NH$_2$ | SEQ ID NO: 33 |

In certain embodiments, the invention provides a peptide substrate for use in determining the activity of an acetyltransferase or deacetylase using mass spectrometry wherein the substrate comprises one or more of SEQ ID NOs: 1-35.

In certain embodiments, the methods described herein are carried out under conditions which permit acetylation or deacetylation of the peptide substrate by an acetyltransferase or deacetylase, respectively.

In certain embodiments, the substrate peptide pool comprises a plurality of copies of one or more substrate peptides. In an exemplary embodiment, a substrate peptide pool comprises a plurality of copies of the same peptide substrate. Such peptide substrate pools may comprise the peptide substrate free floating in solution or attached to a solid surface such as a plate, bead, filter, etc. Combinations of free floating and anchored peptide substrate molecules may also be used in accordance with the methods described herein.

In certain embodiments, the methods described herein may be carried out in a single reaction vessel without the need to remove reagents from the reaction mixture (e.g., a homogenous assay). In various embodiments, the components of the reactions described herein may be added sequentially or simultaneously.

In certain embodiments, the invention provides a method for identifying a compound that modulates the activity of an acetyltransferase or deacetylase. The methods may involve comparing the activity of an acetyltransferase or deacetylase in the presence of a test compound to the activity of the acetyltransferase or deacetylase in a control reaction. The control reaction may simply be a duplicate reaction in which the test compound is not included. Alternatively, the control reaction may be a duplicate reaction in the presence of a compound having a known effect on the acetyltransferase or deacetylase activity (e.g., an activator, an inhibitor, or a compound having no effect on enzyme activity).

Due to the flexibility available in designing peptide substrates for the mass spectrometry based methods described herein, it is possible to optimize the peptide substrates to provide a low apparent Km thus permitting a lower concentration of substrate to be used in association with the methods.

Table 3 shown below provides the Km values for a sirtuin peptide substrate provided in accordance with the methods described herein in comparison to the Km values of several published or commercially available sirtuin assays. Accordingly, in certain embodiments, the substrate peptides for use in accordance with the methods described herein may be optimized to provide a low apparent Km.

TABLE 3

Km comparisons for various sirtuin assays.

| Reference | Assay | Enzyme | Peptide substrate (*FL with fluorescent label) | Peptide Km (uM) | NAD Km (uM) |
|---|---|---|---|---|---|
| Biomol (Fluor de Lys)[1] | Fluorescent | Sirt1 | p53 (aa 379-382) *FL | 64 | 558 |
|  | Fluorescent | Sirt2 | p53 (aa 317-320) *FL | 186 | 547 |
|  | Fluorescent | Sirt3 | p53 (aa 317-320) *FL | 32 | 2034 |
| [2]Kaeberlein et al. | Nicotinamide release | Sirt1 | p53 (aa 368-386) no FL | 10.3 | 132.5 |
|  | Nicotinamide release | Sirt1 | p53 (aa 368-386) *FL | 87.6 | 192 |
| [3]Marcotte et al. | FRET | Sirt1 | p53 20 mer (aa 372-387) *FL | ND | 90 |
|  | FRET | Sirt2 | p53 20 mer (aa 372-387) *FL | ND | 42 |
| [4]McDonagh et al. | Nicotinamide release | Sirt1 | p53 19 mer (aa 368-386) no FL | 10.3 | 133 |
| Present invention | Mass Spectrometry | Sirt1 | SEQ ID NO: 34 | 11.6 | 464 |

[1]Biomol (Fluor de Lys) as described in product literature for SIRT1 Fluorimetric Drug Discovery Kit (AK-555), SIRT2 Fluorimetric Drug Discovery Kit (AK-556), SIRT3 Fluorimetric Drug Discovery Kit (AK-557) (Biomol International, Plymouth Meeting, PA);
[2]Kaeberlein et al., JBC, 280 (17), 17038, 2005;
[3]Marcotte et al., Anal. Biochem., 332, 90, 2004;
[4]McDonagh et al., Methods, 36, 346, 2005.

The methods described herein utilize mass spectrometry for determining the level of acetylated and/or deacetylated substrate in a reaction. Mass spectrometry (or simply MS) encompasses any spectrometric technique or process in which molecules are ionized and separated and/or analyzed based on their respective molecular weights. Thus, mass spectrometry and MS encompass any type of ionization method, including without limitation electrospray ionization (ESI), atmospheric-pressure chemical ionization (APCI) and other forms of atmospheric pressure ionization (API), and laser irradiation. Mass spectrometers may be combined with separation methods such as gas chromatography (GC) and liquid chromatography (LC). GC or LC separates the components in a mixture, and the components are then individually introduced into the mass spectrometer; such techniques are generally called GC/MS and LC/MS, respectively. MS/MS is an analogous technique where the first-stage separation device is another mass spectrometer. In LC/MS/MS, the separation methods comprise liquid chromatography and MS. Any combination (e.g., GC/MS/MS, GC/LC/MS, GC/LC/MS/MS, etc.) of methods can be used to practice the methods described herein. In such combinations, MS can refer to any form of mass spectrometry; by way of non-limiting example, LC/MS encompasses LC/ESI MS and LC/MALDI-TOF MS. Thus, mass spectrometry and MS include without limitation APCI MS; ESI MS; GC MS; MALDI-TOF MS; LC/MS combinations; LC/MS/MS combinations; MS/MS combinations; etc. Other examples of MS include, for example, MALDI-TOF-TOF MS, MALDI Quadrupole-time-of-flight (Q-TOF) MS, electrospray ionization (ESI)-TOF MS, ESI-Q-TOF, ESI-TOF-TOF, ESI-ion trap MS, ESI Triple quadrupole MS, ESI Fourier Transform Mass Spectrometry (FTMS), MALDI-FTMS, MALDI-Ion Trap-TOF, ESI-Ion Trap TOF, surface-enhanced laser desorption/ionization (SELDI), MS/MS/MS, ESI-MS/MS, quadrupole time-of-flight mass spectrometer QqTOF MS, MALDI-QqTOFMS, ESI-QqTOF MS, and chip capillary electrophoresis (chip-CE)-QqTOF MS, etc.

It is often necessary to prepare samples comprising an analyte of interest for MS. Such preparations include without limitation purification and/or buffer exchange. Any appropriate method, or combination of methods, can be used to prepare samples for MS. One type of MS preparative method is liquid chromatography (LC), including without limitation HPLC and RP-HPLC.

High-pressure liquid chromatography (HPLC) is a separative and quantitative analytical tool that is generally robust, reliable and flexible. Reverse-phase (RP) is a commonly used stationary phase that is characterized by alkyl chains of specific length immobilized to a silica bead support. RP-HPLC is suitable for the separation and analysis of various types of compounds including without limitation biomolecules, (e.g., glycoconjugates, proteins, peptides, and nucleic acids, and, with mobile phase supplements, oligonucleotides). One of the most important reasons that RP-HPLC has been the technique of choice amongst all HPLC techniques is its compatibility with electrospray ionization (ESI). During ESI, liquid samples can be introduced into a mass spectrometer by a process that creates multiple charged ions (Wilm et al., Anal. Chem. 68:1, 1996). However, multiple ions can result in complex spectra and reduced sensitivity.

In HPLC, peptides and proteins are injected into a column, typically silica based C18. An aqueous buffer is used to elute the salts, while the peptides and proteins are eluted with a mixture of aqueous solvent (water) and organic solvent (acetonitrile, methanol, propanol). The aqueous phase is generally HPLC grade water with 0.1% acid and the organic solvent phase is generally an HPLC grade acetonitrile or methanol with 0.1% acid. The acid is used to improve the chromatographic peak shape and to provide a source of protons in reverse phase LC/MS. The acids most commonly used are formic acid, trifluoroacetic acid, and acetic acid. In RP HPLC, compounds are separated based on their hydrophobic character. With an LC system coupled to the mass spectrometer through an ESI source and the ability to perform data-dependant scanning, it is now possible in at least some instances to distinguish proteins in complex mixtures containing more than 50 components without first purifying each protein to homogeneity. Where the complexity of the mixture is extreme, it is possible to couple ion exchange chromatography and RP-HPLC in tandem to identify proteins from mixtures containing in excess of 1,000 proteins.

A particular type of MS technique, matrix-assisted laser desorption time-of-flight mass spectrometry (MALDI-TOF MS) (Karas et al., Int. J. Mass Spectrom. Ion Processes 78:53, 1987), has received prominence in analysis of biological polymers for its desirable characteristics, such as relative ease of sample preparation, predominance of singly charged ions in mass spectra, sensitivity and high speed. MALDI-TOF MS is a technique in which a UV-light absorbing matrix and a molecule of interest (analyte) are mixed and co-precipitated, thus forming analyte:matrix crystals. The crystals are irradiated by a nanosecond laser pulse. Most of the laser energy is absorbed by the matrix, which prevents unwanted fragmentation of the biomolecule. Nevertheless, matrix molecules transfer their energy to analyte molecules, causing them to vaporize and ionize. The ionized molecules are accelerated in an electric field and enter the flight tube. During their flight in this tube, different molecules are separated according to their mass to charge (m/z) ratio and reach the detector at different times. Each molecule yields a distinct signal. The method, may be used for detection and characterization of biomolecules, such as proteins, peptides, oligosaccharides and oligonucleotides, with molecular masses between about 400 and about 500,000 Da, or higher. MALDI-MS is a sensitive technique that allows the detection of low ($10^{-15}$ to $10^{-18}$ mole) quantities of analyte in a sample.

Electrospray ionization may be used for both very large and small molecules. The electrospray process produces multiply charged analytes, making it somewhat easier to detect larger analytes such as proteins. Also, small molecules can be measured readily in the absence of matrix. The MALDI process requires a matrix, which may make it more difficult to analyze small molecules, for example, with molecular weights of less than about 700 daltons.

With certain mass spectrometers, for example, MALDI-TOF, sensitivity decreases as the molecular weight of a molecule increases. For example, the detection sensitivity of molecules with molecular weights in the range of about 10,000 daltons may be an order of magnitude or more lower than detection sensitivity of molecules with molecular weights in the range of about 1,000 daltons. Use and detection of a coding moiety and/or labels with a different, for example lower, molecular weight than the analyte can therefore enhance the sensitivity of the assay. Sensitivity can also be increased by using a coding moiety and/or that is very amenable to ionization.

In electrospray mass spectrometry, sample introduction into a mass spectrometer such as a quadropole, an ion trap, a TOF, a FTICR, or a tandem mass spectrometer, the higher molecular weight compounds, for example, proteins are observed as ions having a variable number of charge states. While the multiple charge phenomenon increases sensitivity, the spectra are more complex and difficult to interpret. Use and detection of a coding moiety with a less complex mass spectrum than the analyte can therefore enhance the resolution of the assay.

Various mass spectrometers may be used in accordance with the methods described herein. Representative examples include: triple quadrupole mass spectrometers, magnetic sector instruments (magnetic tandem mass spectrometer, JEOL, Peabody, Mass.), ionspray mass spectrometers (Bruins et al., Anal Chem. 59:2642-2647, 1987), electrospray mass spectrometers (including tandem, nano- and nano-electrospray tandem) (Fenn et al., Science 246:64-71, 1989), laser desorption time-of-flight mass spectrometers (Karas and Hillenkamp, Anal. Chem. 60:2299-2301, 1988), and a Fourier Transform Ion Cyclotron Resonance Mass Spectrometer (Extrel Corp., Pittsburgh, Mass.).

For additional information regarding mass spectrometers, see, e.g., Principles of Instrumental Analysis, 3rd ed., Skoog, Saunders College Publishing, Philadelphia, 1985; Kirk-Othmer Encyclopedia of Chemical Technology, 4th ed. Vol. 15 (John Wiley & Sons, New York 1995), pp. 1071-1094; Chemushevich and Thomson (EP1006559); Verentchikov et al. (WO/0077823); Clemmer and Reilly (WO/0070335); Hager (WO/0073750); WO99/01889; G. Siuzdak, *Mass Spectrometry for Biotechnology*, Academic Press, N.Y., (1996); Krutchinsky et al., WO 99/38185; Shevchenko et al., (2000) Anal. Chem. 72: 2132-2141; Figeys et al., (1998) Rapid Comm'ns. Mass Spec. 12-1435-144; Li et al. (2000) Anal. Chem. 72: 599-609; Li et al. (2000) Tibtech 18:151-160; Rowley et al. (2000) Methods 20:383-397; Kuster and Mann (1998) Curr. Opin. Structural Biol. 8: 393-400.; Chait et al. (1993) Science 262:89-92; Keough et al. (1999) Proc. Natl. Acad. Sci. USA 96:7131-6; and Bergman (2000) EXS 88:133-44.

In an exemplary embodiment, the mass spectrometry based assay methods described herein are conducted in a high throughput manner as described in C. C. Ozbal, et al., Assay and Drug Development Technologies 2: 373-381 (2004). In certain embodiments, the high throughput mass spectrometry based assay methods described herein utilize an integrated microfluidic system which uses an atmospheric pressure ionization triple quadrupole mass spectrometer as the detection system with electrospray ionization (ESI) or atmospheric pressure chemical ionization (APCI).

In certain embodiments, the invention provides methods for screening for compounds that modulate activity of an acetyltransferase or deacetylase. In certain embodiments, the methods described herein may be used to identify a test compound that decreases or increases acetylase or deacetylase activity by at least about 10%, 25%, 50%, 75%, 80%, 90%, or 100%, or more, relative to the absence of the test compound. In an exemplary embodiment, the methods described herein may be used to identify a sirtuin activating compound that increases deacetylase activity by at least about 10%, 25%, 50%, 75%, 80%, 90%, or 100%, or more, relative to the sirtuin activating activity of resveratrol.

In certain embodiments, the concentration of the peptide substrate in the reaction is below the Km of the enzyme (e.g., acetyltransferase or deacetylase) for the peptide substrate. In certain embodiments, the concentration of the peptide substrate in the reaction may be at least 2-fold, 5-fold, 10-fold, 15-fold, 20-fold, 25-fold, 30-fold, or more, below the Km of the enzyme for the peptide substrate.

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J Med Chem. 37, 2678, 1994; Cho et al., Science 261, 1303, 1993; Carell et al., Angew. Chem. Int. Ed Engl. 33, 2059, 1994; Carell et al., Angew. Chem. Int. Ed. Engl. 33, 2061; Gallop et al., J. Med Chem. 37, 1233, 1994). Libraries of compounds can be presented in solution (see, e.g., Houghten, BioTechniques 13, 412-421, 1992), or on beads (Lam, Nature 354, 82-84, 1991), chips (Fodor, Nature 364, 555-556, 1993), bacteria or spores (Ladner, U.S. Pat. No. 5,223,409), plasmids (Cull et al., Proc. Natl. Acad. Sci. U.S.A. 89, 1865-1869, 1992), or phage (Scott & Smith, Science 249, 386-390, 1990; Devlin, Science 249, 404-406, 1990); Cwirla et al., Proc. Natl. Acad. Sci. 97, 6378-6382, 1990; Felici, J. Mol. Biol. 222, 301-310, 1991; and Ladner, U.S. Pat. No. 5,223,409).

Test compounds can be screened for the ability to modulate acetyltransferase or deacetylase activity using high throughput screening. Using high throughput screening, many discrete compounds can be tested in parallel so that large numbers of test compounds can be quickly screened. The most widely established techniques utilize 96-well microtiter plates. In addition to the plates, many instruments, materials, pipettors, robotics, plate washers, and plate readers are commercially available to fit the 96-well format.

Alternatively, free format assays, or assays that have no physical barrier between samples, can be used. Assays involving free formats are described, for example, in Jayawickreme et al., Proc. Natl. Acad. Sci. U.S.A. 19, 1614-18 (1994); Chelsky, "Strategies for Screening Combinatorial Libraries: Novel and Traditional Approaches," reported at the First Annual Conference of The Society for Biomolecular Screening in Philadelphia, Pa. (Nov. 7-10, 1995); and Salmon et al., Molecular Diversity 2, 57-63 (1996). Another high throughput screening method is described in Beutel et al., U.S. Pat. No. 5,976,813.

In another embodiment, the invention provides kits for measuring the activity of an acetyltransferase or a deacetylase and screening for compounds that inhibit or enhance the acetyltransferase or deacetylase activity as described above. Such kits may be useful for research purposes, drug discovery, diagnostic purposes, etc.

In certain embodiments, a kit may comprise a peptide substrate (as described above) and one or more of the following: a deacetylase, an acetyltransferase, one or more test compounds, a positive control, a negative control, instructions for use, a reaction vessel, buffers, a MALDI matrix, etc. Kits for determination of deacetylase activity may comprise a previously acetylated substrate peptide and kits for determination of acetyltransferase activity may comprise a nonacetylated peptide substrate. The peptide substrate may also comprise a hydrophobic region. In certain embodiments, each component, e.g., the substrate peptide, the deacetylase or acetyltransferase, and/or test compound, may be packaged separately.

Respective components of the kit may be combined so as to realize a final concentration that is suitable for the reaction. Further, in addition to these components, the kit may comprise a buffer that gives a condition suitable for the reaction. The enzyme preparation and the substrate peptide may be combined with other components that stabilize proteins. For example, the kit components may be stored and/or shipped in the presence of about 1% BSA and about 1% polyols (e.g., sucrose or fructose) to prevent protein denaturation after lyophilization.

Each component of the kit can be provided in liquid form or dried form. Detergents, preservatives, buffers, and so on, commonly used in the art may be added to the components so long as they do not inhibit the measurement of the deacetylase or acetyltransferase activity.

Compounds that activate or inhibit the acetyltransferase or deacetylase activity, which can be selected according to the method for screening of the present invention, are useful as candidate compounds for antimicrobial substances, anti-cancer agents, and a variety of other uses. For example, compounds that activate a sirtuin deacetylase protein may be useful for increasing the lifespan of a cell, and treating and/or preventing a wide variety of diseases and disorders including, for example, diseases or disorders related to aging or stress, diabetes, obesity, neurodegenerative diseases, chemotherapeutic induced neuropathy, neuropathy associated with an ischemic event, ocular diseases and/or disorders, cardiovascular disease, blood clotting disorders, inflammation, and/or flushing, etc. In other embodiments, sirtuin deacetylase inhibitors may be useful for a variety of therapeutic applications including, for example, increasing cellular sensitivity to stress, increasing apoptosis, treatment of cancer, stimulation of appetite, and/or stimulation of weight gain, etc.

In certain embodiments, the mass spectrometry assays described herein do not utilize a peptide substrate that is obtained or derived from an HIV Tat protein.

In certain embodiments, the invention provides a method for identifying a compound that activates a sirtuin protein comprising (a) contacting a peptide substrate pool with a sirtuin in the presence of a test compound, wherein members of said peptide substrate pool have the amino acid sequence set forth in SEQ ID NO: 34; and (b) determining the level of acetylation of the peptide substrate pool using mass spectrometry, wherein a decrease in the level of acetylation of the peptide substrate pool in the presence of the test compound as compared to a control is indicative of a compound that activates a sirtuin.

In another embodiment, the invention provides a method for identifying a compound that activates a deacetylase, comprising (a) contacting a peptide substrate pool with a deacetylase in the presence of a test compound, wherein members of said peptide substrate pool comprise at least one acetylated lysine residue, and (b) determining the level of acetylation of the peptide substrate pool using mass spectrometry, wherein a decrease in the level of acetylation of the peptide substrate pool in the presence of the test compound as compared to a control is indicative of a compound that activates a deacetylase, with the proviso that the method does not comprise contacting a peptide substrate pool with a sirtuin in the presence of a test compound, wherein members of said peptide substrate pool have the amino acid sequence set forth in SEQ ID NO: 34.

3. ATP Assays for Sirtuin Activity

In other aspects, the invention provides cell based methods for determining sirtuin activity. The assays comprise contacting a cell with a putative sirtuin modulating compound and then determining cell viability and ATP levels in the cell. An increase in the average ATP level per viable cell is indicative of an increase in sirtuin activity (e.g., a sirtuin activating compound) whereas a decrease in the average ATP level per viable cell is indicative of a decrease in sirtuin activity (e.g., a sirtuin inhibiting compound). In certain embodiments, the assays may further comprise conducting an in vitro assay to determine if the compound has sirtuin modulating activity. Such in vitro assays may be carried out before, after, or simultaneously with the cell based assays.

In certain embodiments, the cell based assays described herein may be used as a secondary screen to further characterize a putative sirtuin modulating compound. For example, the cell based assays may be used to confirm that a sirtuin modulating compound identified in vitro has sirtuin modulating activity in a cellular environment, provide information about cell membrane permeability and/or cellular toxicity. Compounds that show a lower level of sirtuin modulating activity in a cell based assay as compared to an in vitro assay may be indicative of compounds that have low cell membrane permeability or compounds that are cell membrane impermeable. Additionally, compounds that show sirtuin activating activity in an in vitro assay but show sirtuin inhibiting activity in a cell based assay may be indicative of compounds that are cytotoxic. Accordingly, such cell based assays will provide useful information for developing therapeutic agents. In certain embodiments, the cell based methods described herein may be used to determine the effect of a putative sirtuin modulating compound on mitochondrial biogenesis.

In exemplary embodiments, the cell based methods for determining sirtuin activity described herein may utilize a sirtuin activatable cell line. A sirtuin activatable cell line is a cell line that is suitable for use in the cell based sirtuin activating assays described herein. A sirtuin activatable cell line comprises a relatively low endogenous level of one or more sirtuin proteins (e.g., the amount of sirtuin activity in the cell is not saturating and an increase in activity is observable) and a relatively low level of mitochondria and/or oxidative phosphorylation capacity (e.g., the amount of mitochondria and/or oxidative phosphorylation in the cell is not saturating and an increase in ATP levels is observable). A sirtuin activatable cell line may be identified using the methods described in the Exemplification section below. Exemplary sirtuin activatable cell lines include, for example, NCI-H358 and MCS7.

In certain embodiments, the cell based methods for determining sirtuin activity described herein involve determination of ATP levels in a cell or sample of cells. ATP levels can be determined by any method known in the art or any method yet to be discovered. Reagent formulations containing luciferase and luciferin for assaying ATP in a sample are known in the art. For example, U.S. Pat. No. 6,004,767 of Crouch et al. discloses a bioluminescent reagent as a freeze dried powder, to be reconstituted prior to use. U.S. Pat. No. 5,558,986 of Lundin discloses such reagent formulation for use in combination with a cyclodextrin. US patent application No. 2001/0046687 of DiCesare also discloses the use of such formulation, wherein trehalose is used to enhance the emission of light intensity. Published international patent application, WO 94/11528 of Foote and Grant discloses an aqueous composition including polyols for use in a bioluminescent assay by adding a strong buffer to give a pH which is close to the optimum pH for the luciferase reaction. Other assays for determining ATP levels are described in U.S. Pat. Nos. 5,618,682; 3,933,592; 4,303,752; U.S. Patent Publication Nos. 2006/0073537; 2005/0124018; 2003/0104507; 2006/0008860; and PCT Publication No. WO 00/18953. Additionally, a variety of kits for determining ATP levels are commercially available from a variety of sources, including, for example, ATP Assay Kit (Calbiochem, San Diego, Calif.), ATP Determination Kit (Molecular Probes (Invitrogen), Eugene, Oreg.), ENLITEN ATP Assay System (Promega, Madison, Wis.), ATP Bioluminescence Assay Kit (Roche Applied Science, Indianapolis, Ind.), Adenosine 5'-triphosphate (ATP) Bioluminescent Assay Kit (Sigma-Aldrich, St. Louis, Mo.), ATP Assay Kit (Thermo Electron Corporation, Milford, Mass.).

In certain embodiments, the cell based methods for determining sirtuin activity described herein involve determination of cell viability in sample of cells. Cell viability can be determined by any method known in the art or any method yet to be discovered. Exemplary methods for determining cell viability include, for example, Alamar Blue, Brd U, MTT, Trypan Blue exclusion, $^3$H-thymidine incorporation, and XTT assays. Kits for determining cell viability are commercially available from a variety of sources.

In certain embodiments, the cell based methods for determining sirtuin activity described herein may further comprise determination of sirtuin activity in an in vitro assay. Sirtuin activity can be determined by any method known in the art or any method yet to be discovered. Assays for determining sirtuin activity may be conducted in a cell based or cell free format. For example, an assay may comprise incubating (or contacting) a sirtuin with a test agent under conditions in which a sirtuin can be activated by an agent known to activate the sirtuin, and monitoring or determining the level of activation of the sirtuin in the presence of the test agent relative to the absence of the test agent. The level of activation of a sirtuin can be determined by determining its ability to deacetylate a substrate. Exemplary substrates are acetylated peptides, for example, peptides from BIOMOL (Plymouth Meeting, Pa.), peptides of p53 (such as those comprising an acetylated K382), the Fluor de Lys-SIRT1 (BIOMOL) acetylated peptide (Arg-His-Lys-Lys), peptides from human histories H3 and H4, an acetylated amino acid, and the other peptide substrates described herein. The HDAC fluorescent activity assay/drug discovery kit (AK-500, BIOMOL Research Laboratories) may be used to determine the level of acetylation. Methods for determining sirtuin activity have been described. For example, Bitterman et al. (2002) J. Biol. Chem. 277:45099 describe a fluorescence based assay for determination of sirtuin activity. Additionally, fluorescent enzyme assay kits for determining sirtuin activity are commercially available (Biomol International L.P., Plymouth Meeting, Pa.). Other suitable assays for identifying sirtuin activators include a fluorescence polarization based assay described in PCT/US06/07748 or the mass spectrometry assays described herein.

In certain embodiments, the cell based assays described herein may comprise determination of ATP levels and cell viability at one or more fixed time points after contacting the cells with a potential sirtuin modulating compound. In exemplary embodiments, ATP level and cell viability are determined at about 12-84 hours, about 24-72 hours, about 36-60 hours, or at about 48 hours after exposure of the cells to a potential sirtuin modulating compound.

In certain embodiments, the cell based assays described herein may comprise determination of ATP level and cell viability in a sample of cells that are growing logrhythmically (e.g., log phase growth).

In certain embodiments, the cell based assays described herein may utilize controls. For example, controls include duplicate assays in which cell samples are contacted with vehicle alone or with a sirtuin modulating compound having known activity (e.g., a sirtuin activating compound, sirtuin inhibiting compound, and/or a compound having no sirtuin modulating activity).

EXEMPLIFICATION

The invention now being generally described, it will be more readily understood by reference to the following examples which are included merely for purposes of illustration of certain aspects and embodiments of the present invention, and are not intended to limit the invention in any way.

Example 1

SIRT1 Enzyme Titration and Time Course

This example describes the development of the SIRT1 in vitro mass spectrometry enzyme assay for the $NAD^+$-dependent deacetylase, SIRT1. The mass spectrometry based assay utilizes a peptide having 20 amino acid residues as follows: Ac-EE-K(biotin)-GQSTSSHSK(Ac)NleSTEG-K(5TMR)-EE-NH2 (SEQ ID NO: 34) wherein K(Ac) is an acetylated lysine residue and Nle is a norleucine. The peptide is labeled with the fluorophore 5TMR (excitation 540 nm emission 580 nm) at the C-terminus. The sequence of the peptide substrate is based on p53 with several modifications. In addition, the methionine residue naturally present in the sequence was replaced with the norleucine because the methionine may be susceptible to oxidation during synthesis and purification. An identical peptide lacking the acetyl group on the lysine was also synthesized as a standard for the expected product in the mass spectrometry assay. This second peptide having 20 amino acid residues is as follows: Ac-EE-K(biotin)-GQSTSSHSKNleSTEG-K(5TMR)-EE-NH2 (SEQ ID NO: 35) wherein Nle is a norleucine. The peptide is also labeled with the fluorophore 5TMR (excitation 540 nm/emission 580 mm) at the C-terminus. In addition, the methionine residue naturally present in the sequence was replaced with the norleucine because the methionine may be susceptible to oxidation during synthesis and purification. SIRT1 acetylated and deacetylated peptide substrates were obtained from Biopeptide, Inc. (San Diego, Calif.).

Mass spectrometry can be used to detect the change in mass observed in a peptide substrate following deacetylation as deacetylation results in a mass change of 44 atomic mass units (AMU) in the peptide substrate (i.e. the difference in expected mass units between the peptide corresponding to SEQ ID NO: 34 and SEQ ID NO: 35). A mass spectrometry analytical method for the detection of SIRT1 Acetylated Peptide Substrate and SIRT1 Deacetylated Peptide Substrate was developed using substrate and product peptide standards. Mass Spectrometry was done via high throughput as described in Ozbal et al. (Assay and Drug Development Technologies, 2 (4), 2004). To develop the SIRT1 enzyme assay, the dependence of product formation on SIRT1 enzyme concentration and incubation time was established. Hence, this method can be used to screen NCEs, in a HTS (High Throughput Screen) manner, against SIRT1 to identify inhibitors and/or activators.

SIRT1 protein was expressed and purified as follows. The SirT1 gene was cloned into a T7-promoter containing vector and transformed into BL21(DE3). The protein was expressed by induction with 1 mM IPTG as an N-terminal His-tag fusion protein at 18° C. overnight and harvested at 30,000×g. Cells were lysed with lysozyme in lysis buffer (50 mM Tris-HCl, 2 mM Tris[2-carboxyethyl] phosphine (TCEP), 10 μM $ZnCl_2$, 200 mM NaCl) and further treated with sonication for 10 min for complete lysis. The protein was purified over a Ni-NTA column (Amersham) and fractions containing pure protein were pooled, concentrated and run over a sizing column (Sephadex S200 26/60 global). The peak containing soluble protein was collected and run on an Ion-exchange column (MonoQ). Gradient elution (200 mM-500 mM NaCl) yielded pure protein. This protein was concentrated and dialyzed against dialysis buffer (20 mM Tris-HCl, 2 mM TCEP) overnight. The protein was aliquoted and frozen at −80° C. until further use.

To establish the dependence of the enzyme assay on SIRT1 enzyme concentration and incubation time, a rate based experiment was performed using multiple concentrations of SIRT1 enzyme. The assay employs mass spectrometry to monitor the conversion of Acetylated Peptide Substrate to Deacetylated Peptide Product by SIRT1. A schematic of the assay is shown in FIG. 1.

Briefly, 1 μL of vehicle (DMSO) was added to each well of Costar 96-well clear round bottom assay plate. Formic acid (10 μL of 10%) was added to all of the wells in column 1 of the 96-well assay plate. Eight stock concentrations of SIRT1 (80, 40, 20, 10, 5, 2.5, 1.25, and 0.63 nM) were prepared in an Enzyme Working Solution (50 mM Tris HCl pH 8.0, 137 mM, NaCl, 2.7 mM, KCl, 1 mM $MgCl_2$, 5 mM DTT, and 0.05% BSA). 50 μL of each SIRT1 stock was added to a row of the 96-well assay plate. (e.g. the 80 nM dose was added to all wells in row A, the 40 nM dose was added to all wells in row B, etc.).

To initiate the reaction, 50 μL of Substrate Working Solution (1 μM SIRT1 Acetylated Peptide Substrate, 240 μM $NAD^+$, 50 mM Tris HCl pH 8.0, 137 mM NaCl, 2.7 mM KCl, 1 mM $MgCl_2$, 5 mM DTT, and 0.05% BSA) was added to all wells of the 96-well assay plate.

At 0, 5, 10, 15, 25, 35, 45, 60, 75, 90, 105, and 120 minutes, the reaction was stopped by addition of 10% formic acid and the conversion of substrate to product was determined by mass spectrometry. The removal of an acetyl group results in the loss of 44 AMU from the original peptide substrate. The activity of each concentration of SIRT1 was monitored by comparing the percent conversion of Acetylated Peptide Substrate to Deacetylated Peptide Product over time.

The final conditions of the assay were SIRT1 (40, 20, 10, 5, 2.5, 1.25, 0.63 or 0.031 nM), 0.5 μM SIRT1 Acetylated Peptide Substrate, 120 μM $NAD^+$, 50 mM Tris HCl pH 8.0, 137 mM NaCl, 2.7 mM KCl, 1 mM $MgCl_2$, 5 mM DTT, 0.05% BSA and 25° C.

The ability of SIRT1 to convert Acetylated Peptide Substrate into Deacetylated Peptide Product was evaluated at 8 different concentrations of SIRT1, in the presence of vehicle (DMSO), at multiple time points. The rate of product formation versus time was plotted for each concentration of SIRT1 enzyme tested. The rate in the linear part of the curve was determined.

Results

Figure 2:
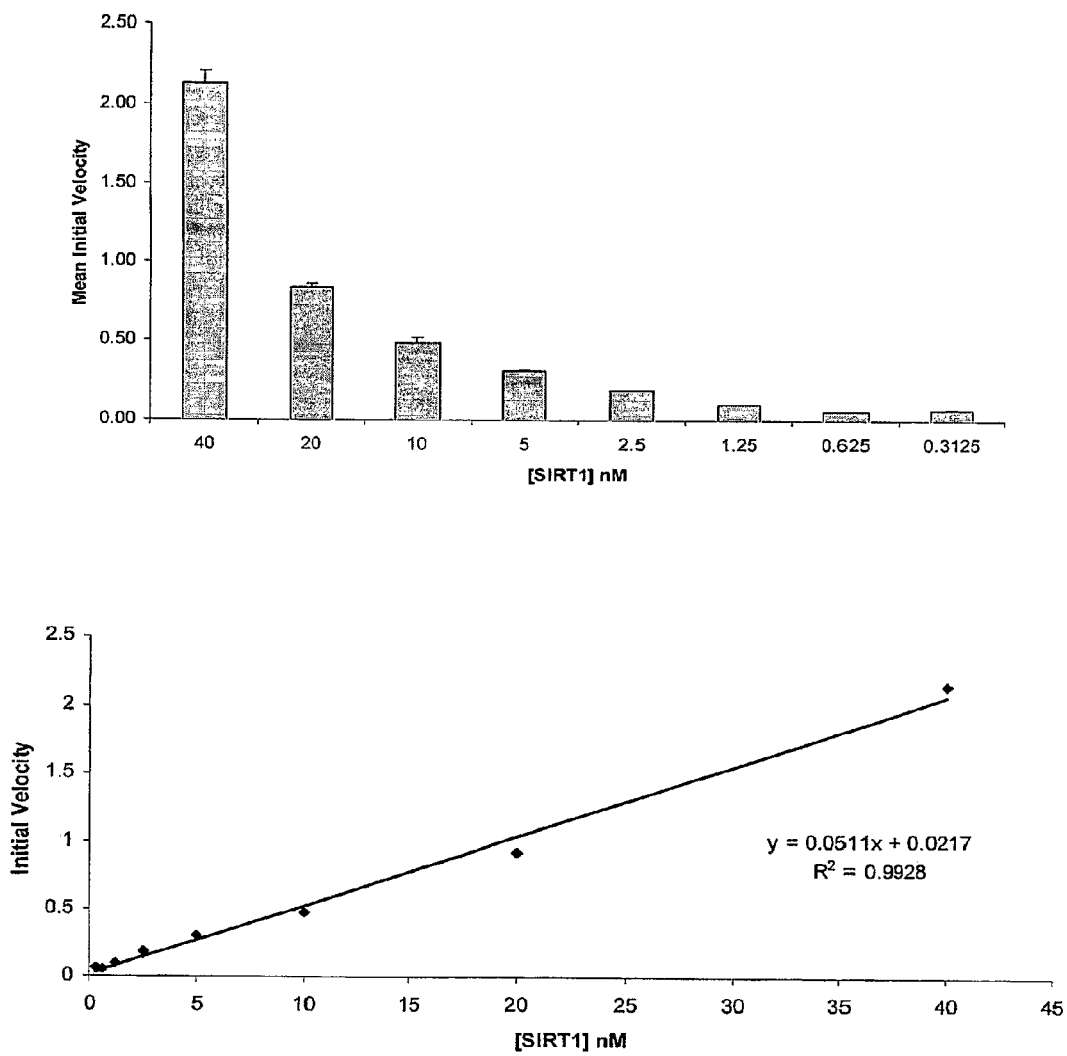
FIG. 2 shows a bar plot of a SIRT1 enzyme titration time course MS mass spectrometry assay (top panel) and a plot of initial velocity vs. enzyme concentration (bottom panel).

FIG. 2 shows the initial velocity determined at each SIRT1 concentration tested. SIRT1 deacetylation activity is dependent on both enzyme concentration and incubation time. Concentrations of enzyme between 5-20 nM result in product formation well above background. Based on these results, 10 nM SIRT1 was selected as the standard condition for the assay.

Example 2

Determination of SIRT1 Km for Acetylated Peptide Substrate

Figure 3:
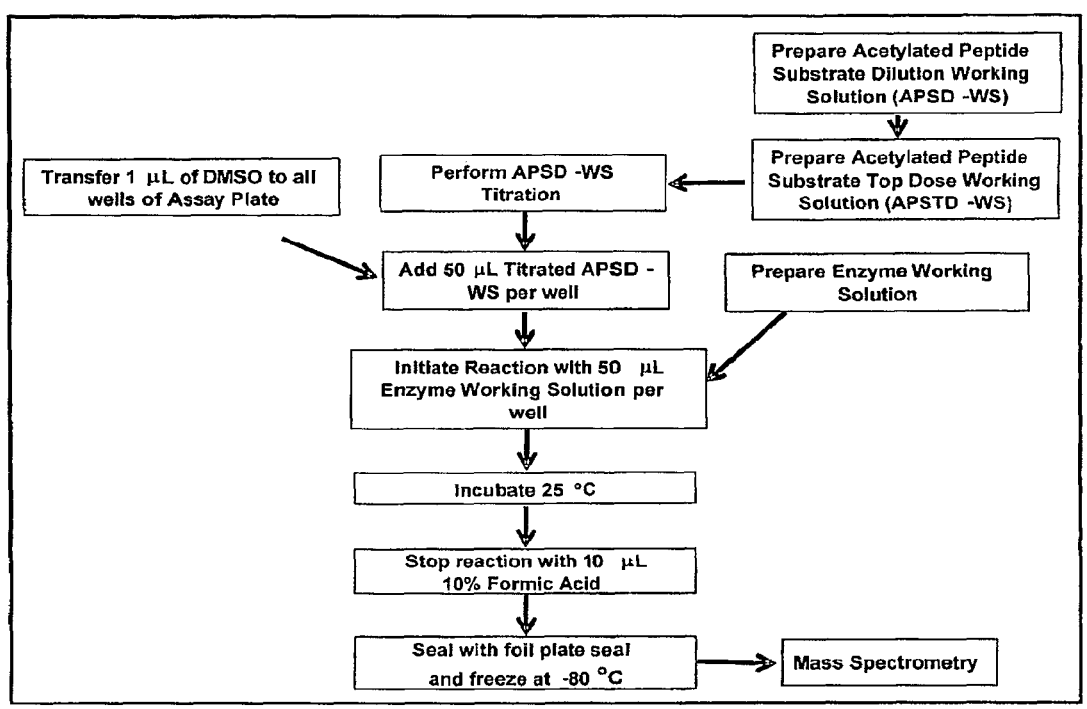
FIG. 3 shows a schematic outline of a SIRT1 Km for acetylated peptide substrate assay.

To determine the Km of SIRT1 for Acetylated Peptide Substrate, the linear rate was determined at twelve concentrations of Acetylated Peptide Substrate (50, 25, 12.5, 6.25, 3.12, 1.56, 0.78, 0.39, 0.19, 0.098, 0.049, and 0.024 µM) in the presence of vehicle (1% DMSO). A schematic of the assay is shown in FIG. 3.

Briefly, 1 µL of vehicle (DMSO) was added to each well of a Costar 96-well clear round bottom assay plate and 10 µL of 10% formic acid was added to all of the wells in row A. The Acetylated Peptide Substrate was serially diluted. Wells A2, A3, A4, A5, A6, A7, A8, A9, A10, A11 and A12 of a Costar 2 mL 96 well Assay Block were filled with 600 µL of Substrate Dilution Working Solution (SDWS; 4 mM NAD$^+$, 50 mM Tris HCl pH 8.0, 137 mM NaCl, 2.7 mM KCl, 1 mM MgCl$_2$, 5 mM DTT, and 0.05% BSA). 1200 µL Acetylated Peptide Substrate Top Dose Working Solution (APSTD-WS; 100 µM SIRT1 Acetylated Peptide Substrate, 4 mM NAD$^+$, 50 mM Tris HCl pH 8.0, 137 mM NaCl, 2.7 mM KCl, 1 mM MgCl$_2$, 5 mM DTT, and 0.05% BSA) was added to well A1 of the Costar 2 mL 96 well Assay Block. The APSTD-WS was serially diluted into SDWS by transferring 600 µL of APSTD-WS from well A1 to Well B1 of the Costar 2 mL 96 well Assay Block. The solution was mixed 5 times and the process was continued by moving across row A, until well A12 was reached.

The Enzyme Working Solution (20 nM SIRT1, 50 mM Tris HCl pH 8.0, 137 mM NaCl, 2.7 mM KCl, 1 mM MgCl$_2$, 5 mM DTT, 0.05% BSA) was prepared. 50 µL of serial diluted APSTD-WS was transferred from the entire row A of the Costar 2 mL 96 well Assay Block to each row of the 96-well assay plate using a 12 channel pipette (e.g. from row A of the 2 mL Assay block, to row A, B, C, D, E, F, G, H of the 96-well assay plate). To initiate the reaction, 50 µL of Enzyme Working Solution was added to each well of the 96-well assay plate using the Multidrop.

At 0, 3, 6, 9, 12, 15, 20, and 25 minutes, the reaction was stopped with 10% formic acid and the conversion of substrate to product was determined by mass spectrometry.

The final conditions of the assay were 10 nM SIRT1, 50, 25, 12.5, 6.25, 3.12, 1.56, 0.78, 0.39, 0.19, 0.098, 0.049, or 0.024 µM SIRT1 Acetylated Peptide Substrate, 2 mM NAD$^+$, 50 mM Tris HCl pH 8.0, 137 mM NaCl, 2.7 mM KCl, 1 mM MgCl$_2$, 5 mM DTT, 0.05% BSA and 25° C.

The Km of SIRT1 for the Acetylated Peptide Substrate was determined in the presence of vehicle (1% DMSO). SIRT1 enzyme activity at 12 concentrations of SIRT1 Acetylated Peptide Substrate was monitored by comparing the percent conversion of Acetylated Peptide Substrate to Deacetylated Peptide Product over time. The reaction rate at each substrate concentration was determined as the slope of the product formation versus time plot in the linear range. The rates obtained were then plotted against the substrate concentration to generate a plot for determination of the Km.

Results

Figure 4:
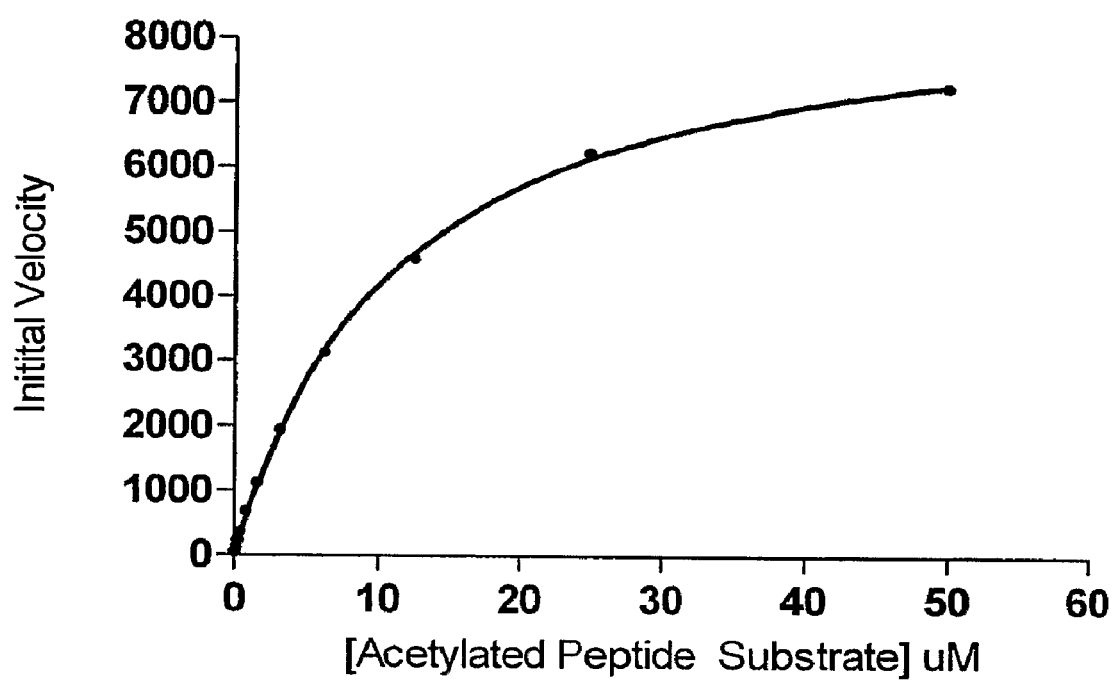
FIG. 4 shows a representative plot of a SIRT1 Km for acetylated peptide substrate.

As represented in FIG. 4, the Km of SIRT1 for Acetylated Peptide Substrate was determined in 2 replicate plates to be 11.2 µM and 11.9 µM resulting in a mean Km of 11.6 µM. The standard assay conditions were established at sub-Km concentrations (0.5 µM Acetylated Peptide Substrate) of peptide substrate in order to maximize the effect of Km-type activators.

Example 3

Determination of SIRT1 Km for NAD$^+$

Figure 5:
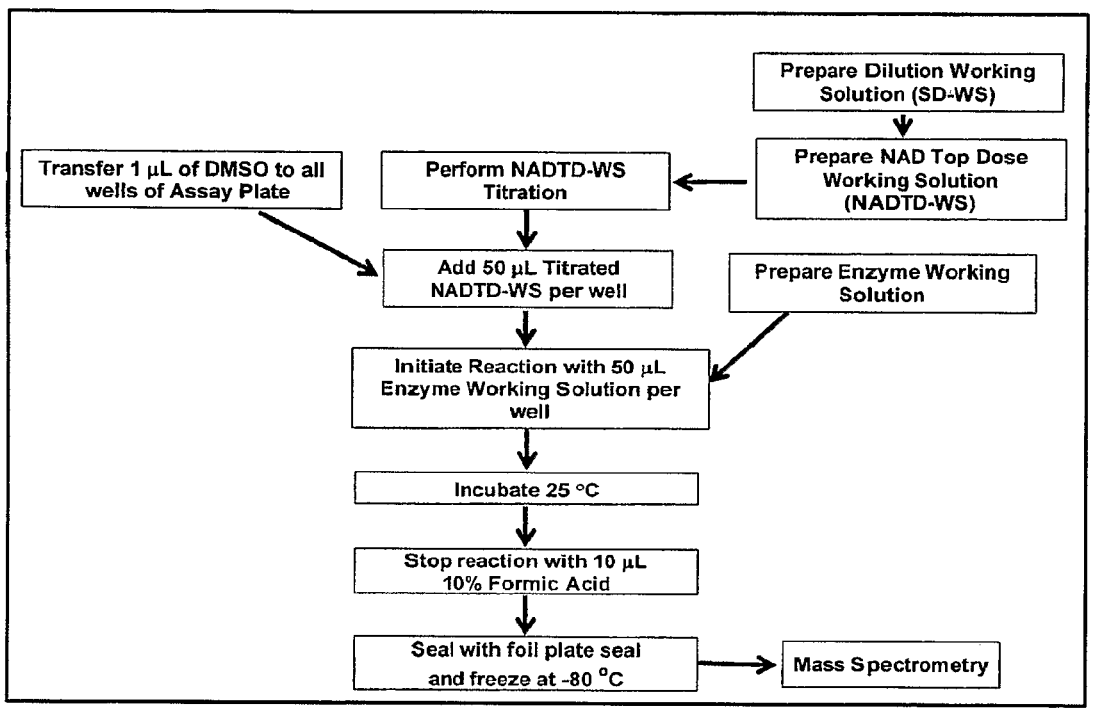
FIG. 5 shows a schematic outline of a SIRT1 Km for $NAD^+$ assay.

To determine the Km for NAD$^+$, the linear rate was determined at 8 concentrations of NAD$^+$ (2000, 1000, 500, 250, 125, 62.5, 31.25 and 15.6 µM) in vehicle (1% DMSO). A schematic of the assay design is shown in FIG. 5.

Vehicle (1 µL DMSO) was added to each well of a Costar 96-well clear round bottom assay plate and 10 µL of 10% formic acid was added to all of the wells in row A of the 96 well assay plate.

NAD$^+$ was serially diluted in a Costar 2 mL 96 well Assay Block by first filling wells B1, C1, D1, E1, F1, G1, H1 with 600 µL of Substrate Dilution Working Solution (SDWS; 100 µM Acetylated Peptide Substrate, 50 mM Tris HCl pH 8.0, 137 mM NaCl, 2.7 mM KCl, 1 mM MgCl$_2$, 5 mM DTT, and 0.05% BSA). A total of 1200 µL of the NAD$^+$ Top Dose Working Solution (NADTD-WS; 100 µM SIRT1 Acetylated Peptide Substrate, 4 mM NAD$^+$, 50 mM Tris HCl pH 8.0, 137 mM NaCl, 2.7 mM KCl, 1 mM MgCl$_2$, 5 mM DTT, and 0.05% BSA) were added to well A1 of the Costar 2 mL 96 well Assay Block. The NADTD-WS was serially diluted into SDWS by transferring 600 µL of NADTD-WS from well A1 to well B1 of the Costar 2 mL 96 well Assay Block. The solutions were mixed 5 times and the process was repeated until well H1 was reached.

The Enzyme Working Solution (20 mM SIRT1, 50 mM Tris HCl pH 8.0, 137 mM NaCl, 2.7 mM KCl, 1 mM MgCl$_2$, 5 mM DTT, and 0.05% BSA) was prepared.

The serial diluted NADTD-WS (50 µL) was transferred to every column of the 96-well assay plate from the entire column 1 of the Costar 2 mL 96 well Assay Block using an 8 Channel Pipette (e.g. from column 1 of the 2 mL Assay block, to columns 1-12 off the 96-well assay plate). To initiate the reaction, 50 µL of Enzyme Working Solution was added to each well of the 96-well assay plate using the Multidrop.

At 0, 10, 15, 20, 30 minutes, the reaction was stopped with 10% formic acid and the conversion of substrate to product was determined by mass spectrometry. The activity at each concentration of NAD$^+$ was monitored by comparing the percent conversion of Acetylated Peptide Substrate to Deacetylated Peptide Product over time.

The final conditions of the assay were 10 nM SIRT1, 2000, 1000, 500, 250, 125, 62.5, 31.25 or 15.6 µM NAD$^+$, 50 µM SIRT1 Acetylated Peptide Substrate, 50 mM Tris HCl pH 8.0, 137 mM NaCl, 2.7 mM KCl, 1 mM MgCl$_2$, 5 mM DTT, 0.05% BSA and 25° C.

The Km of SIRT1 for NAD$^+$ was determined in the presence of vehicle (1% DMSO). SIRT1 enzyme activity at 8 concentrations of NAD$^+$ was monitored by comparing the percent conversion of Acetylated Peptide Substrate to Deacetylated Peptide Product over time. The reaction rate at each NAD$^+$ concentration was determined as the slope of the product formation versus time plot in the linear range. The rates obtained were then plotted against the NAD$^+$ concentration to generate a plot for determination of the Km.

Results

Figure 6:
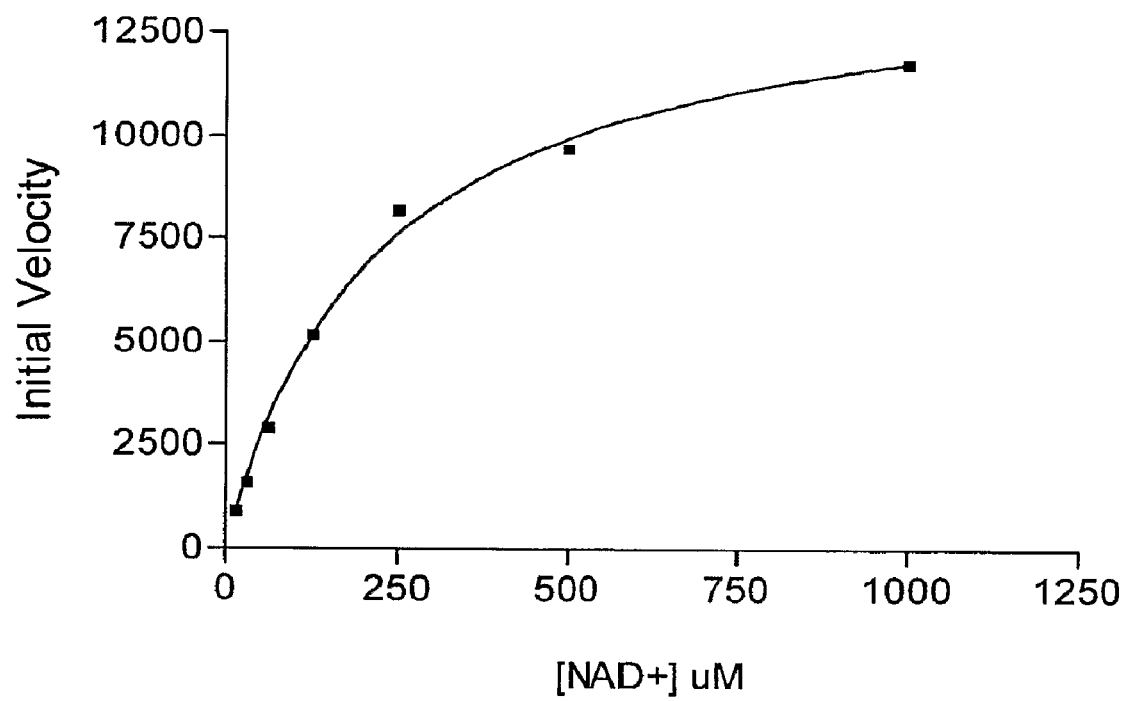
FIG. 6 shows a plot of SIRT1 Km for $NAD^+$.

The Km of SIRT1 for NAD$^+$ was determined to be 220 µM (FIG. 6). The standard assay conditions were established at sub-Km concentrations (120 µM NAD$^+$) of peptide substrate in order to maximize the effect of Km-type activators.

Example 4

Determination of DMSO Tolerance SIRT1 Mass Spectrometry Assay

Figure 7:
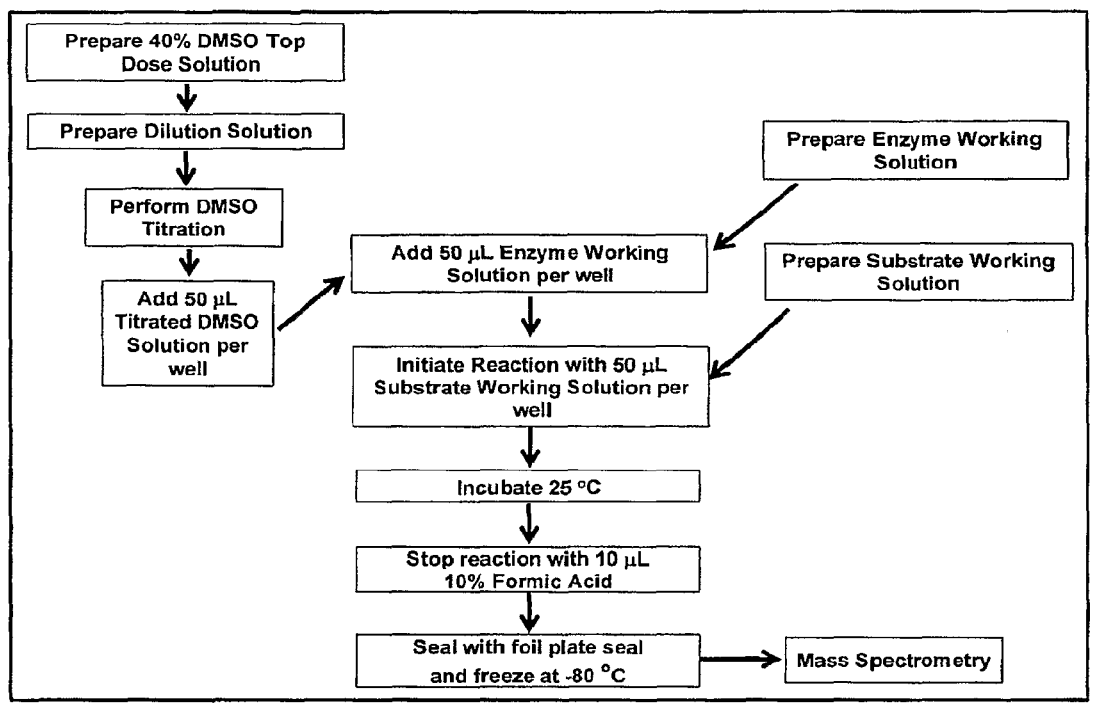
FIG. 7 shows a schematic of a SIRT1 DMSO tolerance mass spectrometry assay.

To determine the tolerance of the SIRT1 mass spectrometry assay for DMSO, a rate based experiment was performed at multiple concentrations of DMSO. A schematic of the assay design is shown in FIG. 7.

Formic acid (10 µL of 10%) was added to all of the wells in column 1 of the 96 well assay plate. Eight concentrations of DMSO (40%, 20%, 10%, 5.0%, 2.5%, 1.25%, 0.625%, and 0.313%) were prepared in buffer containing 50 mM Tris HCl pH 8.0, 137 mM, NaCl, 2.7 mM, KCl, 1 mM $MgCl_2$, 5 mM DTT, and 0.05% BSA.

This DMSO titration was prepared by making a 2000 µL solution of 40% DMSO in 50 mM Tris HCl pH 8.0, 137 mM, NaCl, 2.7 mM, KCl, 1 mM $MgCl_2$, 5 mM DTT, and 0.05%. BSA in well A1 of a Costar 2 mL 96 well Assay Block. Dilution Working Solution (1000 µL; 50 mM Tris HCl pH 8.0, 137 mM, NaCl, 2.7 mM, KCl, 1 mM $MgCl_2$, 5 mM DTT, and 0.05% BSA) was added to wells B1, C1, D1, E1, F1, G1 and H1. 1000 µL of the 40% DMSO in buffer solution was transferred from A1 to A2 and the solution was mixed 5 times. This process was repeated with wells in column 1 until well H1 was reached.

Using an 8 channel multi-pipette, 50 µl was transferred from column 1 of the 2 mL 96 well assay block to all columns of a 96 well assay plate.

25 µL of Enzyme Working Solution (40 nM SIRT1, 50 mM Tris HCl pH 8.0, 137 mM, NaCl, 2.7 mM, KCl, 1 mM $MgCl_2$, 5 mM DTT, and 0.05% BSA) was prepared and added to each well of the 96-well round bottom assay plate.

To initiate the reaction, 25 µL of Substrate Working Solution (2 µM SIRT1 Acetylated Peptide Substrate, 480 µM NAD, 50 mM Tris HCl pH 8.0, 137 mM NaCl, 2.7 mM KCl, 1 mM $MgCl_2$, 5 mM DTT, and 0.05% BSA) was added to all wells of the 96-well assay plate.

At 0, 2, 5, 10, 15, 20, 25, 25, 30, 35, 40, 45, and 60 minutes, the reaction was stopped with 10% formic acid and the conversion of substrate to product was determined by mass spectrometry. The activity of SIRT1 at each concentration of DMSO was monitored by comparing the percent conversion of Acetylated Peptide Substrate to Deacetylated Peptide Product over time.

The final conditions of the assay were 10 nM SIRT1, 0.5 µM SIRT1 Acetylated Peptide Substrate, 120 µM NAD, 50 mM Tris HCl pH 8.0, 137 mM NaCl, 2.7 mM KCl, 1 mM $MgCl_2$, 5 mM DTT, 0.05% BSA, and DMSO (20%, 10%, 5%, 2.5%, 1.25%, 0.63% or 0.031%, 0.156%)

Product formation versus time was plotted for each concentration of DMSO tested. The rate was determined by taking the slope from the linear part of the time course. The rate was plotted versus the DMSO concentration in a bar graph for comparison of the different treatments.

Results

Figure 8:
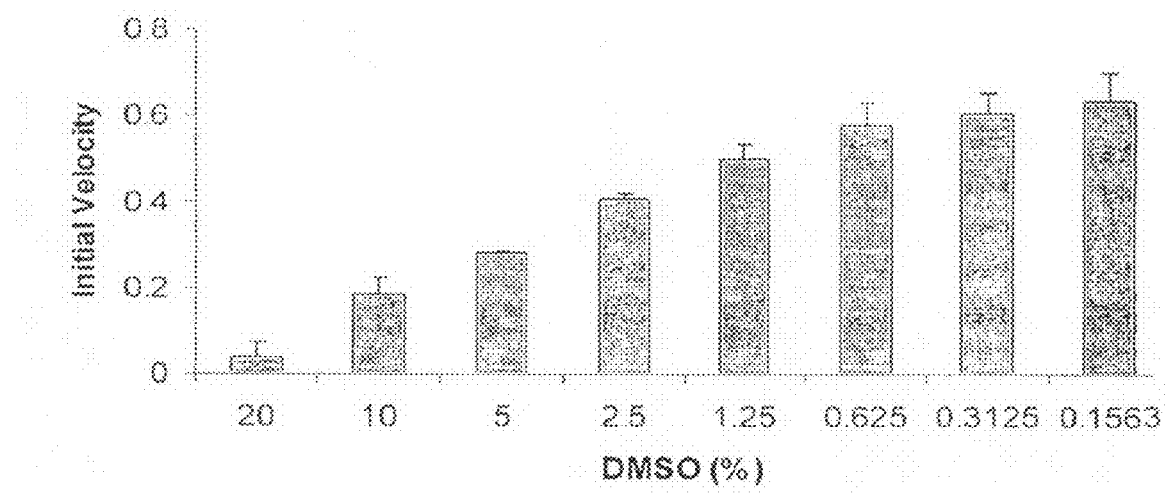
FIG. 8 shows a bar plot of SIRT1 mass spectrometry initial velocity vs. DMSO concentration.

Data are presented as the initial velocity obtained at each concentration of DMSO. The results demonstrate that SIRT1 enzyme activity is sensitive to DMSO at concentrations greater than 0.625% (FIG. 8). Enzyme activity was decreased by 36% at 2.5% DMSO, by 21% at 1.25% DMSO and by 9.1% at 0.625% DMSO. Based on these results, the concentration of DMSO in the reaction under the standard assay conditions should not exceed 1% final.

Example 5

Determination of Mechanism of Activation of SIRT1 by Resveratrol

Figure 9:
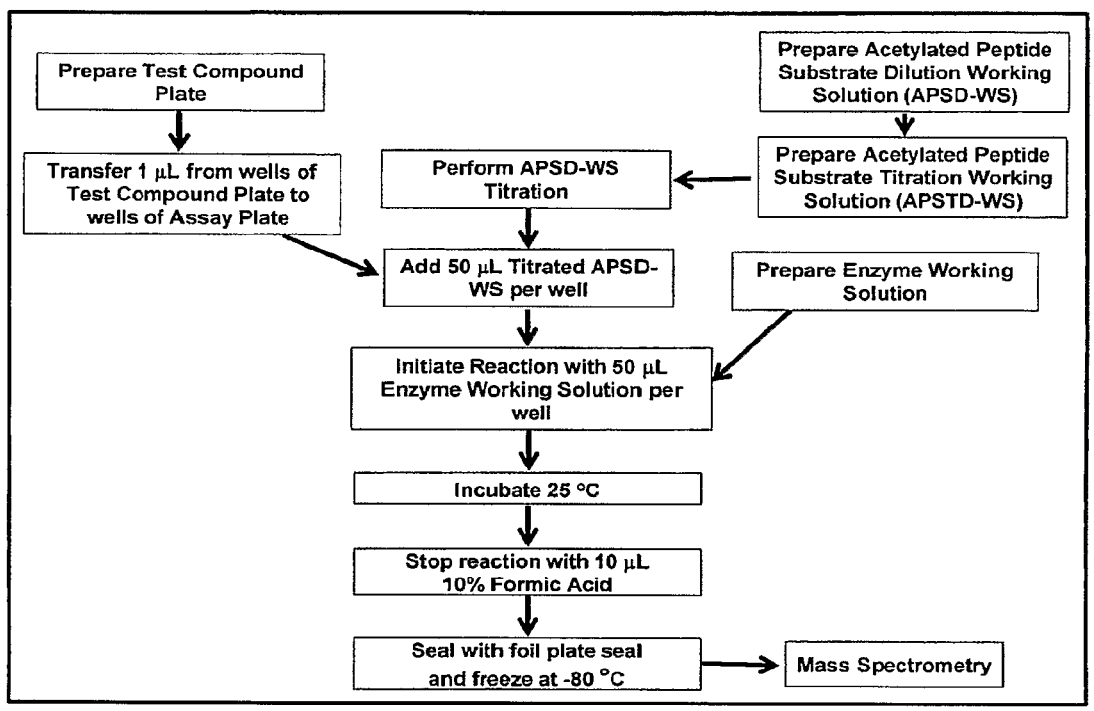
FIG. 9 shows a schematic of a Km mass spectrometry assay.

The purpose of this example was to address the mechanism by which the small molecule, resveratrol, activates SIRT1 enzyme activity. The effect of resveratrol on the Km of human SIRT1 enzyme for Acetylated Peptide Substrate was examined using the SIRT1 Mass Spectrometry Assay described in the previous examples. The experimental design is diagrammed in FIG. 9. Using the cell-free MS assay, the Km of SIRT1 enzyme for peptide substrate was determined at five concentrations of resveratrol (100, 33, 11, 3.7, 1.2 µM) and also in the presence of DMSO vehicle alone. To determine the Km, the linear rate was determined at 12 concentrations of Acetylated Peptide Substrate (50, 25, 12.5, 6.25, 3.12, 1.56, 0.78, 0.39, 0.19, 0.098, 0.049, and 0.024 µM) for each of the resveratrol concentrations and for the vehicle control. SIRT1 enzyme, $NAD^+$, and 0-50 µM Acetylated Peptide Substrate are incubated with 0-100 µM resveratrol at 25° C. At 0, 3, 6, 9, 12, 15, 20, and 25 minutes, the reaction was stopped with 10% formic acid and the conversion of substrates to products determined by mass spectrometry.

Resveratrol was weighed and placed in a brown vial. The material was dissolved in 100% vehicle (DMSO) to yield a final concentration of 10 mM (stock solution). The stock solution was serially diluted with 100% DMSO in a deep well 96-well plate.

Briefly, 337.5 µL of 10 mM resveratrol was pipetted into well A1 and serially diluted three-fold four times so that 112.5 µL of 10 mM stock was added to 225 µL of 100% DMSO and mixed 10 times with a pipette. This procedure resulted in 3.3 mM resveratrol stock in well A2, 1.1 mM resveratrol in well A3, 0.37 mM resveratrol in well A4, and 0.12 mM resveratrol in well A5. 25 µL of A1-A5 was transferred down the 96 well plate into rows B-H. Next, using an 8 channel pippetor 14 µL was withdrawn from column 1 (10 mM resveratrol) of the Mother Stock Plate and 1 µL was dispensed into waste and then 1 µL was distributed across a daughter plate into columns 1-12. This procedure yielded an entire 96 well plate containing 1 µL/well of 10 mM resveratrol. This procedure was repeated to create plates containing 1 µL/well of the 3.3, 1.1, 0.37, and 0.12 mM resveratrol. Two plates containing 1 µL/well of 100% DMSO were also generated in order to determine the Km in the presence of vehicle alone.

The Km of SIRT1 for the Acetylated Peptide Substrate was determined at 5 different concentrations of resveratrol and in the presence of vehicle alone. To determine the Km, the rate of conversion of substrate to product was determined at multiple time points in the linear range of the assay.

Results

Figure 10:
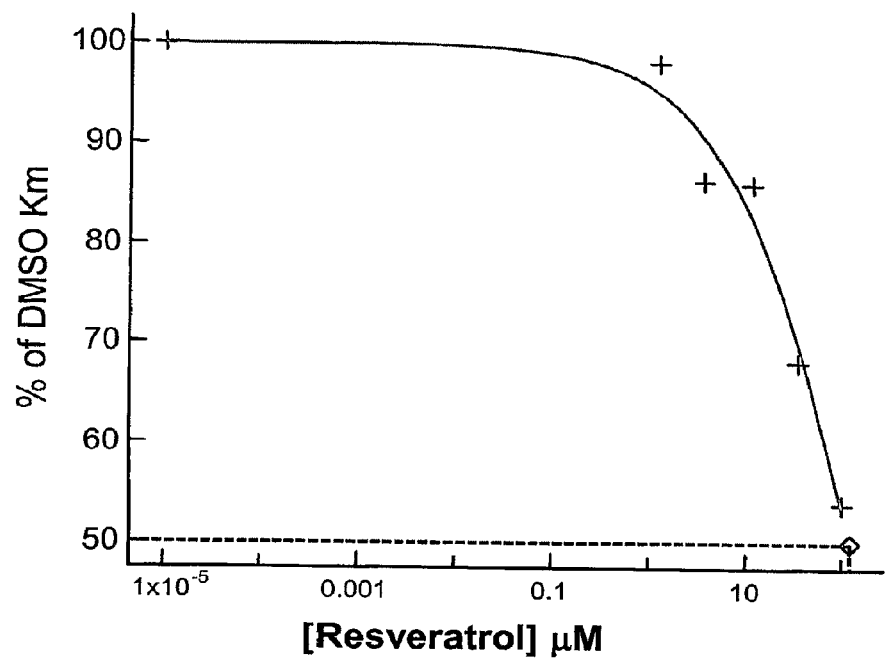
FIG. 10 shows the effect of resveratrol on the Km of SIRT1 for the acetylated peptide substrate. The top panel shows a plot of resveratrol concentration (µM) vs. % DMSO Km and the bottom panel shows a bar plot of resveratrol concentration (µM) vs. Km for peptide (µM).
Figure 10:
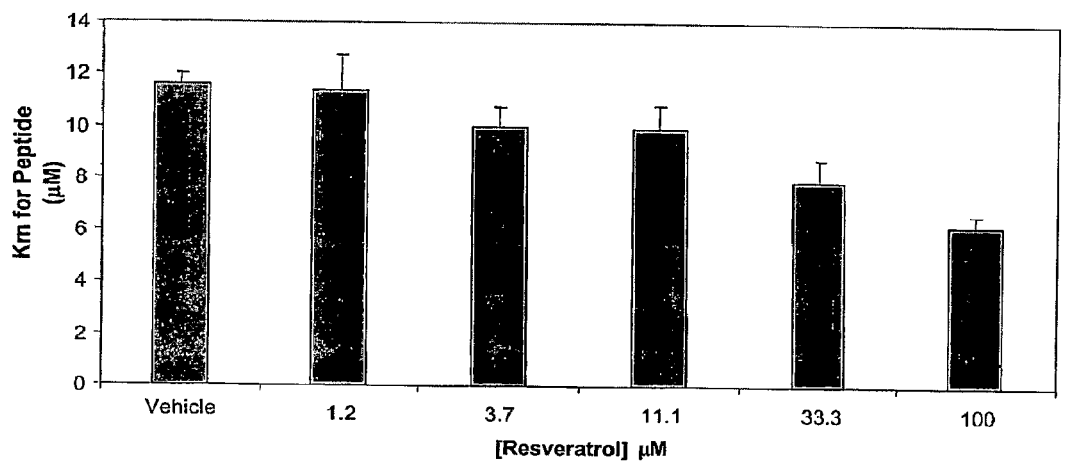

Data are presented as the % of the Km in the presence of vehicle (% of DMSO Km) vs. resveratrol concentration (FIG. 10). Resveratrol decreased the Km of SIRT1 for peptide substrate in a dose dependent manner. The Km for peptide substrate decreased by 2%, 14%, 14%, 32%, and 46% at 1.2, 3.7, 11, 33, and 100 µM resveratrol, respectively.

Example 6

Determination of Mechanism of Activation of SIRT1 by Test Compounds

The purpose of this example is to describe the effect of SIRT1 small molecule activators on the Km of SIRT1 for the Acetylated Peptide Substrate by mass spectrometry. The mechanism of activation appears to be due at least in part to a lowering of the Km for the peptide substrate. Assessing the magnitude of the Km effect provides a means for tracking the potency of compounds with a single value instead using both the $EC_{50}$ and fold activation values. The $Km_{50}$ which is determined as described in this example is defined as the concentration of compound required to lower the Km for the Acetylated Peptide Substrate by 50%. Based on the previous example, the $Km_{50}$ for resveratrol is >100 uM.

Three test compounds were tested for their effect on the Km of SIRT1 for the acetylated peptide substrate and a $Km_{50}$ was determined. These three compounds and the results are shown in the Table 4.

mM KCl, 1 mM $MgCl_2$, 5 mM DTT, 0.05% BSA). Test compounds may be added to the reaction as described above. The SirT1 gene is cloned into a T7-promoter containing vector and transformed into BL21(DE3). After the 25 minute incubation with SIRT1, 10 μL of 10% formic acid is added to stop the reaction. Reactions are sealed and frozen for later mass spec analysis. Determination of the mass of the substrate peptide allows for precise determination of the degree of acetylation (i.e. starting material) as compared to deacetylated peptide (product).

For the mass spectrometry based assay, a control for inhibition of sirtuin activity is conducted by adding 1 μL of 500 mM nicotinamide as a negative control at the start of the

TABLE 4

$Km_{50}$ for Indicated Compounds.

| COMPOUND NO | STRUCTURE | KM50 (uM) |
| --- | --- | --- |
| 115 | 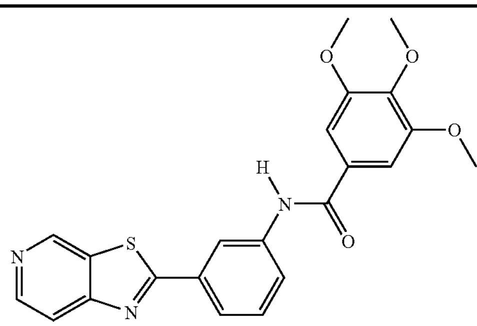 | 2.66 |
| 276 | 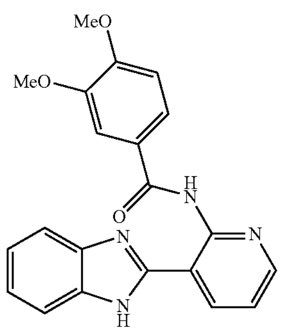 | 0.327 |
| 142 | 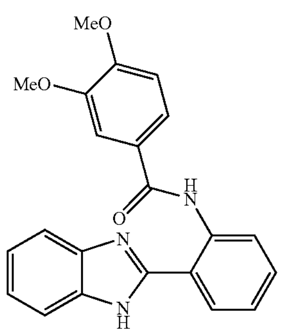 | 0.182 |

Example 7

Screening of Test Compounds using SIRT1 Mass Spectrometry Assay

The mass spectrometry assay is conducted as follows: 0.5 μM peptide substrate (SEQ ID NO: 34) and 120 μM βNAD⁺ is incubated with 10 nM SIRT1 for 25 minutes at 25° C. in a reaction buffer (50 mM Tris-acetate pH 8, 137 mM NaCl, 2.7 reaction (e.g., permits determination of maximum sirtuin inhibition). A control for activation of sirtuin activity is conducted using 10 nM of sirtuin protein, with 1 μL of DMSO in place of compound, to determine the amount of deacetylation of the substrate at a given timepoint within the linear range of the assay. This timepoint is the same as that used for test compounds and, within the linear range, the endpoint represents a change in velocity.

Sirtuin modulating compounds that activated SIRT1 were identified using the assay described above and are shown below in Table 5. The $ED_{50}$ values for the activating compounds in the mass spectromentry assay (MS) are represented by A ($ED_{50}$=<50 μM), B ($ED_{50}$=51-100 μM), C ($ED_{50}$=101-150 μM), and D ($ED_{50}$=>150 μM). NA means the compound was not active and NT means that the compound was not tested using the indicated assay. Fold activation, as determined by mass spectrometry (MS) is represented by A (Fold activation>250%), B (Fold Activation<250%), or C (no fold activation). The $ED_{50}$ of resveratrol for activation of SIRT1 is 16 μM and the fold activation of resveratrol for SIRT1 in the MS assay is approximately 200%.

TABLE 5

$ED_{50}$ and fold activation values for indicated compounds.

| COMPOUND NO | STRUCTURE | $ED_{50}$ MS ASSAY | FOLD ACTIVATION MS |
|---|---|---|---|
| 19 | 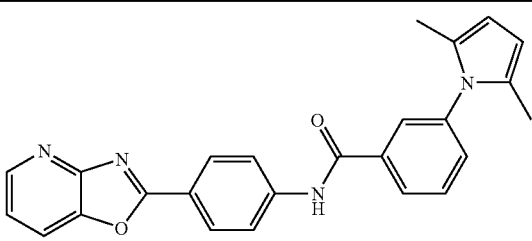 | D | C |
| 20 | 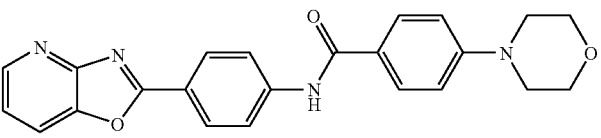 | D | C |
| 21 | 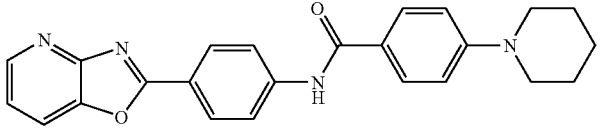 | D | C |
| 22 | 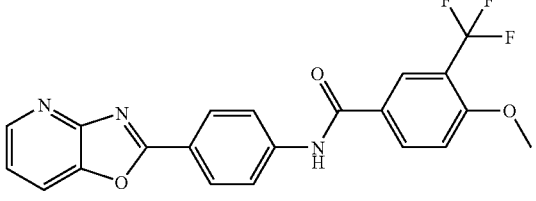 | D | C |
| 24 | 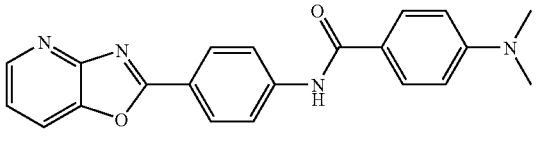 | D | C |
| 27 | 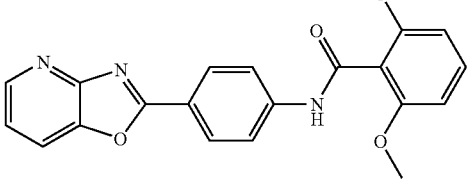 | D | C |
| 29 | 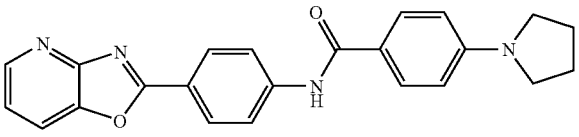 | D | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 31 | 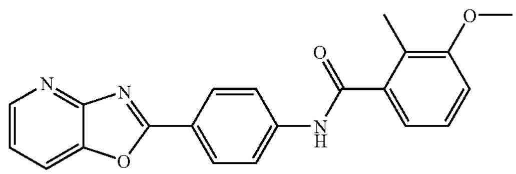 | D | C |
| 32 | 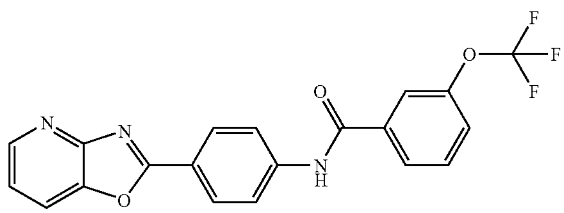 | D | C |
| 33 | 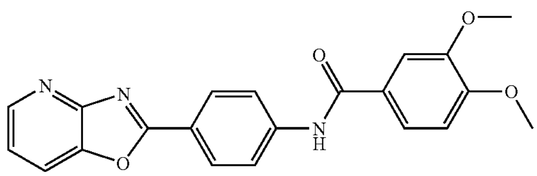 | D | C |
| 34 | 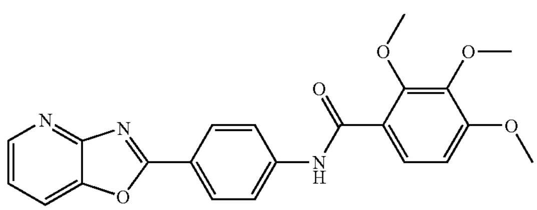 | D | C |
| 35 | 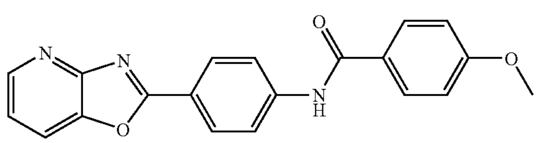 | D | C |
| 36 | 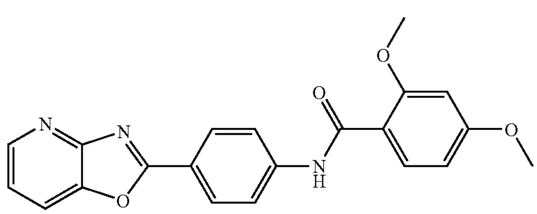 | D | C |
| 37 | 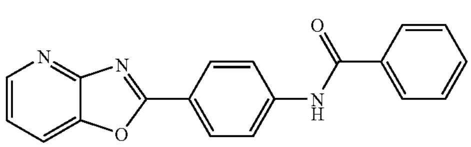 | D | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 38 | 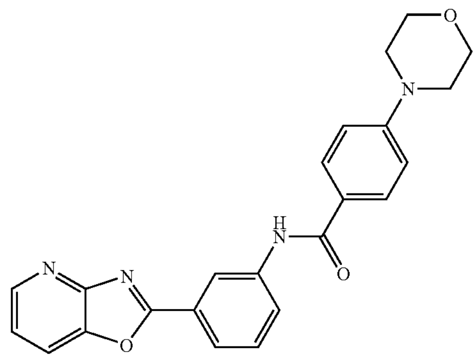 | D | C |
| 39 | 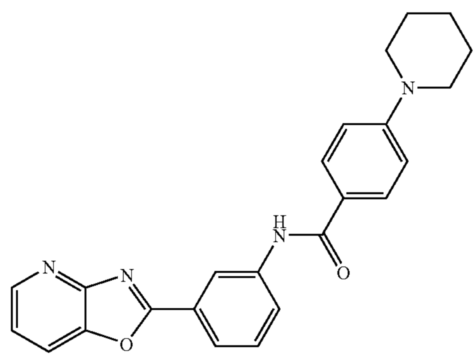 | D | C |
| 40 | 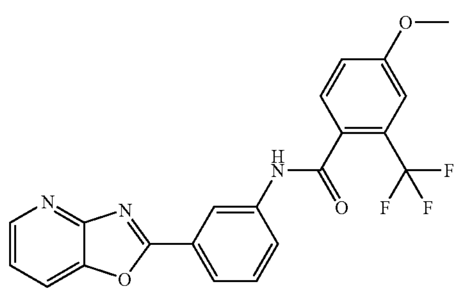 | D | C |
| 41 | 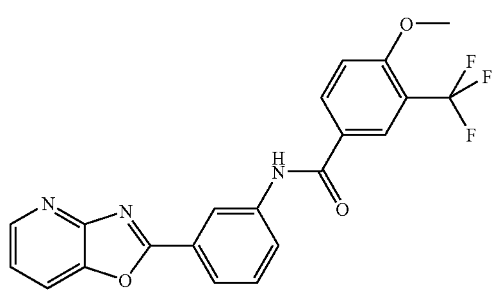 | D | C |
| 42 | 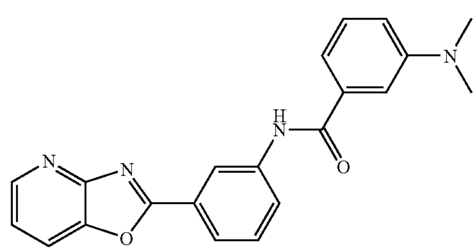 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 43 | 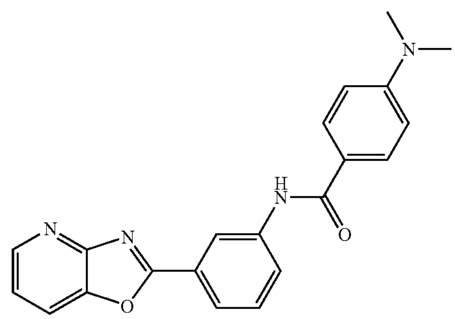 | A | B |
| 45 | 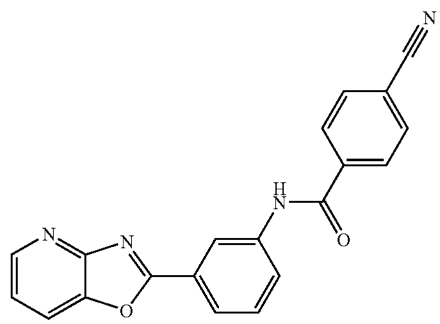 | D | C |
| 46 | 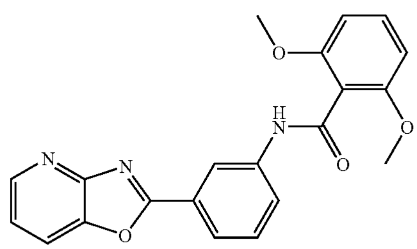 | D | C |
| 48 | 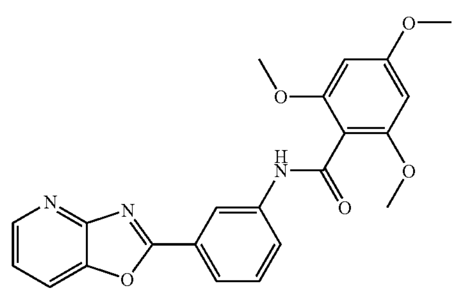 | D | C |
| 49 | 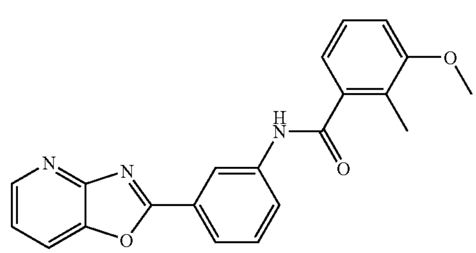 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 50 | 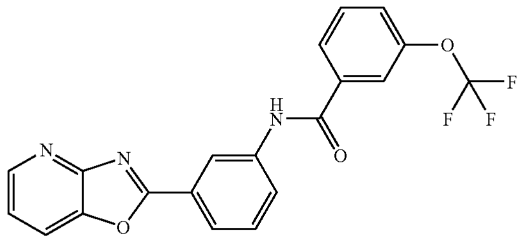 | D | |
| 51 | 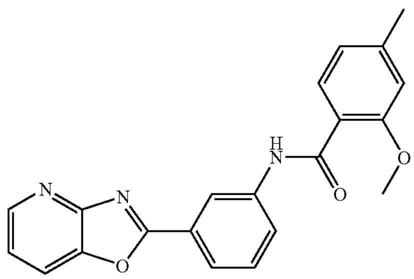 | A | B |
| 52 | 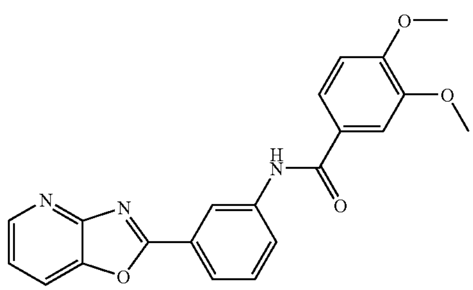 | A | B |
| 53 | 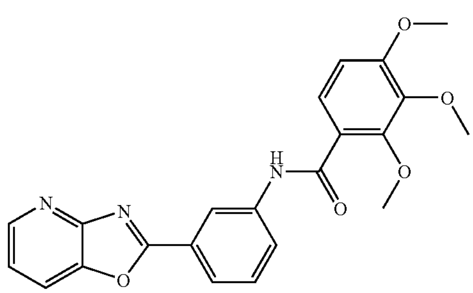 | D | C |
| 54 | 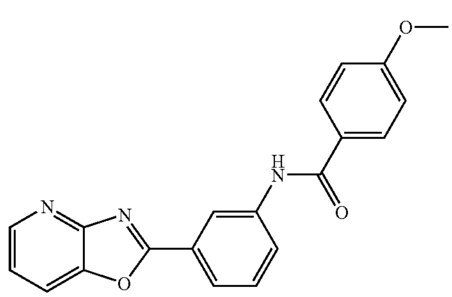 | D | NT |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 55 | 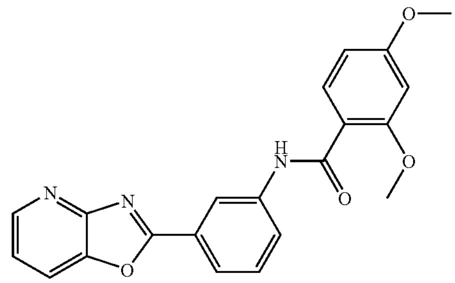 | A | B |
| 56 | 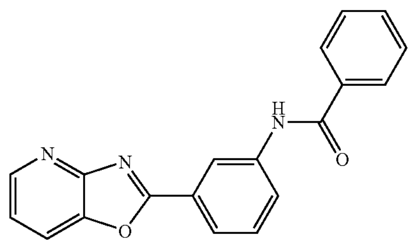 | A | B |
| 57 | 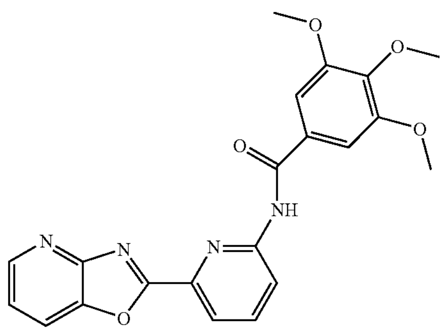 | A | NT |
| 60 | 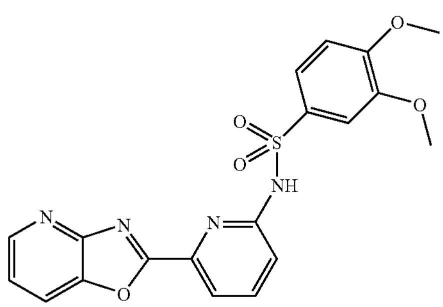 | A | NT |
| 63 | 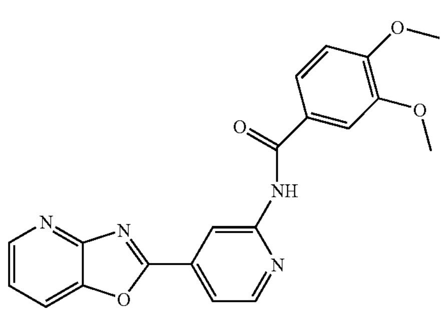 | A | NT |

TABLE 5-continued
ED$_{50}$ and fold activation values for indicated compounds.
| COMPOUND NO | STRUCTURE | ED$_{50}$ MS ASSAY | FOLD ACTIVATION MS |
|---|---|---|---|
| 64 | 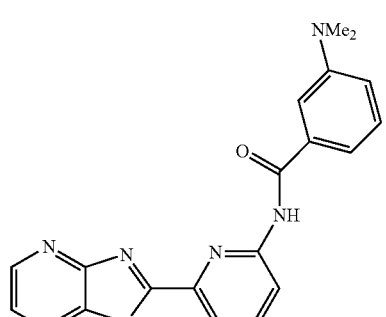 | A | NT |
| 66 | 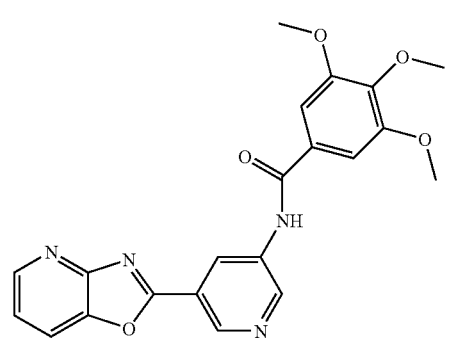 | A | NT |
| 67 | 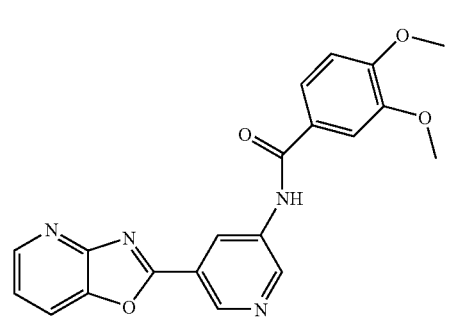 | A | NT |
| 68 | 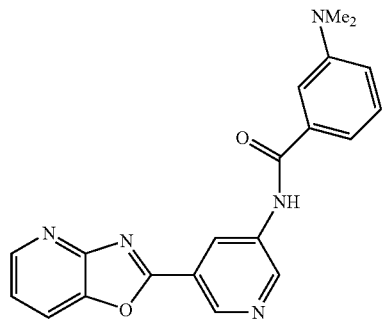 | A | NT |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 69 | (2,4-dimethoxybenzamide of oxazolo[4,5-b]pyridine-pyridinyl) | A | B |
| 70 | (4-NMe$_2$-benzamide of oxazolo[4,5-b]pyridine-pyridinyl) | A | B |
| 71 | (benzo[1,3]dioxol-5-yl urea of oxazolo[4,5-b]pyridine-pyridinyl) | A | B |
| 74 | (3,4-dimethoxybenzenesulfonamide of oxazolo[4,5-b]pyridine-pyridinyl) | D | C |
| 75 | (3,4,5-trimethoxybenzamide of oxazolo[4,5-b]pyridine-pyridinyl) | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 76 | 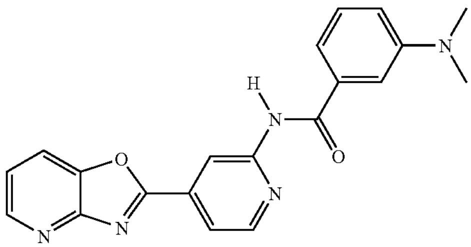 | A | B |
| 77 | 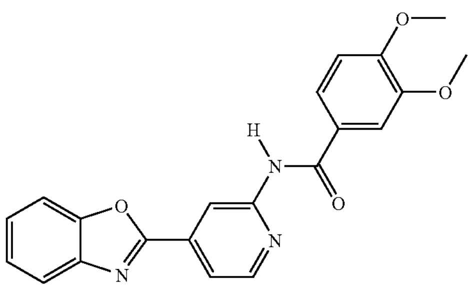 | A | B |
| 79 | 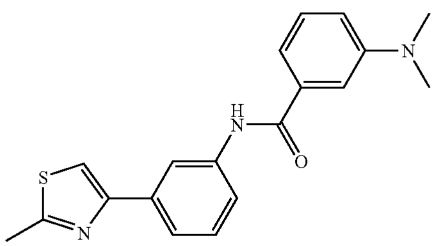 | D | C |
| 80 | 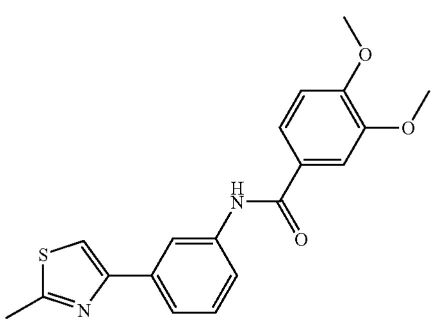 | A | B |
| 81 | 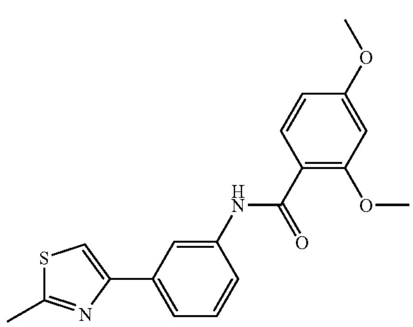 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 82 | 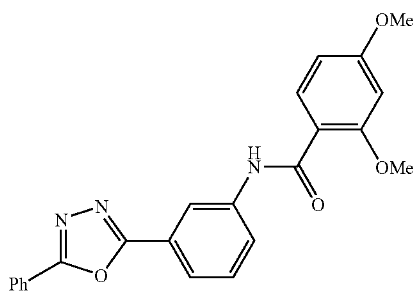 | C | NT |
| 83 | 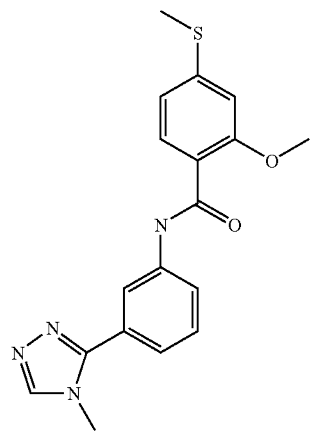 | A | B |
| 84 | 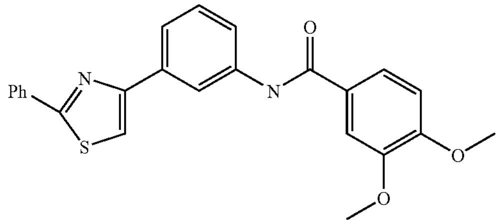 | A | B |
| 85 | 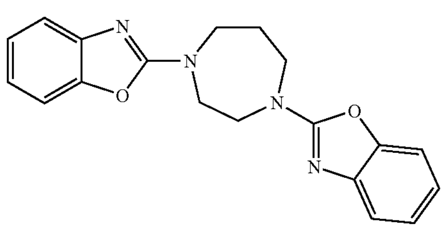 | D | C |
| 86 | 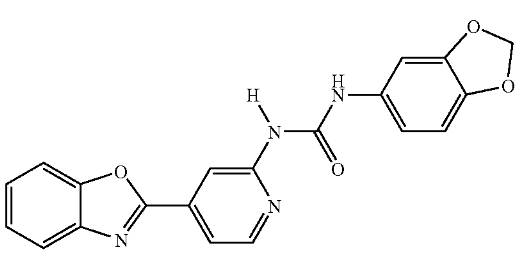 | D | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 87 | 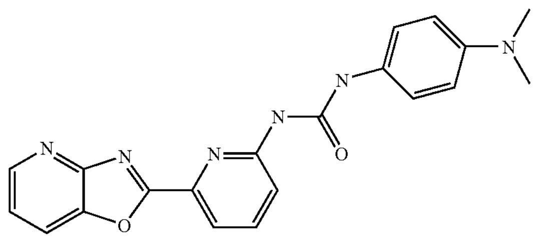 | D | C |
| 88 | 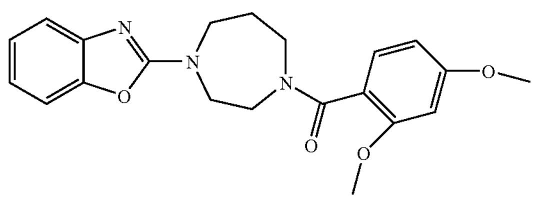 | D | C |
| 89 | 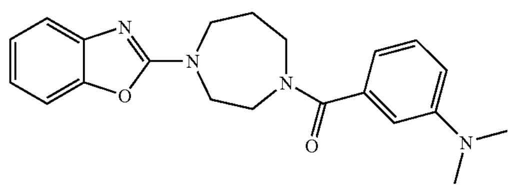 | D | C |
| 91 | 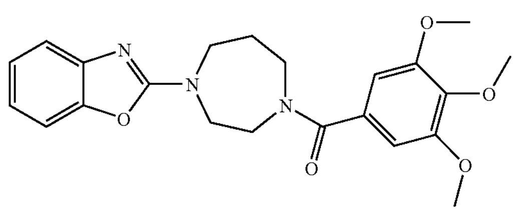 | D | C |
| 92 | 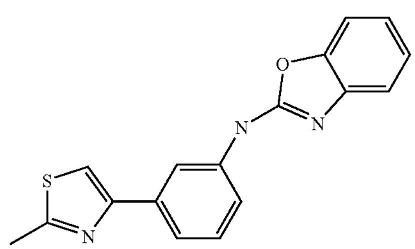 | A | B |
| 93 | 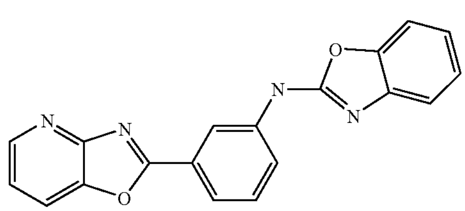 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 94 | 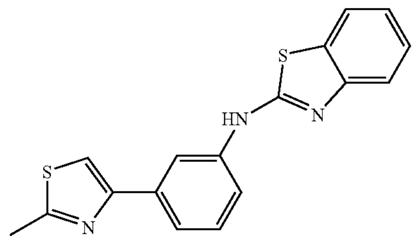 | A | B |
| 95 | 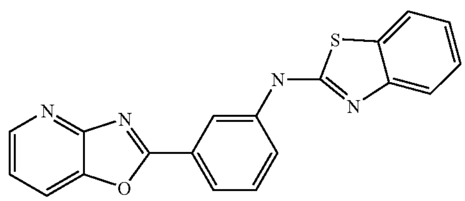 | A | B |
| 96 | 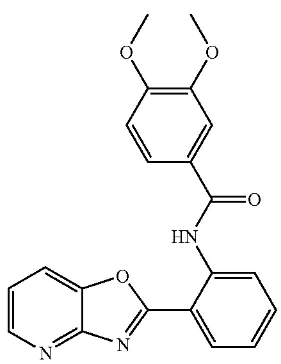 | A | B |
| 97 | 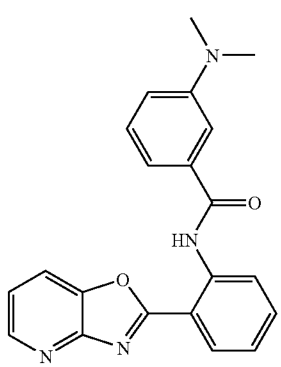 | A | B |

TABLE 5-continued
ED$_{50}$ and fold activation values for indicated compounds.
| COMPOUND NO | STRUCTURE | ED$_{50}$ MS ASSAY | FOLD ACTIVATION MS |
|---|---|---|---|
| 98 | 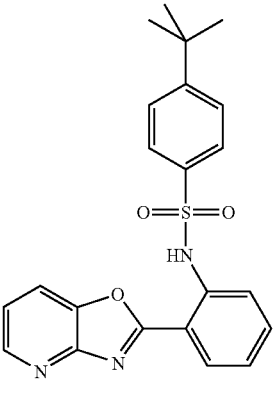 | D | C |
| 99 | 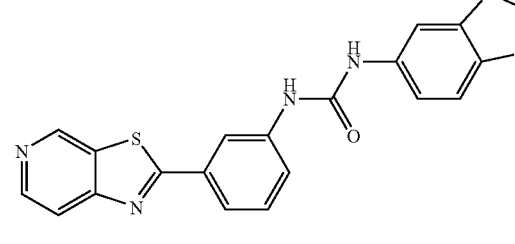 | A | A |
| 100 | 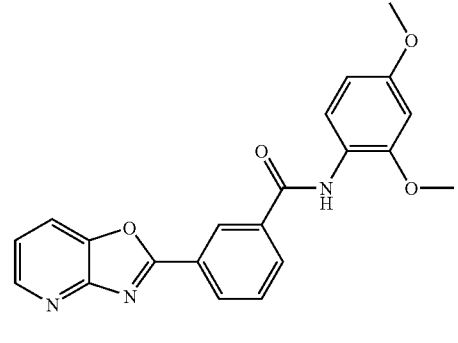 | A | B |
| 101 | 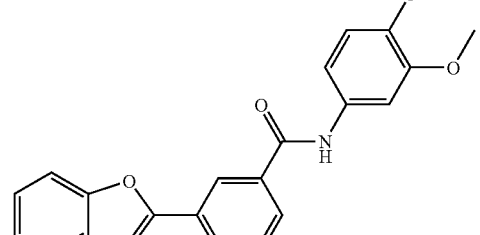 | A | A |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 102 | 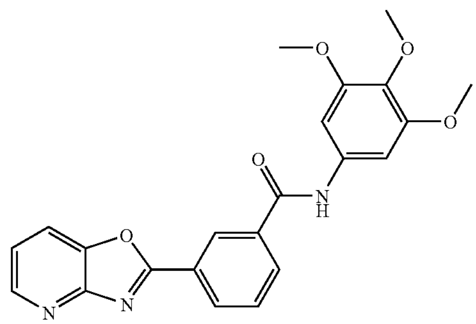 | A | A |
| 103 | 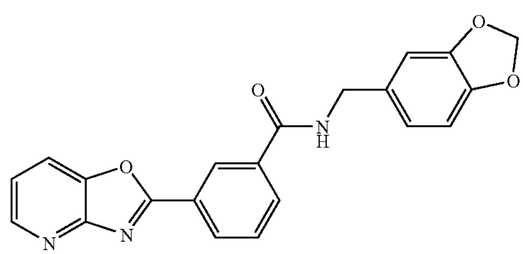 | D | C |
| 104 | 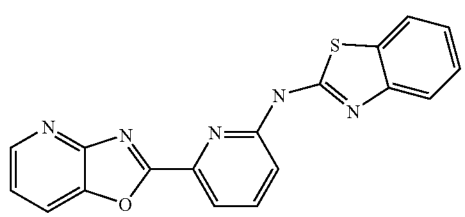 | A | B |
| 105 | 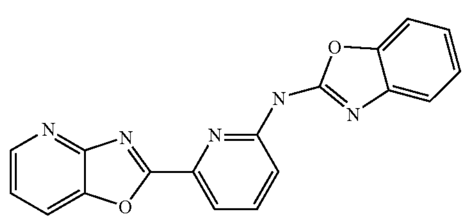 | A | B |
| 106 | 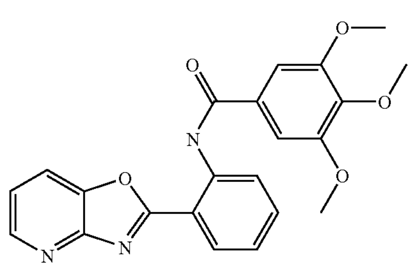 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 107 | 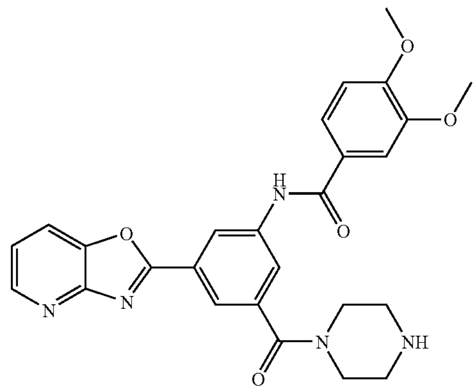 | A | B |
| 108 | 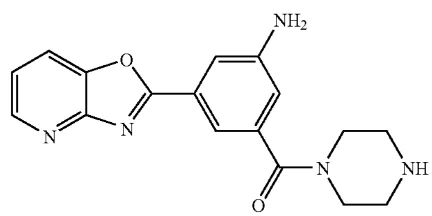 | NA | NT |
| 109 | 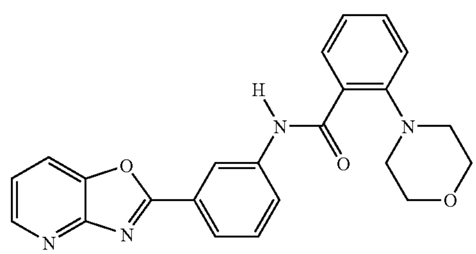 | A | B |
| 110 | 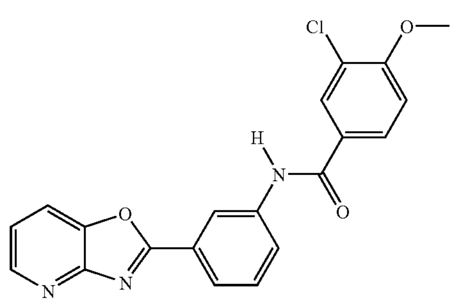 | C | NT |
| 111 | 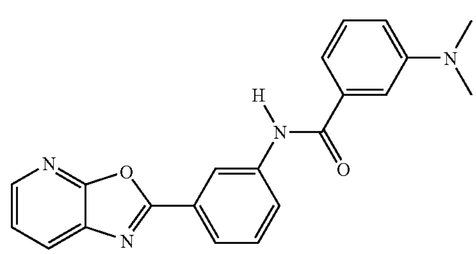 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 112 | ![structure] | A | B |
| 113 | ![structure] | A | B |
| 114 | ![structure] | A | A |
| 115 | ![structure] | A | A |
| 116 | ![structure] | C | NT |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 117 | 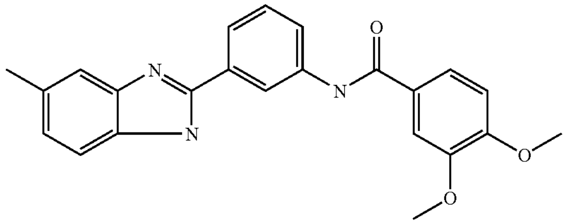 | A | A |
| 118 | 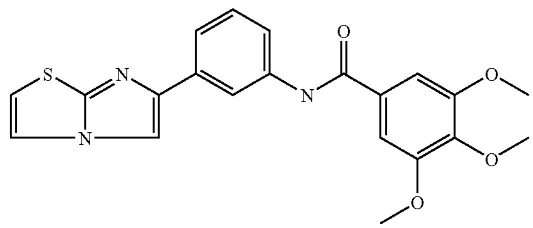 | A | A |
| 119 | 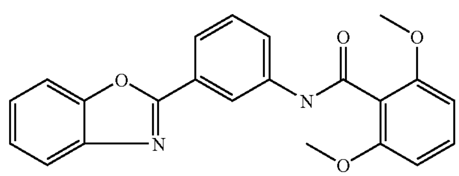 | A | B |
| 121 | 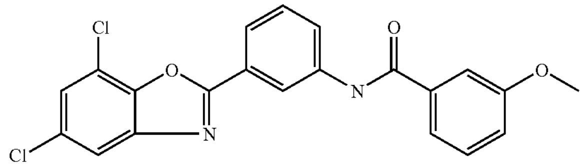 | D | C |
| 122 | 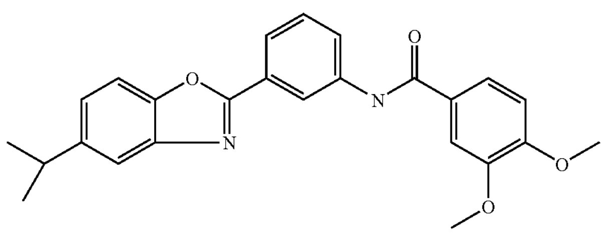 | C | NT |
| 124 | 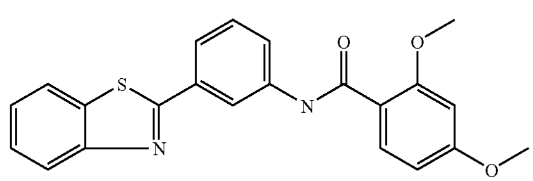 | A | B |
| 125 | 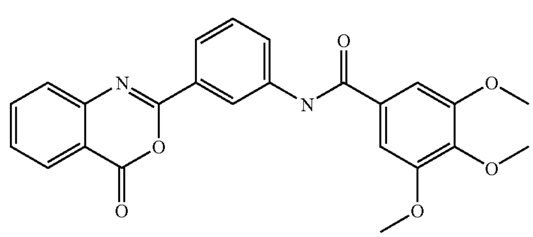 | B | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 126 | 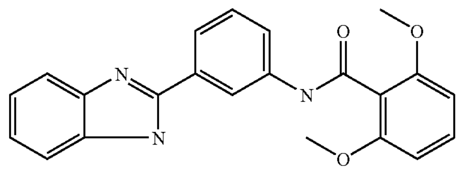 | A | B |
| 127 | 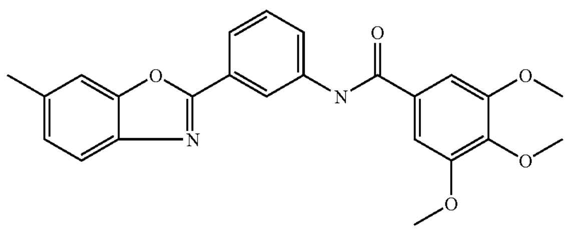 | A | A |
| 128 | 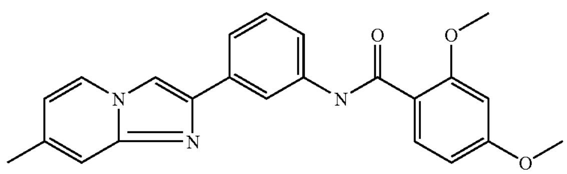 | A | B |
| 129 | 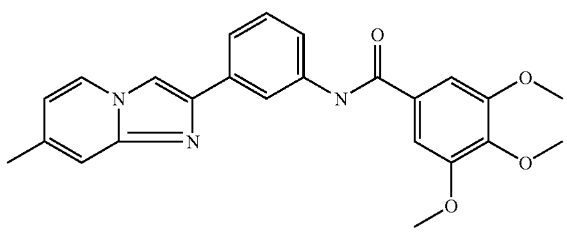 | A | A |
| 130 | 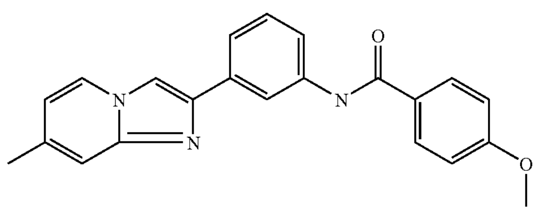 | A | B |
| 131 | 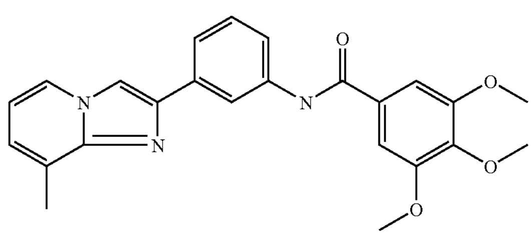 | A | A |
| 132 | 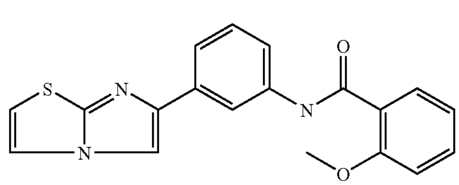 | A | A |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 133 | 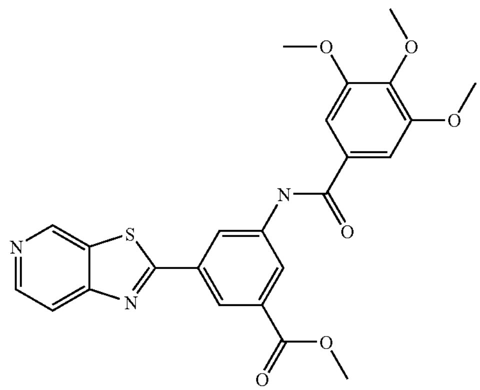 | A | B |
| 134 | 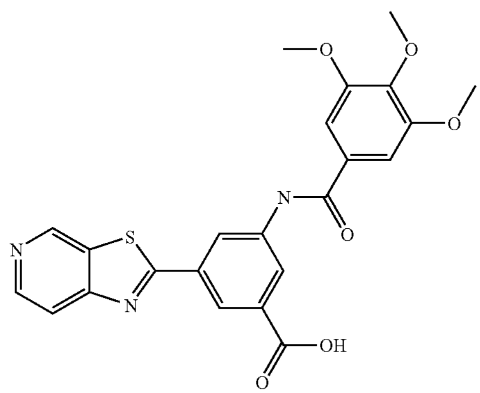 | A | B |
| 135 | 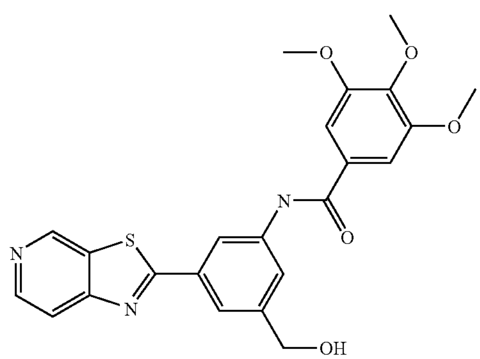 | A | B |
| 136 | 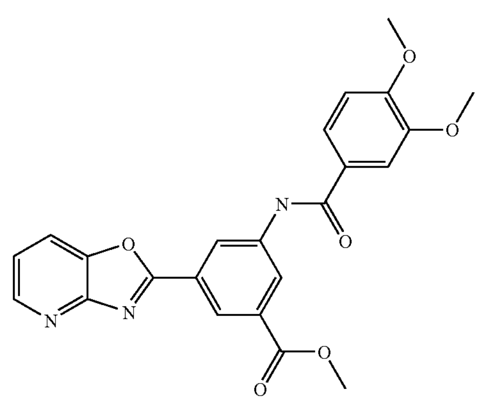 | D | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 137 | 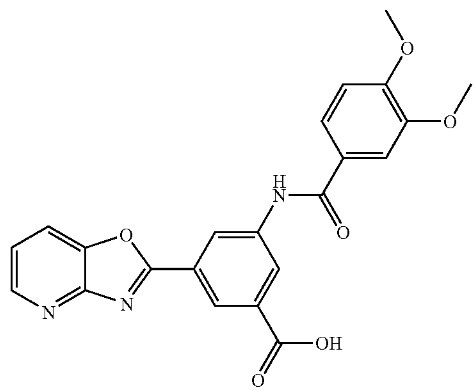 | D | NT |
| 138 | 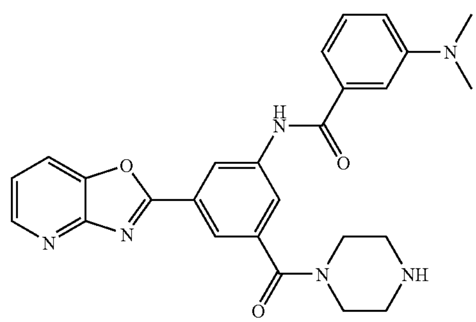 | A | B |
| 139 | 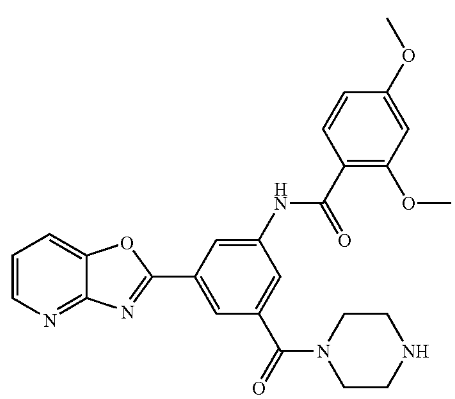 | A | B |
| 140 | 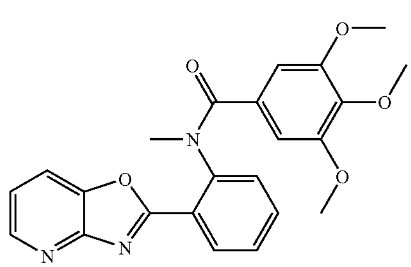 | D | NT |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 141 | 3,5-dimethoxy-N-(2-(1H-benzimidazol-2-yl)phenyl)benzamide | A | B |
| 142 | 3,4-dimethoxy-N-(2-(1H-benzimidazol-2-yl)phenyl)benzamide | A | A |
| 143 | N-(2-(1H-benzimidazol-2-yl)phenyl)-3,4-dimethoxybenzenesulfonamide | D | NT |
| 144 | 3,4,5-trimethoxy-N-(3-(benzo[d]thiazol-2-yl)thiophen-2-yl)benzamide | D | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 145 | 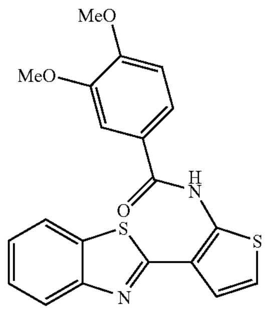 | A | B |
| 146 | 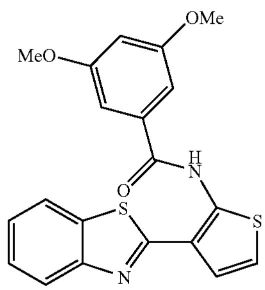 | A | B |
| 147 | 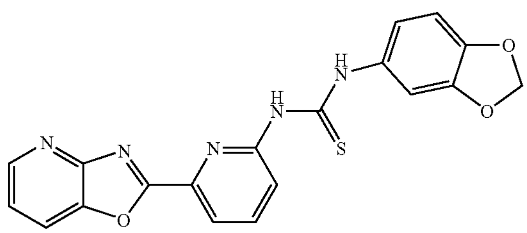 | D | NT |
| 148 | 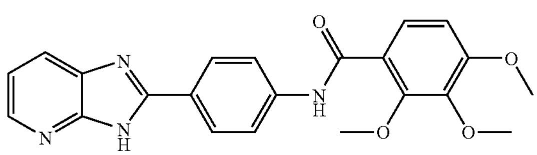 | D | NT |
| 149 | 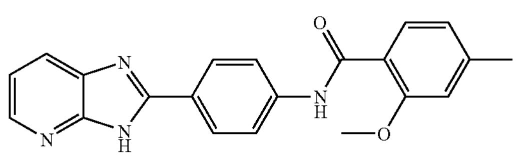 | A | B |
| 150 | 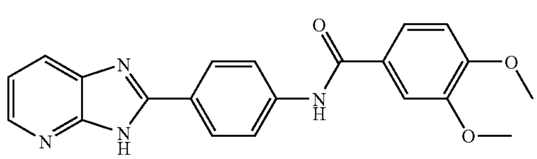 | A | B |
| 151 | 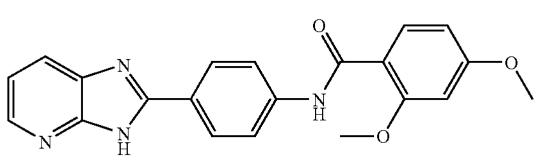 | D | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 152 | 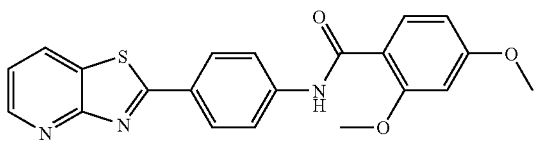 | D | C |
| 153 | 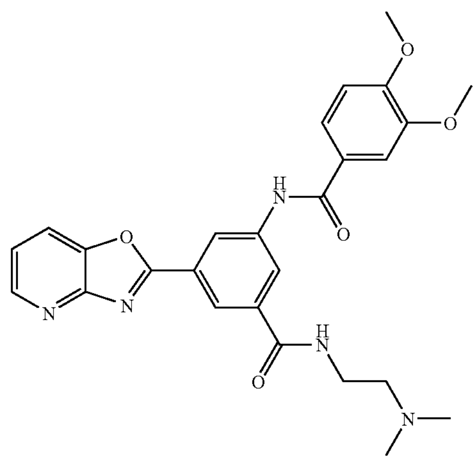 | A | B |
| 154 | 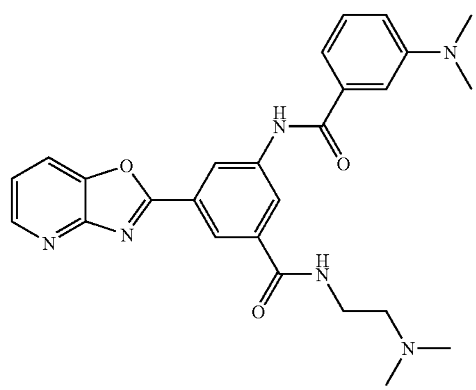 | C | A |
| 155 | 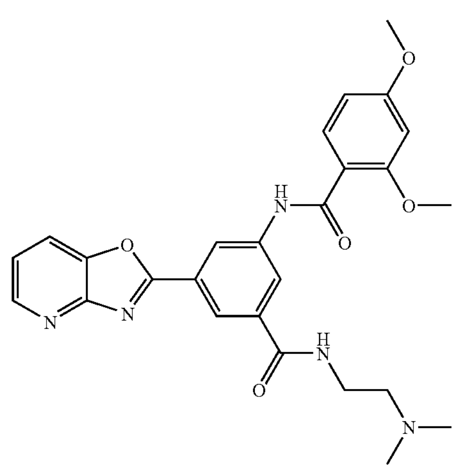 | A | B |

TABLE 5-continued
ED$_{50}$ and fold activation values for indicated compounds.
| COMPOUND NO | STRUCTURE | ED$_{50}$ MS ASSAY | FOLD ACTIVATION MS |
|---|---|---|---|
| 156 | 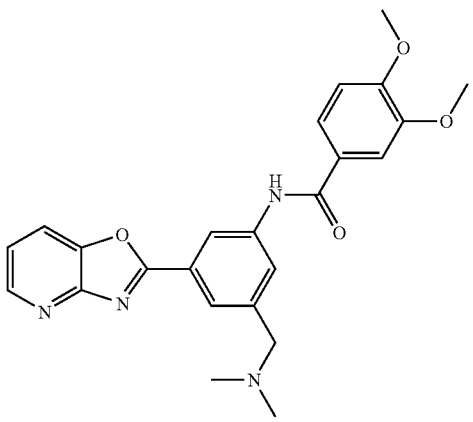 | A | B |
| 157 | 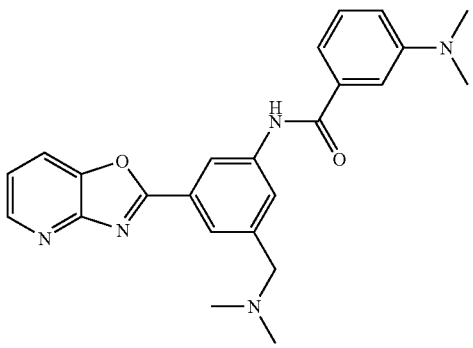 | D | B |
| 158 | 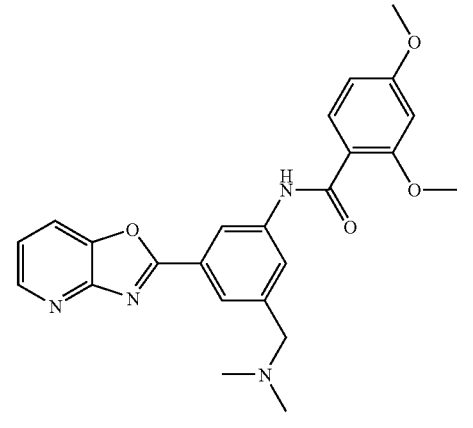 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 159 | 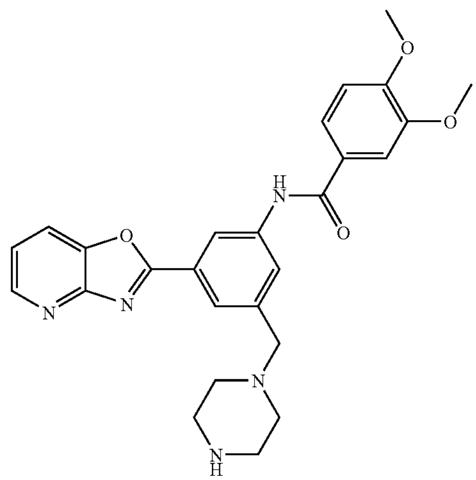 | A | B |
| 160 | 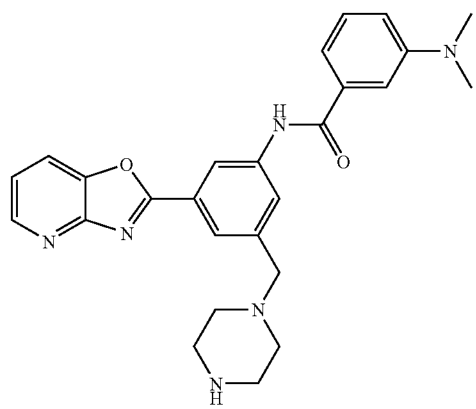 | B | A |
| 161 | 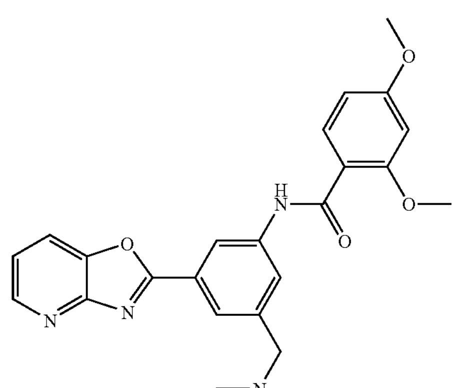 | A | A |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 162 | 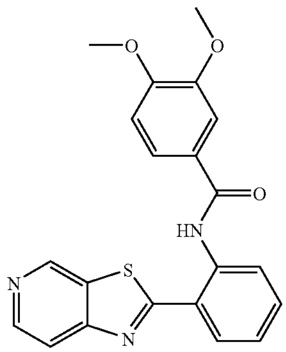 | A | B |
| 163 | 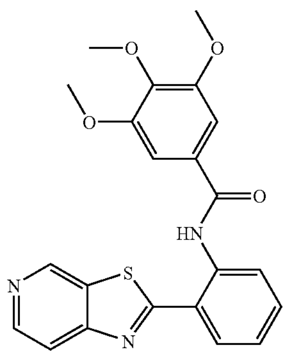 | A | B |
| 164 | 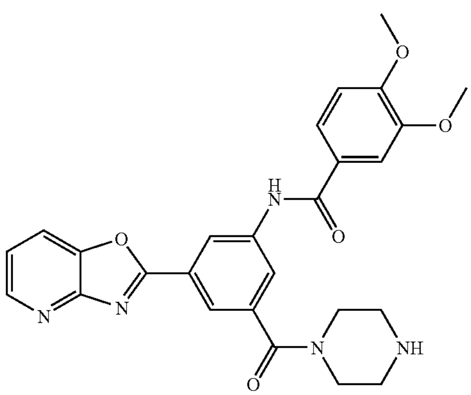 | A | B |
| 165 | 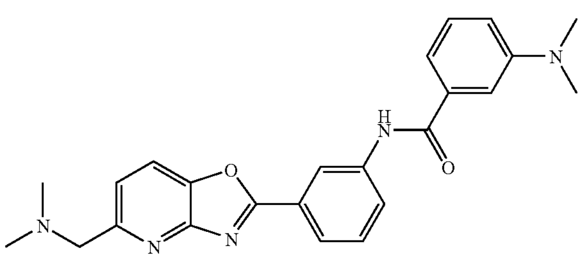 | D | A |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 166 | 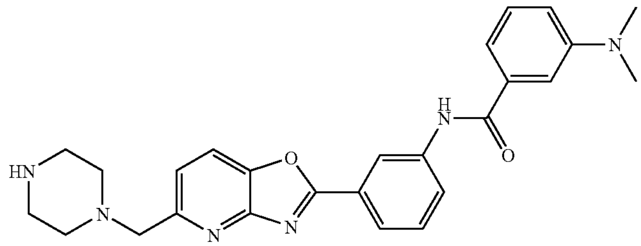 | A | B |
| 167 | 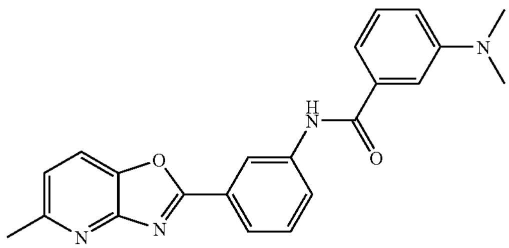 | A | B |
| 168 | 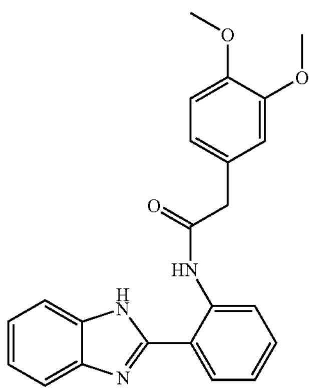 | NA | C |
| 169 | 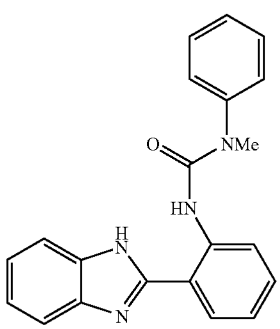 | A | B |
| 171 | 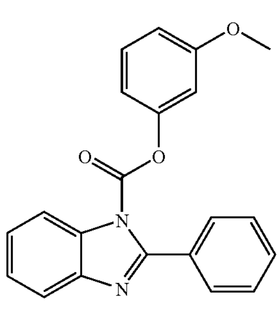 | NA | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 172 | 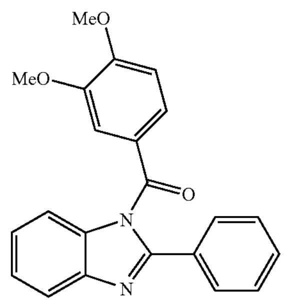 | NA | C |
| 173 | 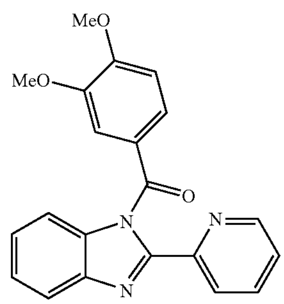 | NA | C |
| 174 | 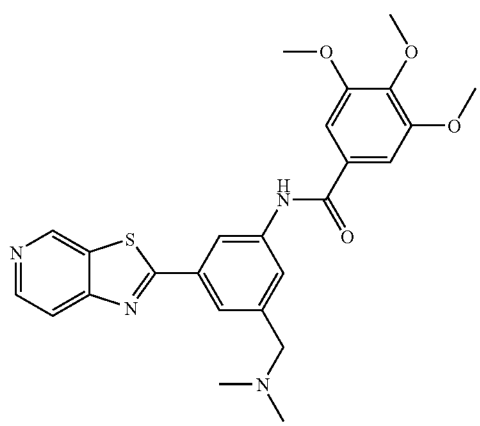 | B | A |
| 175 | 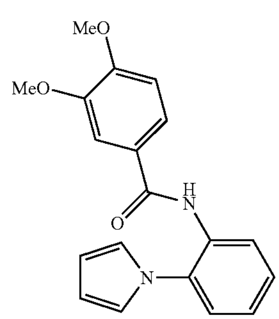 | B | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 176 | 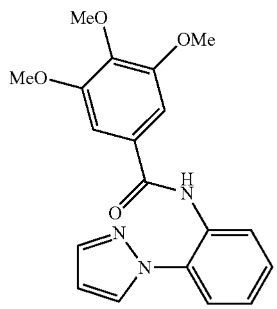 | B | B |
| 177 | 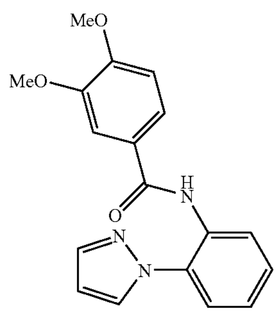 | D | B |
| 178 | 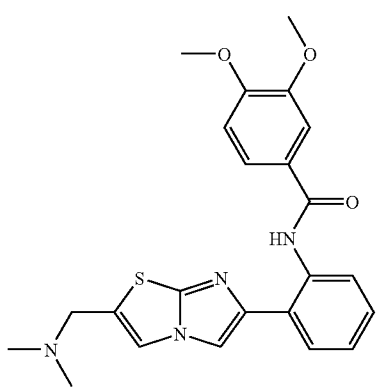 | A | A |
| 179 | 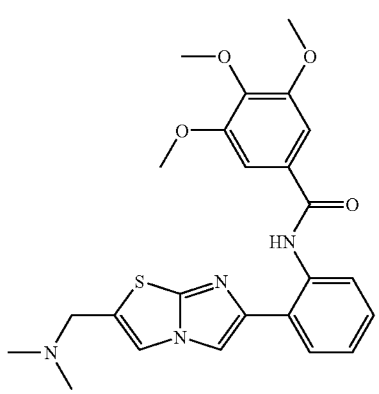 | A | A |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 180 | 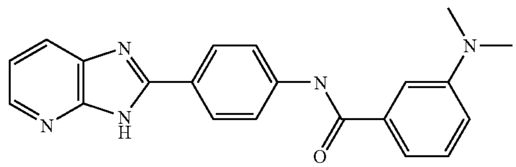 | A | B |
| 181 | 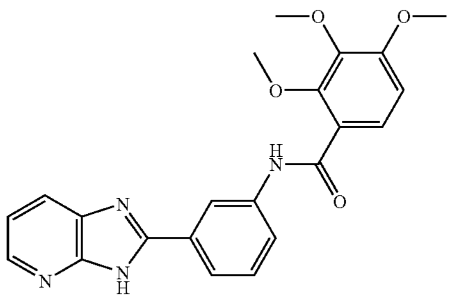 | A | A |
| 182 | 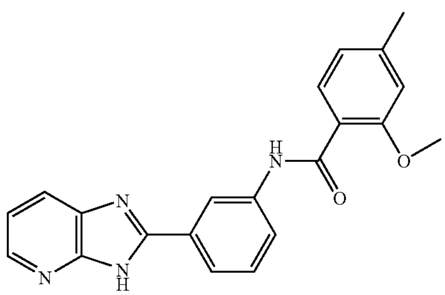 | A | A |
| 183 | 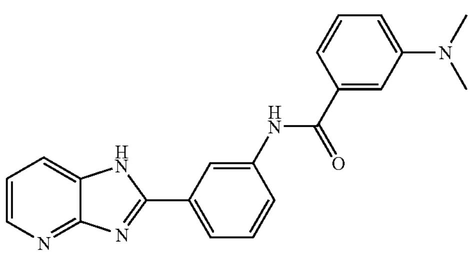 | A | A |
| 184 | 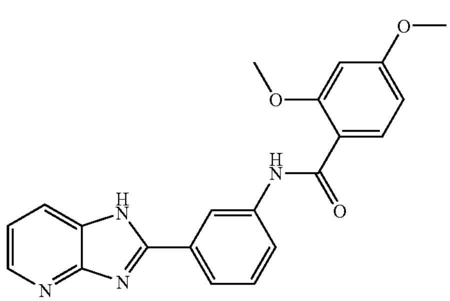 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 185 | 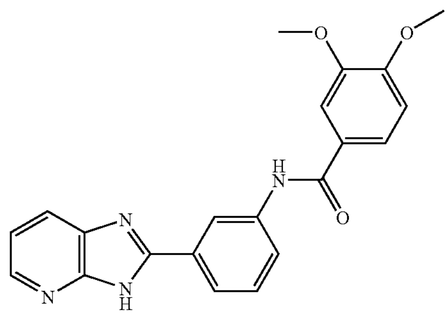 | A | A |
| 186 | 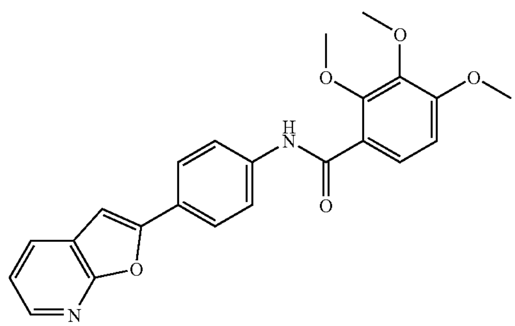 | NA | C |
| 187 | 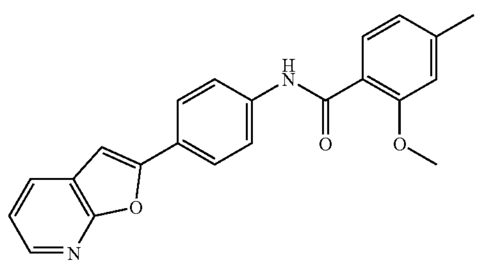 | A | B |
| 188 | 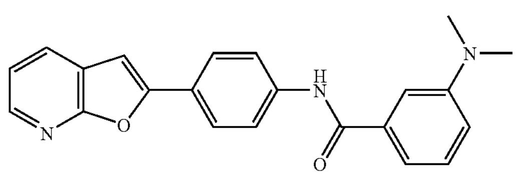 | NA | C |
| 189 | 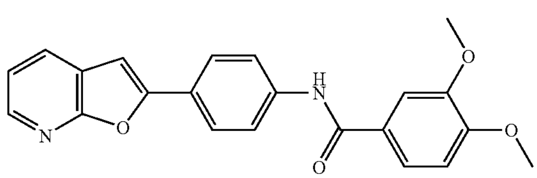 | NA | C |
| 190 | 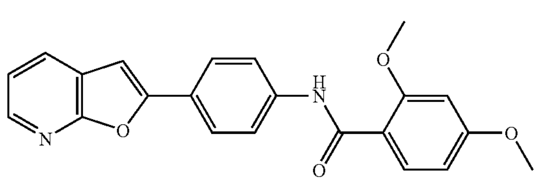 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 191 | 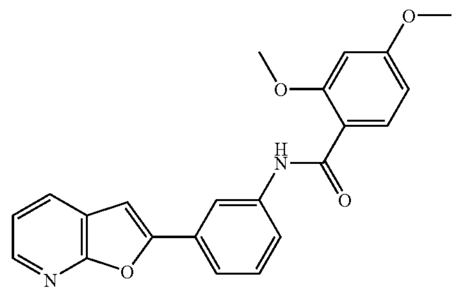 | A | B |
| 192 | 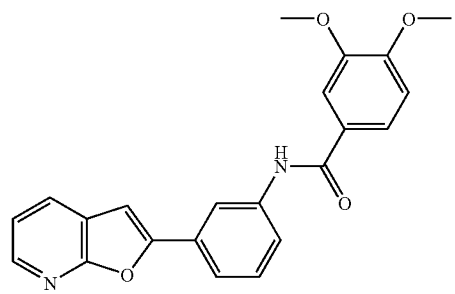 | A | B |
| 193 | 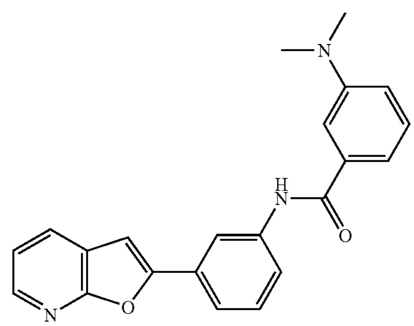 | NA | C |
| 194 | 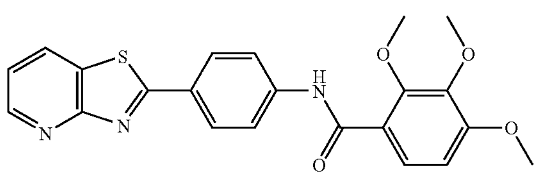 | NA | C |
| 195 | 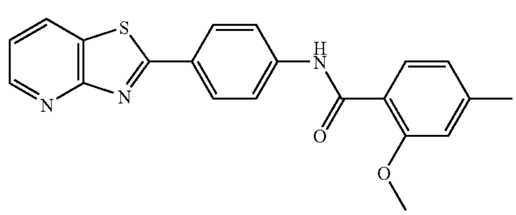 | NA | C |
| 196 | 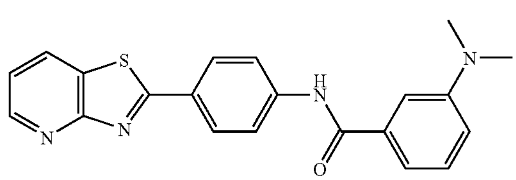 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 197 | 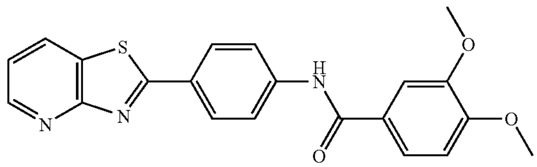 | A | B |
| 198 | 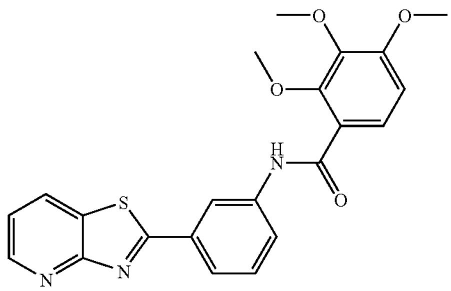 | A | B |
| 199 | 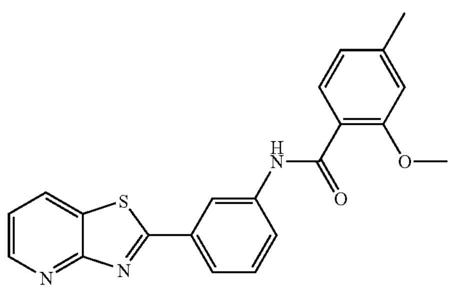 | A | B |
| 200 | 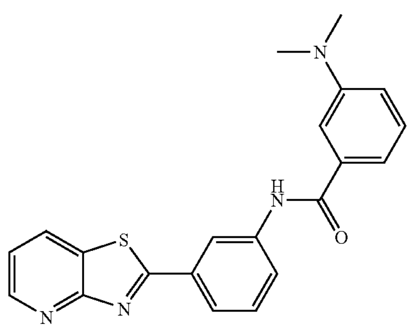 | A | B |
| 201 | 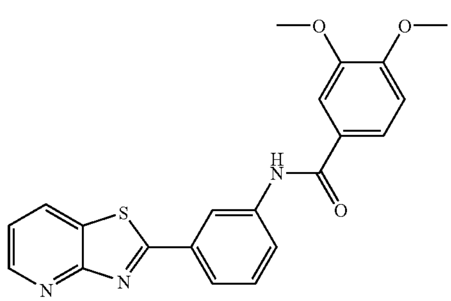 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 202 | 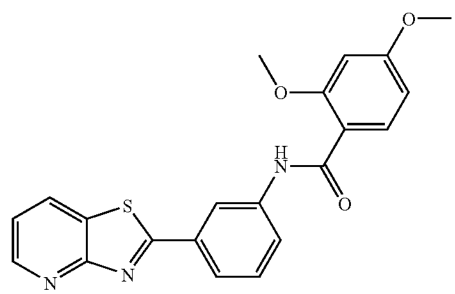 | A | B |
| 203 | 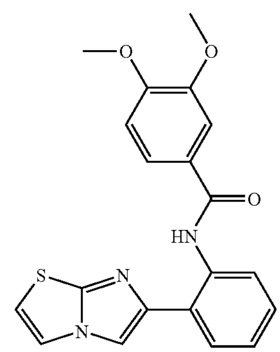 | A | B |
| 204 | 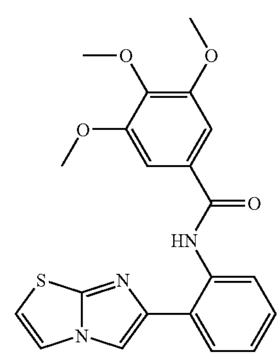 | A | A |
| 205 | 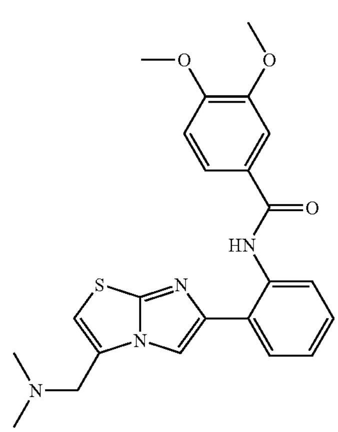 | A | A |

TABLE 5-continued
ED$_{50}$ and fold activation values for indicated compounds.
| COMPOUND NO | STRUCTURE | ED$_{50}$ MS ASSAY | FOLD ACTIVATION MS |
|---|---|---|---|
| 206 | 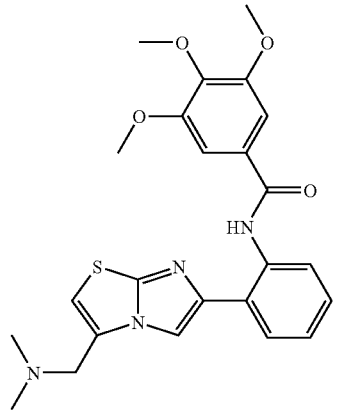 | A | A |
| 207 | 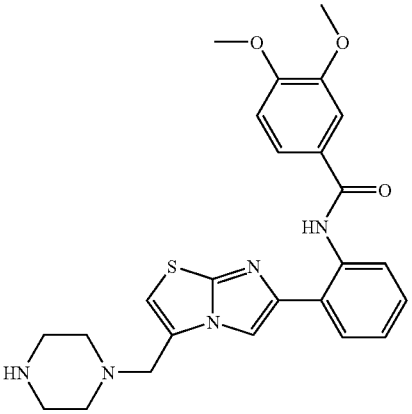 | A | A |
| 208 | 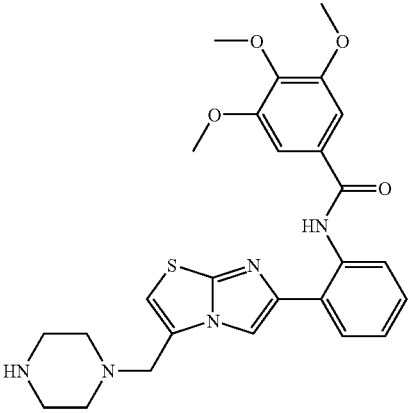 | A | A |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 209 | 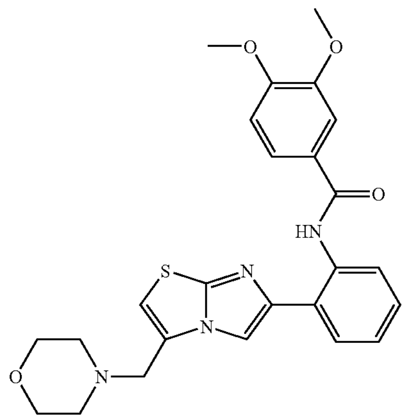 | A | A |
| 210 | 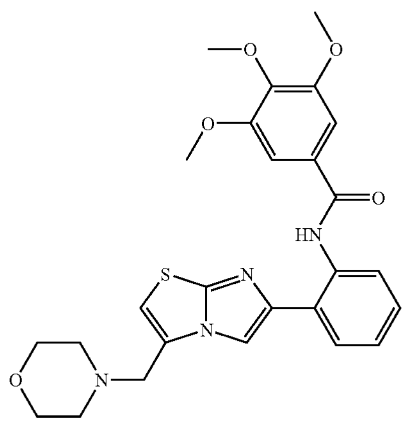 | A | B |
| 211 | 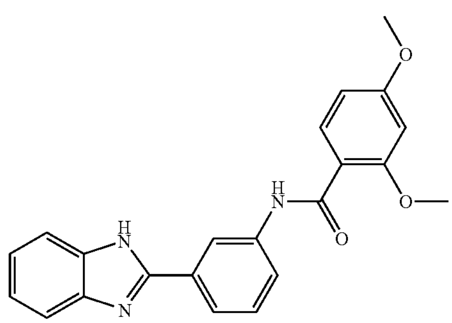 | A | B |
| 212 | 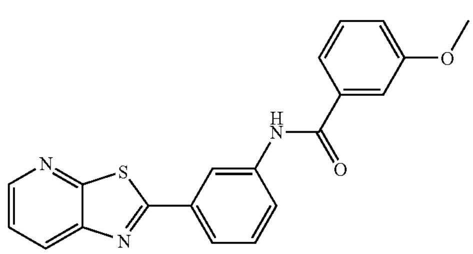 | A | B |

TABLE 5-continued

ED₅₀ and fold activation values for indicated compounds.

| COMPOUND NO | STRUCTURE | ED₅₀ MS ASSAY | FOLD ACTIVATION MS |
|---|---|---|---|
| 213 | 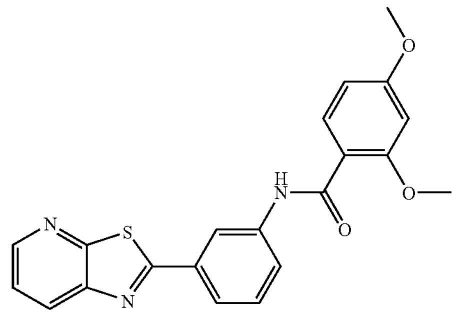 | A | B |
| 214 | 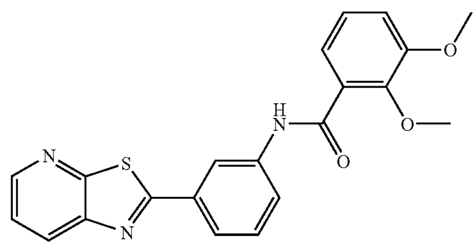 | A | B |
| 215 | 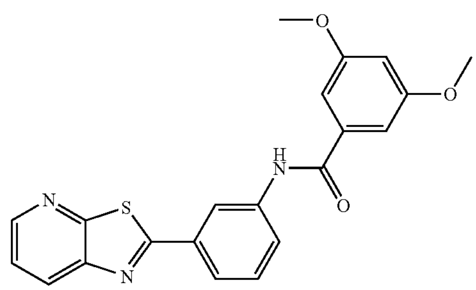 | A | B |
| 216 | 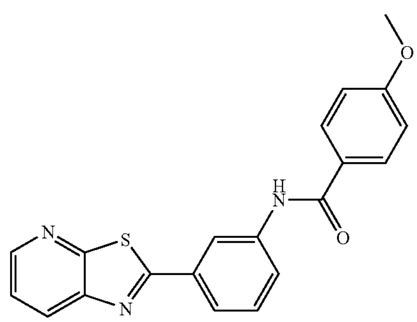 | A | B |
| 217 | 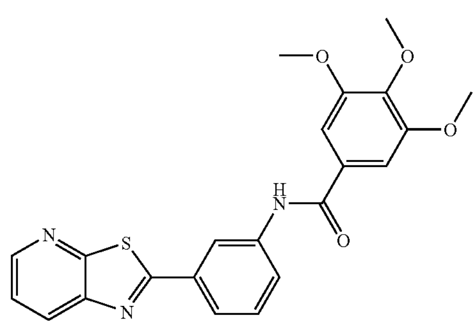 | A | A |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 218 | 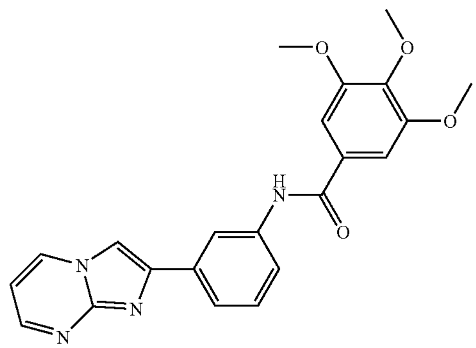 | A | A |
| 219 | 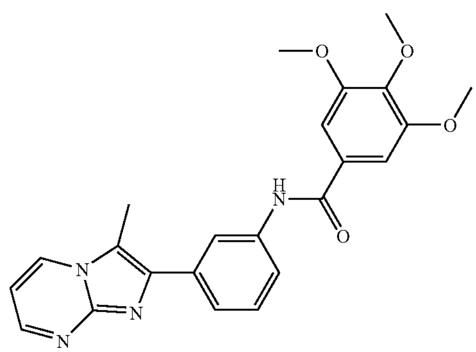 | A | A |
| 220 | 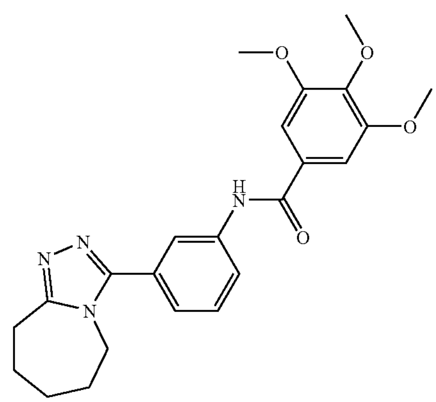 | NA | C |
| 221 | 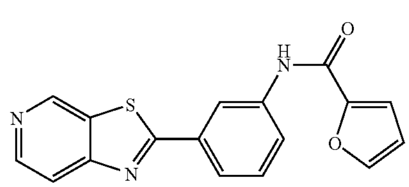 | A | B |
| 222 | 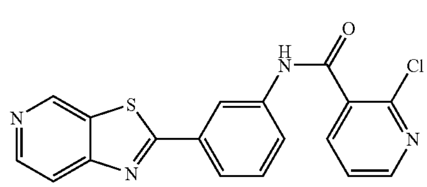 | A | B |

TABLE 5-continued
ED$_{50}$ and fold activation values for indicated compounds.
| COMPOUND NO | STRUCTURE | ED$_{50}$ MS ASSAY | FOLD ACTIVATION MS |
|---|---|---|---|
| 223 | 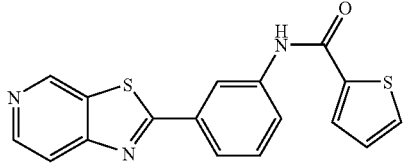 | A | B |
| 225 | 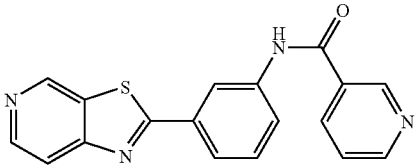 | NA | C |
| 227 | 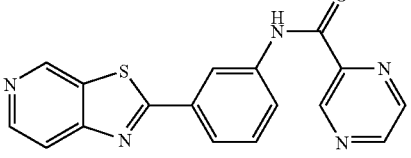 | NA | C |
| 228 | 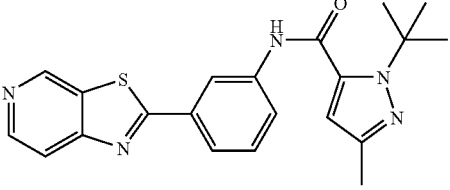 | A | A |
| 229 | 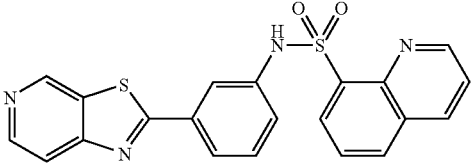 | NA | C |
| 230 | 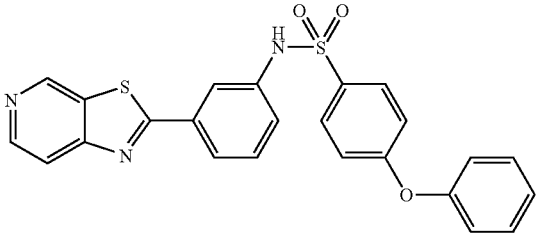 | NA | C |
| 231 | 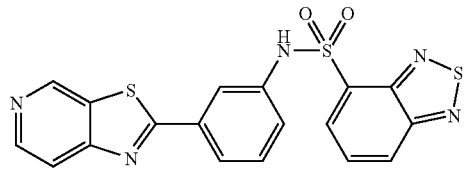 | NA | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 232 | 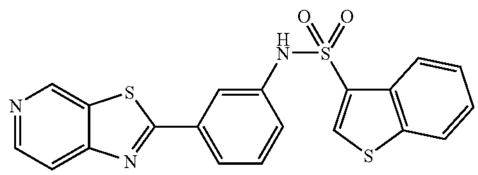 | NA | C |
| 234 | 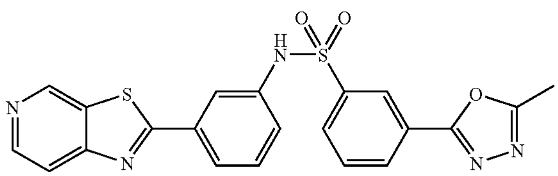 | NA | C |
| 235 | 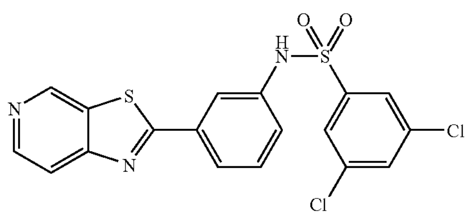 | NA | C |
| 236 | 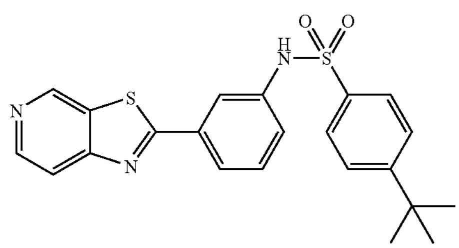 | NA | C |
| 237 | 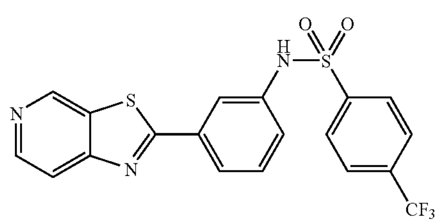 | NA | C |
| 238 | 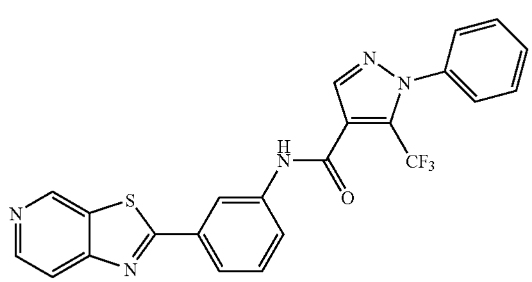 | A | B |

TABLE 5-continued

ED₅₀ and fold activation values for indicated compounds.

| COMPOUND NO | STRUCTURE | ED₅₀ MS ASSAY | FOLD ACTIVATION MS |
|---|---|---|---|
| 239 | 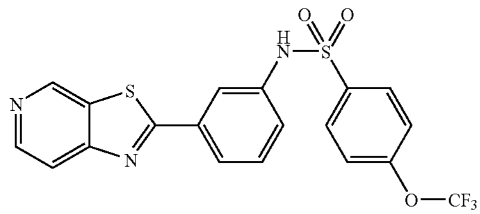 | A | B |
| 240 | 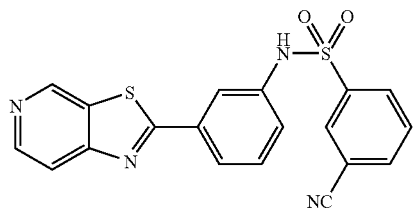 | NA | C |
| 241 | 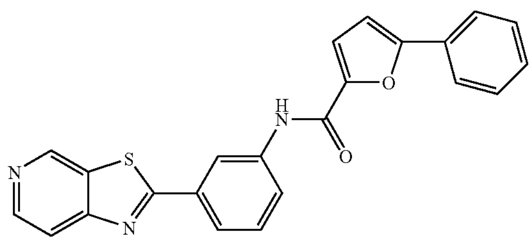 | A | B |
| 244 | 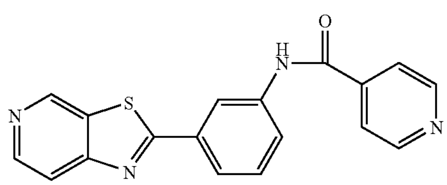 | NA | C |
| 245 | 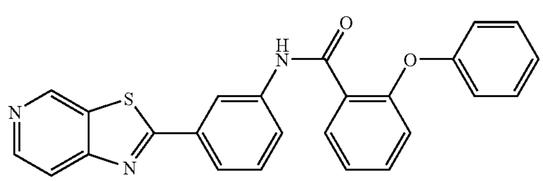 | A | B |
| 246 | 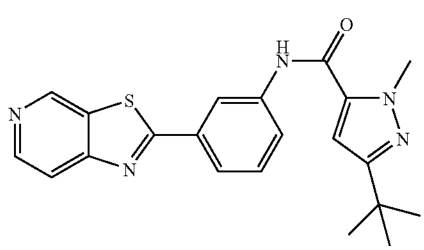 | A | B |
| 247 | 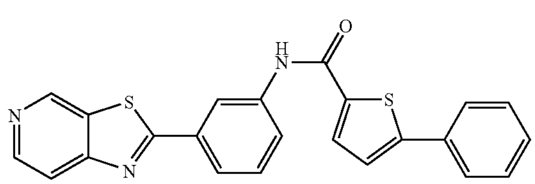 | NA | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 248 | 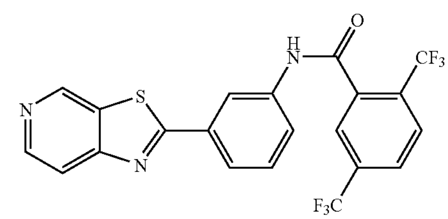 | A | B |
| 250 | 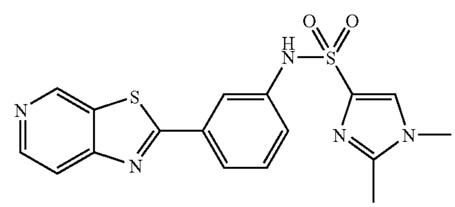 | NA | C |
| 251 | 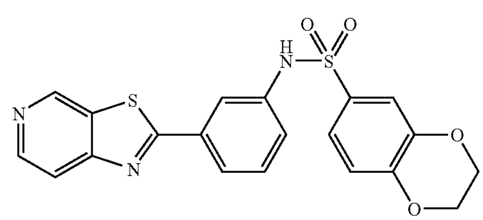 | NA | C |
| 252 | 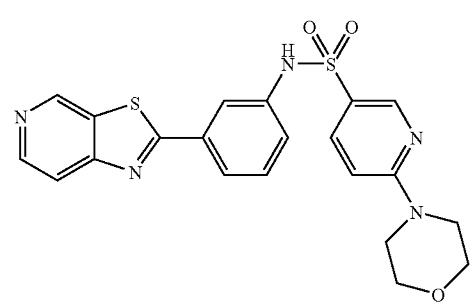 | NA | C |
| 253 | 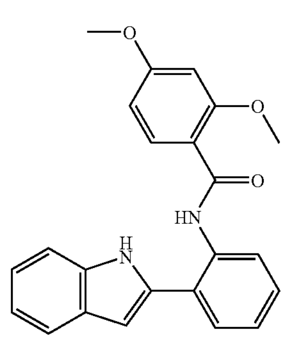 | NA | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 254 | 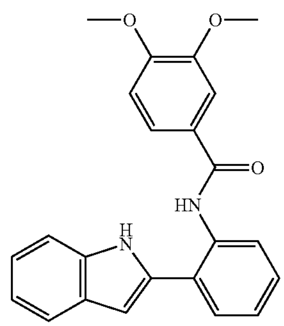 | A | B |
| 255 | 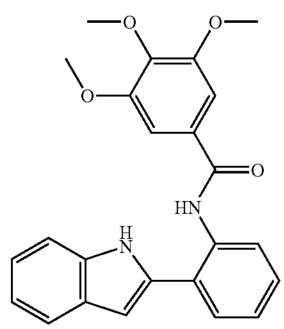 | A | B |
| 256 | 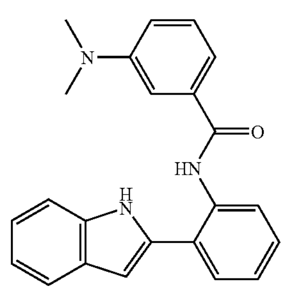 | NA | C |
| 257 | 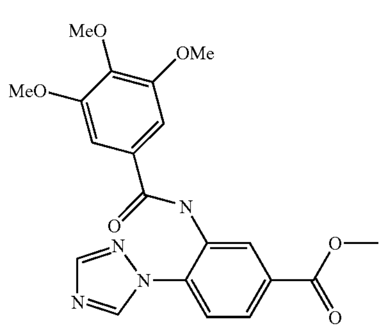 | NA | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 258 | 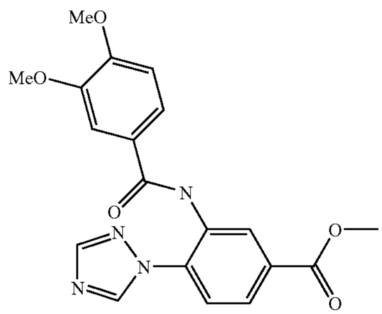 | A | B |
| 259 | 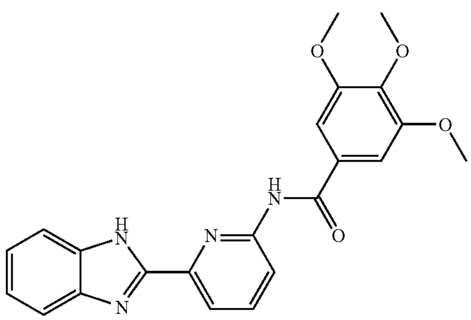 | A | A |
| 260 | 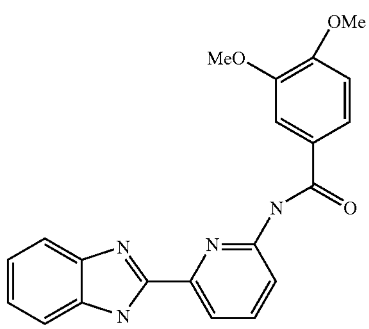 | A | A |
| 261 | 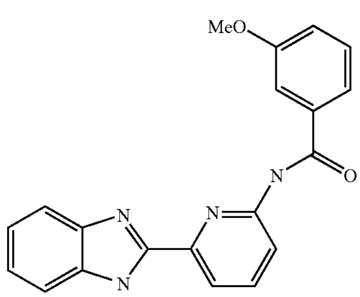 | A | A |
| 262 | 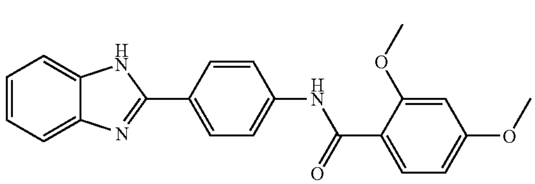 | A | B |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 263 | 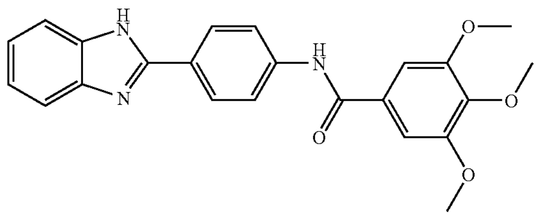 | A | B |
| 264 | 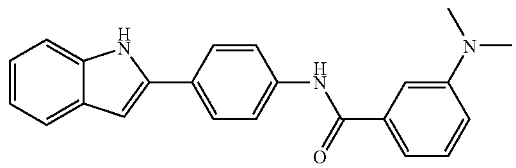 | A | B |
| 265 | 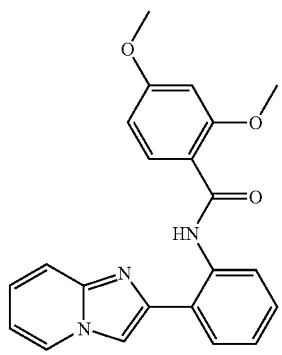 | A | B |
| 266 | 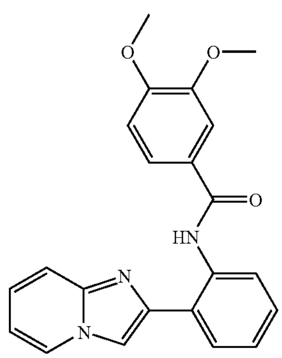 | A | A |
| 267 | 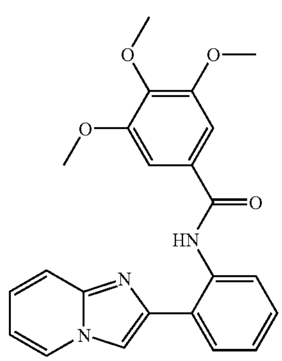 | A | B |

TABLE 5-continued
ED₅₀ and fold activation values for indicated compounds.
| COMPOUND NO | STRUCTURE | ED₅₀ MS ASSAY | FOLD ACTIVATION MS |
|---|---|---|---|
| 268 | 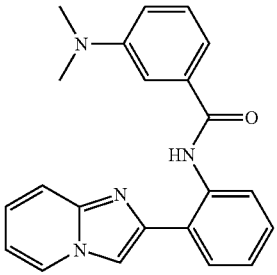 | A | B |
| 270 | 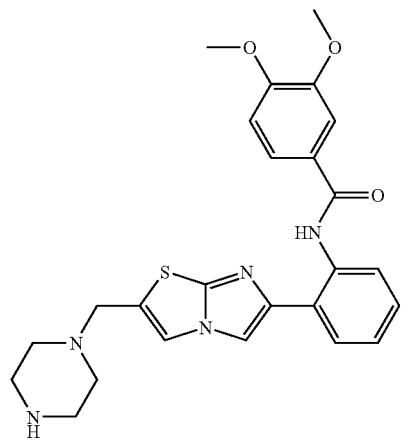 | A | A |
| 271 | 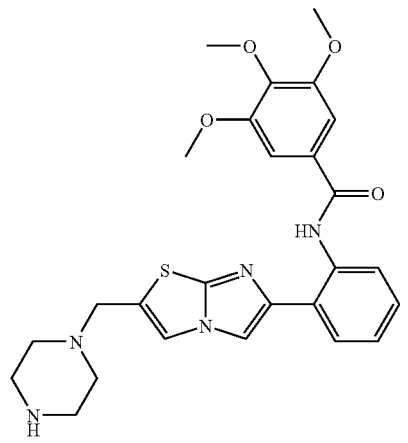 | A | A |
| 272 | 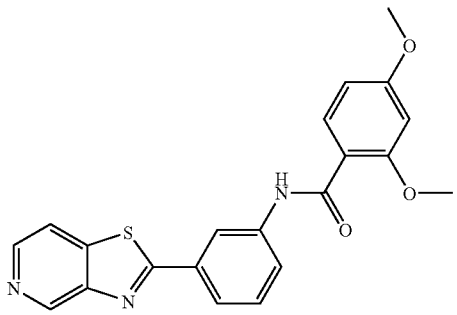 | A | B |

TABLE 5-continued

ED₅₀ and fold activation values for indicated compounds.

| COMPOUND NO | STRUCTURE | ED₅₀ MS ASSAY | FOLD ACTIVATION MS |
|---|---|---|---|
| 273 | 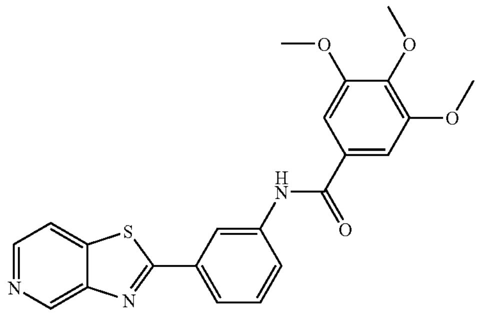 | A | A |
| 276 | 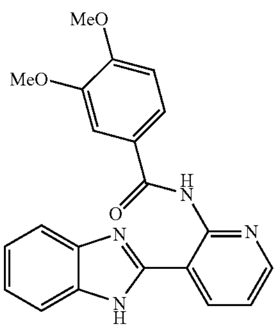 | A | B |
| 282 | 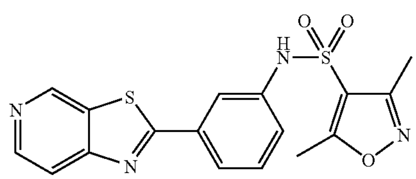 | NA | C |
| 283 | 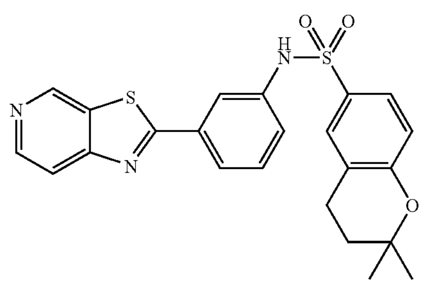 | NA | C |
| 284 | 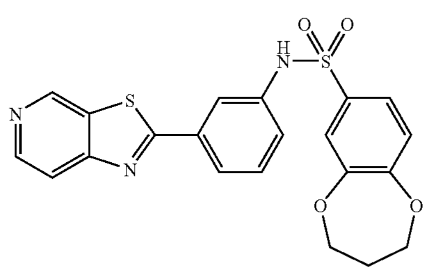 | NA | C |

TABLE 5-continued

ED$_{50}$ and fold activation values for indicated compounds.

| COMPOUND NO | STRUCTURE | ED$_{50}$ MS ASSAY | FOLD ACTIVATION MS |
|---|---|---|---|
| 285 | 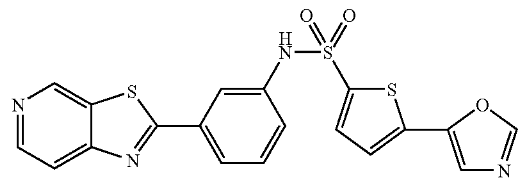 | NA | C |
| 286 | 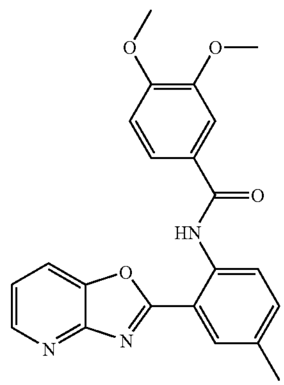 | NA | C |
| 288 | 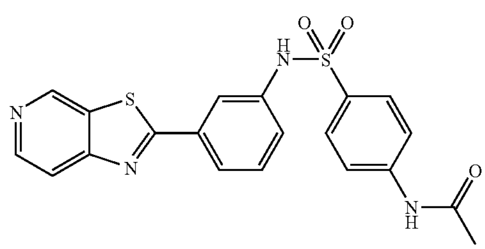 | A | B |
| 289 | 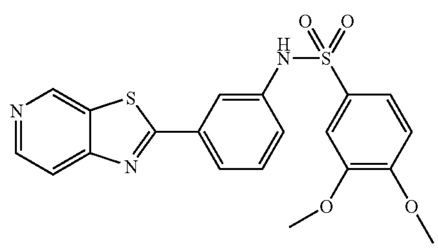 | A | B |
| 290 | 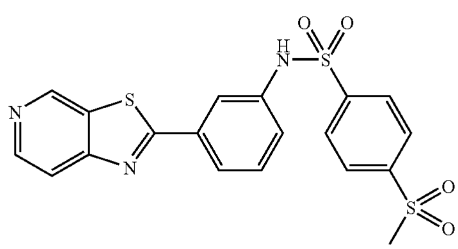 | NA | C |

Example 8

ATP Cell-Based Assay

This example describes the effect of the SIRT1 activator, resveratrol on cellular ATP levels in NCI-H358 cells. Cellular ATP levels are an indirect measurement of cellular metabolic rates and, by extension, mitochondrial function. As SIRT1 activation has been linked to increased mitochondrial biogenesis in vivo, this study is designed to determine if resveratrol increases mitochondrial function, using cellular ATP levels as the readout. The ATP assay is combined with a cellular viability assay so that cellular ATP levels can be normalized to viable cells. Cellular ATP levels were measured using the ATPLite 1Step Kit (PerkinElmer) and cellular viability was measured using the cell permeable dye, AlamarBlue™.

The Cellular ATP Assay is a multiplexed assay that measures both ATP levels and viability of a given cell sample. This assay is run in a 96-well Assay Plate and data are reported as the [ATP]/viability for each well in the Assay Plate.

The ATPLite 1Step™ Kit is a single-step luminescent cell-based assay for detection of ATP. The kit contains lyophilized substrate mixture, comprised of D-luciferin and the firefly (*Photinus pyralis*) enzyme luciferase. Additionally, the kit contains a detergent-based reconstitution buffer that induces the lysis of cellular membranes. The luciferase in the assay mixture catalyzes a reaction between the free cellular ATP and D-luciferin to produce bioluminescence according to the schematic reaction outlined below. The amount of light produced is proportional to the cellular ATP concentration.

The AlamarBlue™ Assay is a single-step assay that utilizes a soluble, non-toxic, cell permeable dye that is added to cell growth media. This dye undergoes electron reduction in viable cells but not dead cells. The reduced dye product gives a fluorescent signal which can be monitored with a fluorescence plate reader (excitation 545 nm and emission 575 nm). The amount of fluorescence generated in a given well is proportional to the number of viable cells. The viability signal generated by this assay is used to normalize the ATP signal from the ATPLite 1Step™ assay results.

Preparation of Test Substance for Cellular ATP Assay: resveratrol was weighed and placed in a brown vial. The material was dissolved in 100% vehicle (DMSO) to yield a final concentration of 10 mM (stock solution). The stock solution was serially diluted with 100% DMSO as described in SOP 7.10. The final concentrations of Resveratrol in the compound plate were 0.008, 0.023, 0.069, 0.206, 0.617, 1.852, 5.556, 16.667, 50 and 150 µM.

Figure 11:
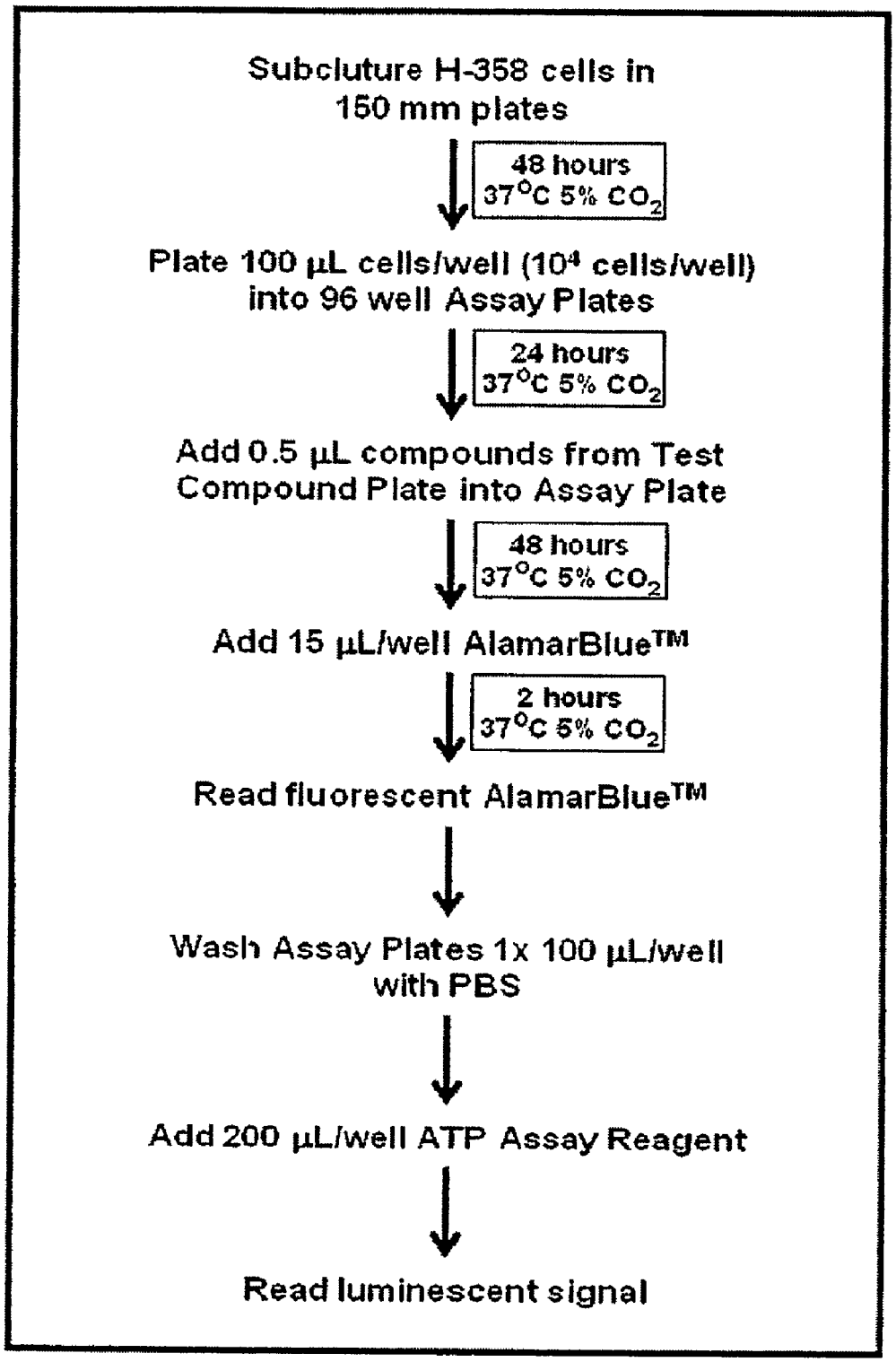
FIG. 11 shows a schematic of a cellular ATP assay.

The effect of resveratrol on cellular ATP levels in NCI-H358 cells (100 µL) was examined using the Cellular ATP Assay as described. The experimental design is summarized in FIG. 11. In this assay NCI-H358 cells (obtained from the American Tissue Culture Collection, ATCC) were seeded in 96 well microplates ($10^4$ cells/well). The NCI-H358 Growth Culture Media consists of RPMI 1640 Media supplemented with 10% FBS, 100 mg/mL streptomycin, and 100 units/mL penicillin. Three replicate cell microplates were treated with 15 µL of 10 concentrations of resveratrol (0.008, 0.023, 0.069, 0.206, 0.617, 1.852, 5.556, 16.667, 50 and 150 µM) or 15 µL vehicle (DMSO; final concentration of 0.5%; 12 replicates per plate). After 48 hours of compound treatment under cell growth conditions, plates were removed from the incubator, and 15 µl of AlamarBlue™ dye was added to each well. Cell microplates were incubated with dye for 2 hours under growth conditions, and fluorescence was subsequently measured using a plate reader. Media containing AlamarBlue™ was removed, and plates were washed in 100 µl of PBS per well. This wash was removed, and 200 µl of 1× ATPLite 1Step reagent was added to each well. Luminescence was then measured using a plate reader. The ATP signal for each well, measured by the luminescence scan, was normalized to its corresponding cell viability value, measured by the fluorescence scan, to generate the average ATP level per viable cell unit (ATP/vCell). The ATP/vCell for each treatment was then normalized to the average vehicle ATP/vCell for its respective cell microplate, yielding the normalized ATP/vCell (norm. ATP/vCell). Finally, the norm. ATP/vCell for each unique treatment was averaged across plate replicates, generating the average norm. ATP/vCell. Doses of resveratrol that increase cellular ATP levels have normalized ATP/vCell values greater than 1.0. The concentration of resveratrol which gives the 50% of the maximum increase in normalized ATP/vCell ($EC_{50}$ ATP) was determined by a best-fit curve analysis using a sigmoidal dose-response curve model.

The ATP levels of cells treated with 10 concentrations of resveratrol or vehicle alone were measured. Each of these ATP levels was normalized to the cell viability in the corresponding treatment well, generating the ATP/vCell value. Each ATP/vCell value was subsequently normalized to its average Vehicle ATP/vCell values for its respective cell microplate.

Figure 12:
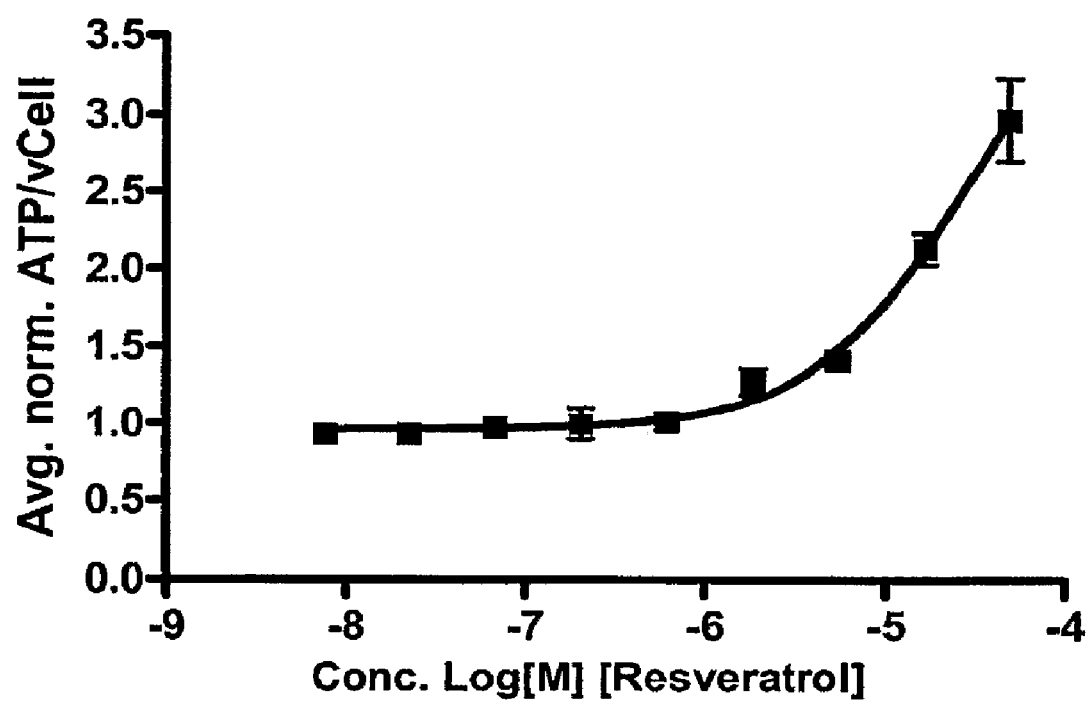
FIG. 12 shows a dose-response curve for resveratrol treatment.

Data are represented as the normalized ATP/vCell (arbitrary units) FIG. 12 shows the best-fit, sigmoidal dose-response curve for the 10 concentrations of resveratrol plotted against their corresponding normalized ATP/vCell values. These values represent an average of three plate replicates. resveratrol increases cellular ATP levels in NCI-H358 cells in a dose-dependent manner. The maximum increase in cellular ATP levels was 3.0 fold and occurred with treatment of 50 µM resveratrol. The $EC_{50}$ ATP for resveratrol was determined to be 29 µM.

Example 9

Screening of Test Compounds in ATP Cell-Based Assay

A number of compounds were screened for their affect on ATP levels in the assay as described in Example 8. Results are shown in Table 6. The $ED_{50}$ values for compounds that raised intracellular ATP levels are represented by A ($ED_{50}$=<50 µM), B ($ED_{50}$=51-100 µM), C ($ED_{50}$=101-150 µM), and D ($ED_{50}$=>150 µM). NA means that the compound was not tested using the indicated assay. Similarly, the $IC_{50}$ values for the compounds that lowered intracellular ATP levels are represented by A ($IC_{50}$=<50 µM), B ($IC_{50}$=51-100 µM), C ($IC_{50}$=101-150 µM), and D ($IC_{50}$=>150 µM).

TABLE 6

ED$_{50}$ values for IC$_{50}$ values for sirtuin activating and inhibiting compounds, respectively.

| COMPOUND No | STRUCTURE | ED$_{50}$ ATP ASSAY | IC$_{50}$ ATP ASSAY |
|---|---|---|---|
| 11 | 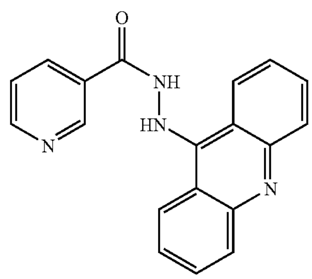 | A | |
| 52 | 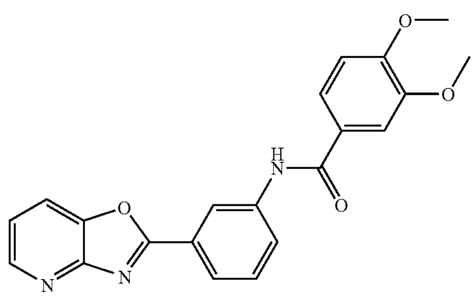 | A | |
| 118 | 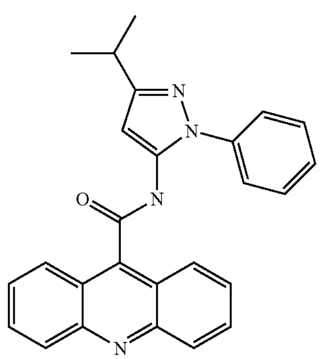 | | D |
| 120 | 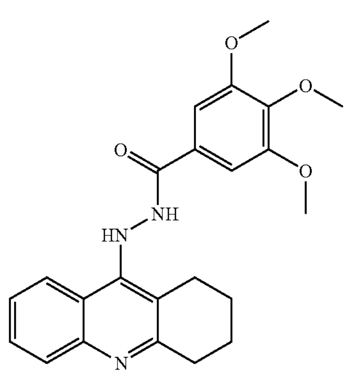 | A | |

TABLE 6-continued

ED$_{50}$ values for IC$_{50}$ values for sirtuin activating and inhibiting compounds, respectively.

| COMPOUND No | STRUCTURE | ED$_{50}$ ATP ASSAY | IC$_{50}$ ATP ASSAY |
|---|---|---|---|
| 42 | 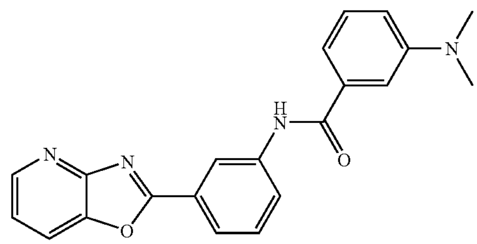 | A | |
| 49 | 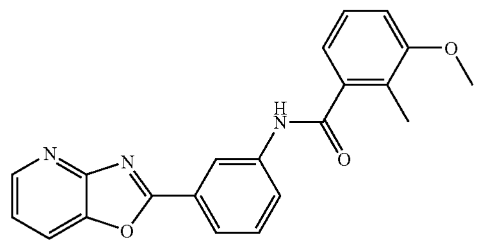 | A | |
| 115 | 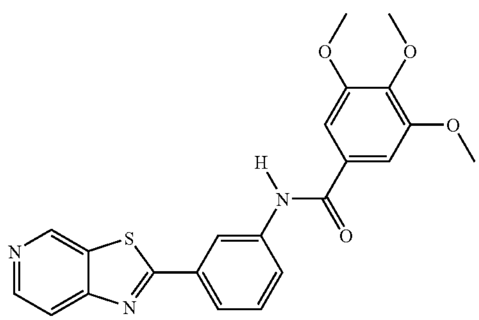 | D | |
| 79 | 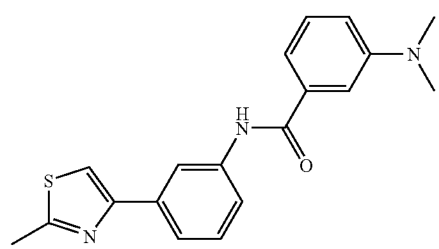 | A | |
| 117 | 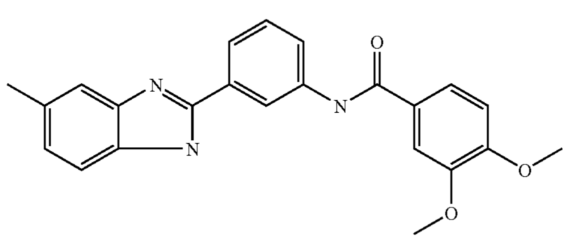 | | B |
| 120 | 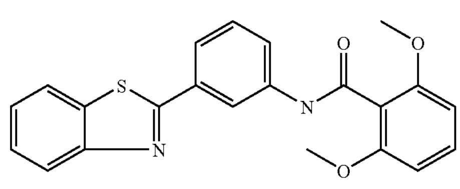 | A | |

TABLE 6-continued
ED$_{50}$ values for IC$_{50}$ values for sirtuin activating and inhibiting compounds, respectively.
| COMPOUND No | STRUCTURE | ED$_{50}$ ATP ASSAY | IC$_{50}$ ATP ASSAY |
|---|---|---|---|
| 121 | 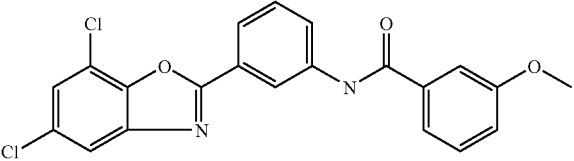 | NA | |
| 123 | 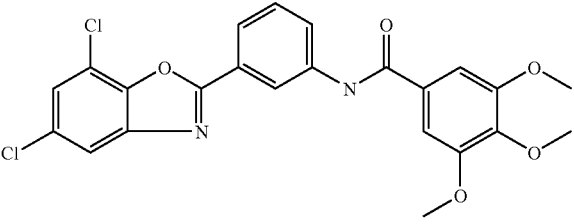 | D | |
| 85 | 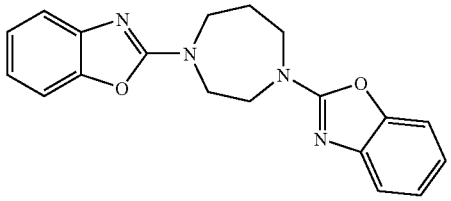 | NA | |
| 86 | 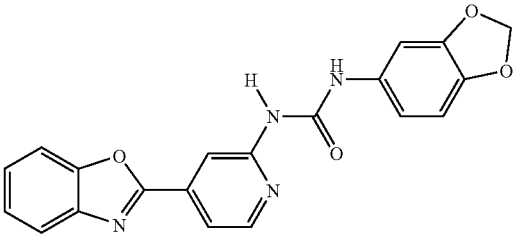 | A | |
| 87 | 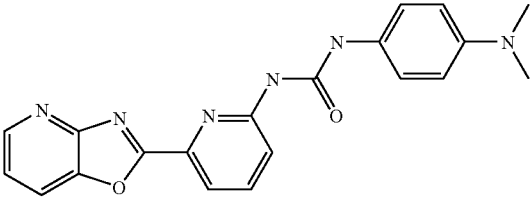 | NA | |
| 88 | 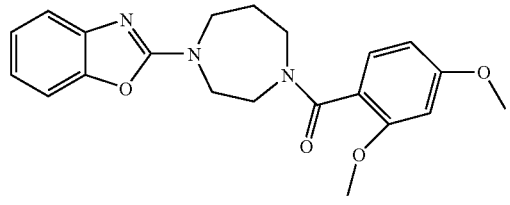 | NA | |
| 89 | 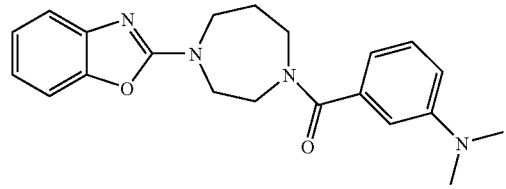 | | A |

TABLE 6-continued

ED$_{50}$ values for IC$_{50}$ values for sirtuin activating and inhibiting compounds, respectively.

| COMPOUND No | STRUCTURE | ED$_{50}$ ATP ASSAY | IC$_{50}$ ATP ASSAY |
|---|---|---|---|
| 90 | 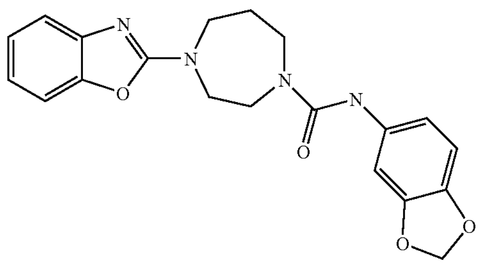 | D | |
| 91 | 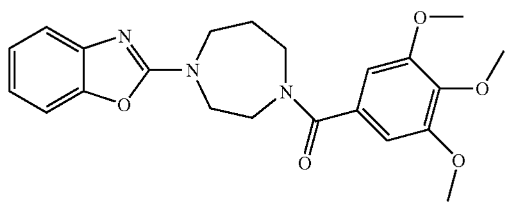 | | A |
| 92 | 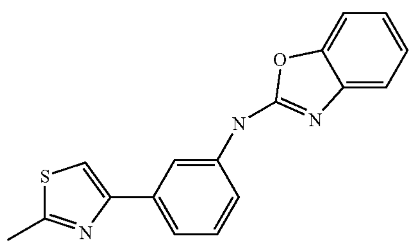 | | B |
| 93 | 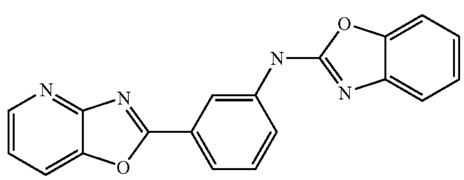 | D | |
| 94 | 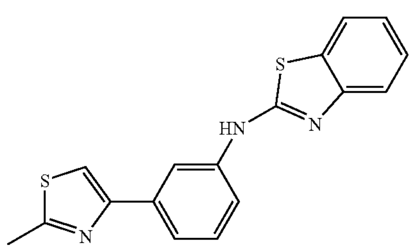 | D | |
| 95 | 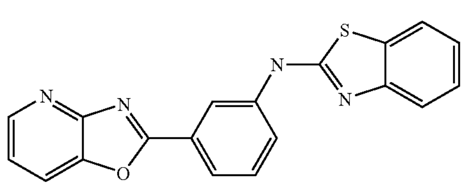 | NA | |

TABLE 6-continued

ED$_{50}$ values for IC$_{50}$ values for sirtuin activating and inhibiting compounds, respectively.

| COMPOUND No | STRUCTURE | ED$_{50}$ ATP ASSAY | IC$_{50}$ ATP ASSAY |
|---|---|---|---|
| 97 | 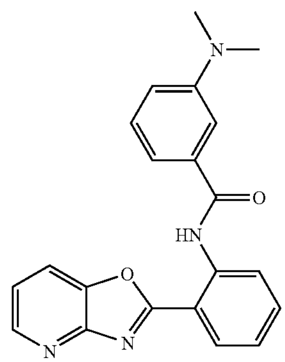 | A | |
| 98 | 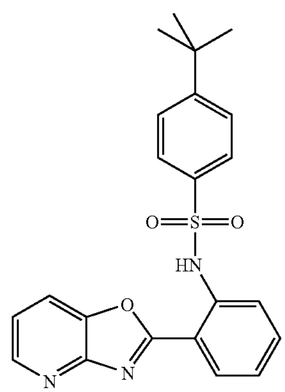 | NA | |
| 99 | 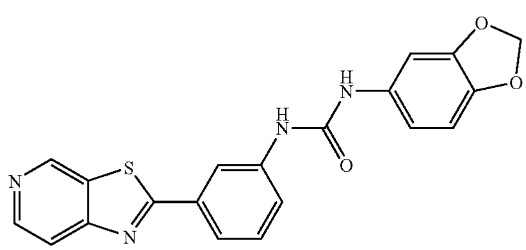 | A | |
| 100 | 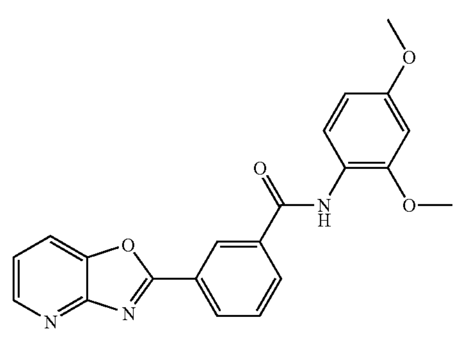 | A | |

TABLE 6-continued

ED$_{50}$ values for IC$_{50}$ values for sirtuin activating and inhibiting compounds, respectively.

| COMPOUND No | STRUCTURE | ED$_{50}$ ATP ASSAY | IC$_{50}$ ATP ASSAY |
|---|---|---|---|
| 101 | 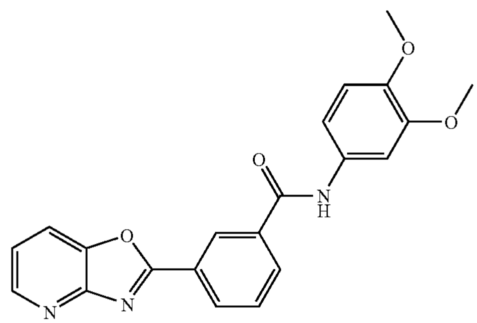 | | C |
| 102 | 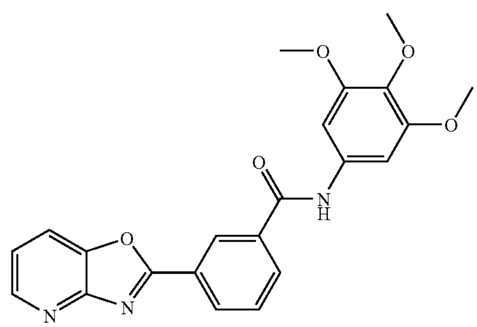 | | A |
| 103 | 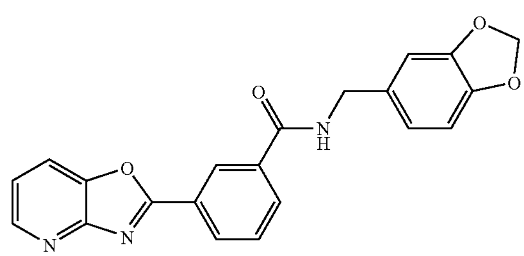 | | NA |
| 104 | 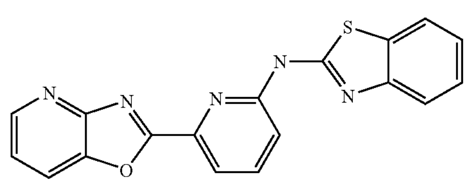 | | A |
| 105 | 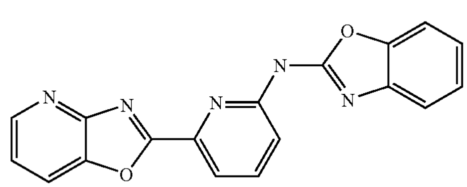 | | A |

TABLE 6-continued

ED$_{50}$ values for IC$_{50}$ values for sirtuin activating and inhibiting compounds, respectively.

| COMPOUND No | STRUCTURE | ED$_{50}$ ATP ASSAY | IC$_{50}$ ATP ASSAY |
|---|---|---|---|
| 133 | 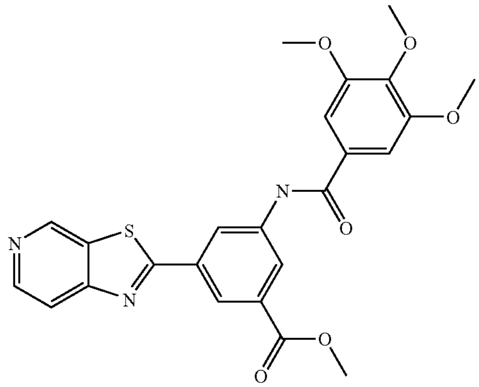 | | NA |
| 134 | 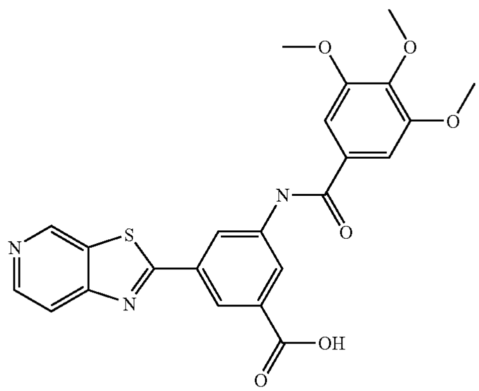 | | NA |
| 135 | 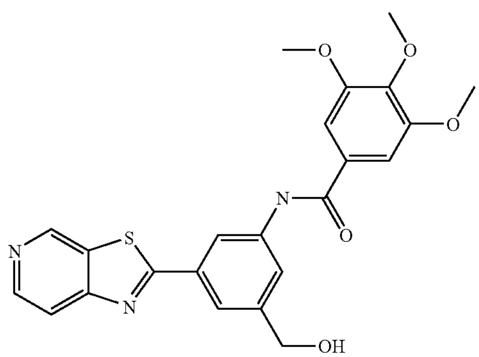 | | A |
| 106 | 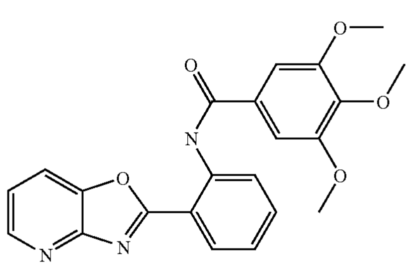 | | A |

Example 10

Identification of Sirtuin Activatable Cell Lines

Western blot experiments were conducted to identify cell lines that had relatively low endogenous SIRT1 expression levels. The goal was to identify cell lines in which SIRT1 activity was not saturating so that an increase in SIRT1 activity upon exposure of the cell to a sirtuin activating compound would be observable in the cellular ATP assay described above. The opposite approach would be taken to identify sirtuin inhibiting compounds, i.e. cells with high endogenous SIRT1 expression levels would be preferred.

Figure 13:
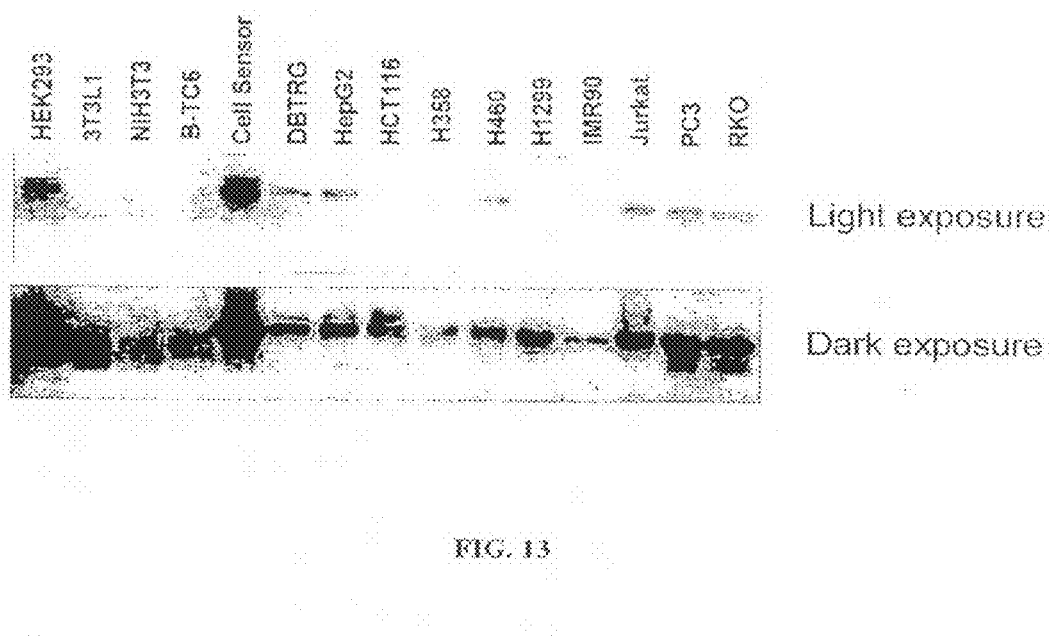
FIG. 13 shows a western blot to identify cell lines having a relatively low endogenous level of SIRT1 expression.

FIG. 13 shows the results of a western blot experiment to determine the levels of SIRT1 expression levels in a variety of cell lines. Equal amounts of cell lysates were analyzed by western analysis for expression of endogenous SIRT1. Blots were probed with a primary rabbit polyclonal antibody to SIRT1 (Abcam, Cat. # AB13749) and a secondary goat anti-rabbit IgG conjugated to HRP (Santa Cruz, Cat.# SC-2054). As can be seen, SIRT1 expression varies widely across different cell lines with maximum expression observed in HEK293 and minimal expression observed in IMR90 and H358 cells.

Figure 14:
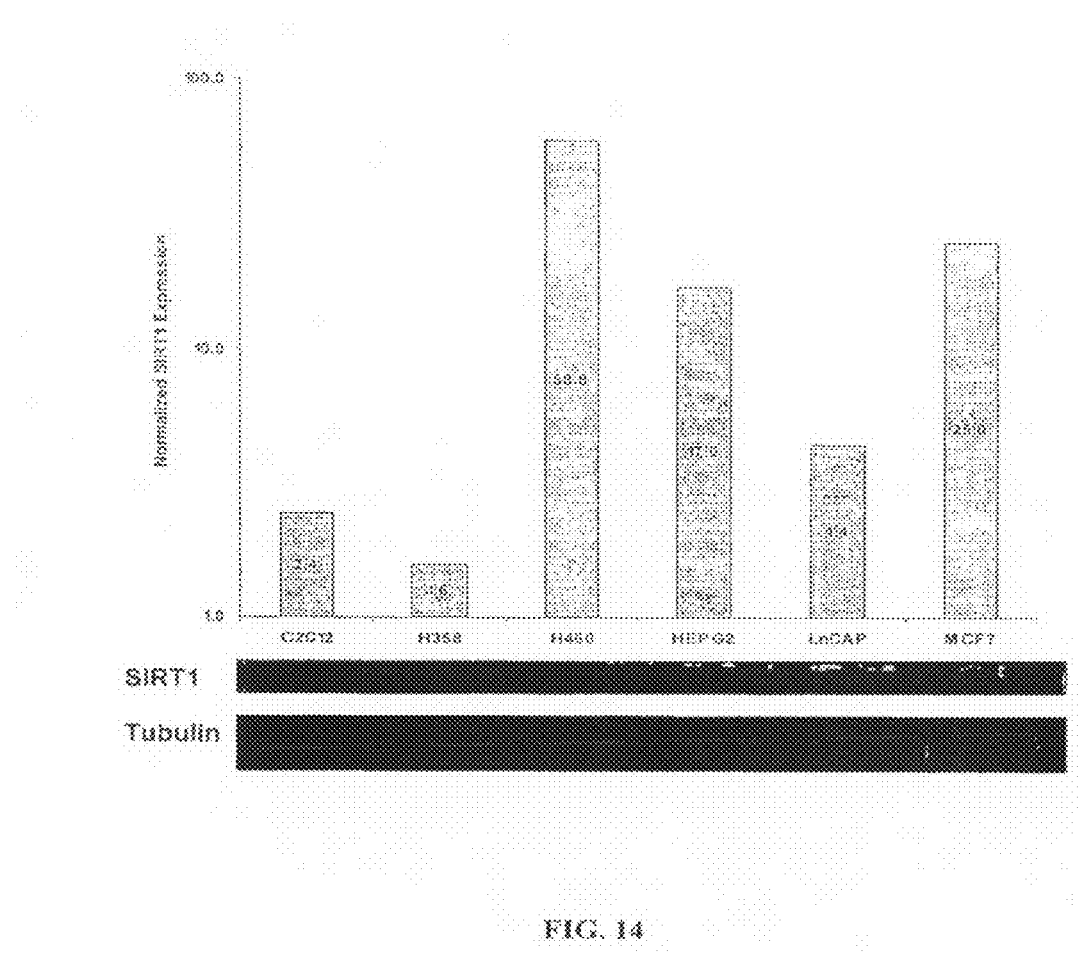
FIG. 14 shows a western blot of SIRT1 versus Tubulin levels in a variety of cell types and a corresponding bar plot showing normalized SIRT1 expression for a variety of cell types.

FIG. 14 shows the results of a western blot experiment to determine expression levels of SIRT1 protein normalized to the expression level of tubulin in a variety of cell lines. Western analysis of a panel of human cell lines looking at expression levels of SIRT1 protein. SIRT1 expression was normalized to alpha tubulin expression. All samples were assayed in duplicate. Protein quantification was preformed using infrared dye labeled secondary antibodies followed by blot scan using the Licor® Odyssey® scanner. The primary antibodies used are mouse monoclonal to alpha tubulin, (Santa Cruz Biotech, Cat # SC-8035) and rabbit polyclonal to SIRT1 (Abcam, Cat. # AB13749). Secondary antibody used for SIRT1 detection was IRDye 800 conjugated Anti-Rabbit IgG (Goat) (Rockland Immunochemicals, Cat.#611-132-122) and for tubulin expression was AlexaFluor 680 goat anti-mouse IgG (InVitrogen Cat. # A21057).

The cell lines were also tested in the cellular ATP assays described above to identify cell lines that had relatively lower levels of mitochondria and/or oxidative phosphorylation such that an increase in ATP levels upon exposure to a sirtuin activating compound would be observable. Cell lines NCI-H358 and MCF7 were identified as suitable cell lines for conducting the cellular ATP assays described above. Both cell lines had relatively low endogenous levels of SIRT1 expression and permitted observation of an increase in ATP levels upon exposure to a sirtuin activating compound.

Example 11

Correlation of Increased ATP Levels with Increased Mitochondrial Mass

Western blots were conducted to correlate an observed increase in cellular ATP levels upon exposure of cells to a sirtuin activating compound to an increase in mitochondrial mass. Levels of three different independent markers of mitochondrial mass were determined by western blot analysis following exposure of cells to the sirtuin activator resveratrol. Observed increases in cellular ATP levels upon treatment with resveratrol correlated with increases in the levels of mitochondrial mass biomarkers.

Figure 15:
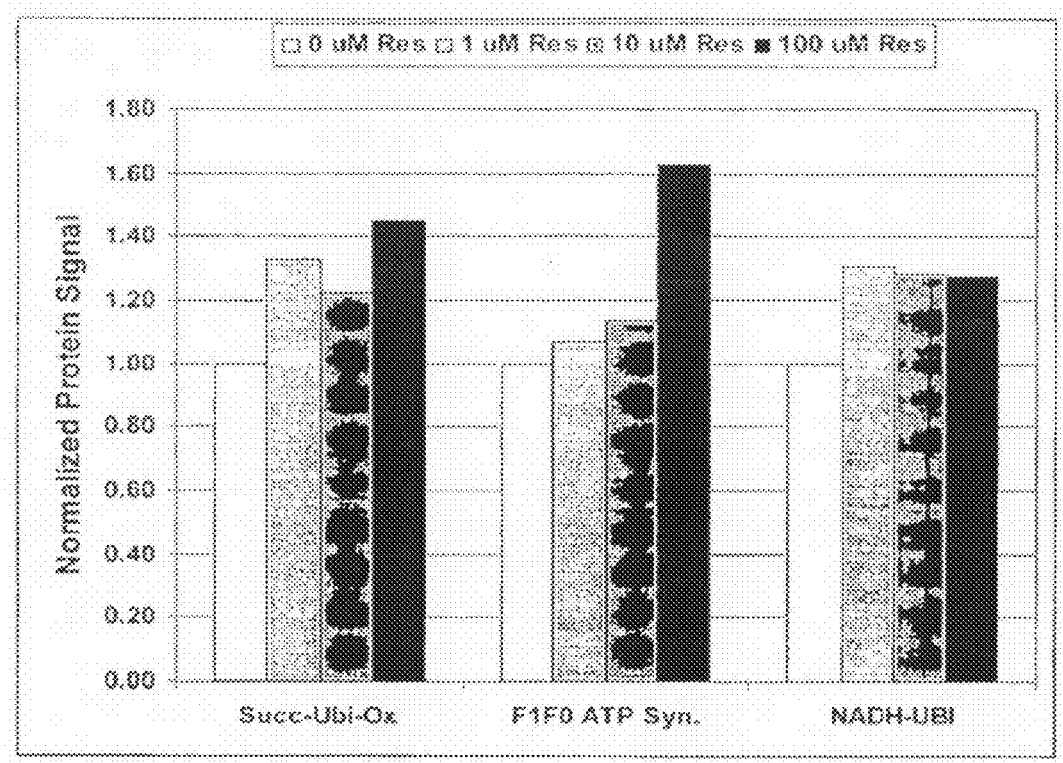
FIG. 15 shows a bar plot of normalized protein signal for three mitochondrial markers after a 48 hour exposure of NCI-H358 cells to several concentrations of resveratrol. Succ-Ubi-Ox is Succinate-Ubiquinol Oxidoreductase; F1F0 ATP Syn. is ATP synthase F1F0; and NADH-UBI is NADH-Ubiquinol Oxidoreductase.

FIG. 15 shows the results of a western blot experiment to determine the levels of several mitochondrial mass biomarkers after exposure of cells to various concentrations of resveratrol. NCI-H538 cells were treated for 48 hours with either 0, 1, 10 or 100 uM resveratrol. Cell lysates were then prepared and specific mitochondrial proteins were quantitated by western analysis using antibodies specific to the following proteins: Succinate-Ubiquinol Oxidoreductase (Mitochondrial Complex II Protein, mouse monoclonal, InVitrogen, Cat. #A11142); ATP synthase F1F0 (Mitochondrial Complex V Protein, mouse monoclonal, InVitrogen, Cat.# A21350); NADH-Ubiquinol Oxidoreductase (Mitochondrial Complex I Protein, mouse monoclonal, InVitrogen, Cat. #A21344). Normalization was to alpha tubulin using a rabbit polyclonal (Santa Cruz Biotech, Cat # SC-9104). Secondary antibody used for specific protein detection was AlexaFluor 680 conjugated Anti-Rabbit IgG (Goat) (Rockland Immunochemicals, Cat.#610-132-121) and for tubulin expression was IRDye 800 goat anti-mouse IgG (InVitrogen Cat. # A21076). Protein quantification was preformed using infrared dye labeled secondary antibodies followed by blot scan using the Licor® Odyssey® scanner.

Example 12

Alternative Mass Spectrometry Assay of Sirtuin Activity

The following example describes an alternative mass spec based assay for determination of Sirt1 deacetylase activity. Instead of relying on purified or recombinant enzyme, the reaction utilizes endogenous Sirt1 enzyme from cell or tissue extracts. This allows for the determination of endogenous sirtuin activity. The cells or tissues can be pretreated with Sirt1 modulators or other control compounds either following isolation or following pharmacological intervention in vivo. Alternatively, this measurement of endogenous sirtuin activity can be measured in various clinical samples following physiological manipulation (diet, exercise, age, disease progression, etc.) or following pharmacological intervention including studies designed to study dose responsiveness and escalation, vehicle or placebo control, dosing regimen, drug combination and synergy, etc.

A procedure for isolating viable (living) white blood cells (WBC) (also called "Peripheral Blood Mononuclear Cells") from whole blood is provided. This procedure is based on approximately 6 ml of whole blood (Vacutainer format). This is the content of a standard tube (Becton Dickinson Vacutainer™ CPT™ Cell Preparation Tubes with Sodium Heparin, cat.#362753). Mix the blood before centrifugation by 10 times gently inverting the tube up and down. Centrifuge the CPT-tubes 20 minutes at 1700 RCF (3100 RPM) at room temperature (18-25° C.) with the brake off. Open the CPT tube and remove the plasma (4 ml) without disturbing the cell phase. Store the plasma if necessary. Remove the cell phase (ca. 2 ml, containing WBC, platelets and some plasma) with a plastic Pasteur (transfer) pipette and transfer this phase to a 15 ml conical Falcon-tube. Add phosphate buffered saline (PBS) to the cells to bring the volume up to 13 ml. Mix carefully by inverting the tube. Centrifuge the 15 ml conical tube at 300 RCF (1200 RPM) for 15 minutes at room temperature (18-25° C., no brake). Aspirate the supernatant (PBS, platelets and some plasma) without disturbing the cell pellet, and resuspend the cell pellet (WBC) in the remaining PBS (approximately 200 μl). Add PBS to the remaining cell suspension to bring the volume up to 13 ml, mix carefully by inverting the tube. Centrifuge at room temperature at 300 RCF (1200 RPM) for 15 minutes at room temperature (18-25° C., no brake). Aspirate the supernatant without disturbing the cell pellet, and resuspend the cell pellet in the remaining PBS (approximately 200 μl). Add PBS to the remaining cell suspension to bring the volume up to 10 ml, mix carefully by inverting the tube. Centrifuge at room temperature at 300 RCF (1200 RPM) for 15 minutes at room temperature (18-25° C., no brake). Aspirate the supernatant without disturbing the cell pellet. From this point keep the cells on ice.

Add 1 ml Freeze Medium without FBS (RPMI Medium 1640 with L-Glutamine; DMSO (dimethyl sulfoxide), 10% (vol:vol) final) to the remaining cell pellet and resuspend the cells gently. For some uses where plasma proteins do not interfere with the assay, e.g. for mtDNA quantification (but NOT for CS activity measurement), the WBC pellet can be resuspended and frozen in Freeze Medium with FBS (RPMI Medium 1640 with L-Glutamine; DMSO (dimethyl sulfoxide), 10% (vol:vol) final; FBS (Fetal Bovine Serum), heat inactivated 30 minutes at 56° C., 20% (vol:vol) final. Plasma proteins help maintain cell integrity when frozen. Once the Freeze Medium is added the cells must remain on wet ice for the remainder of the process and should be frozen as soon as possible. Transfer the cell suspension into cryovials (2 aliquots of 0.5 ml per sample). Freeze the cryovials by placing them into a −80° C. freezer. Keep the WBC samples at −80° C. until use. Six milliliters of blood gives around 10 million WBC, containing around 4 μg total RNA, 40 μg total cell proteins and 0.15 ng SIRT1 protein.

600-800 million WBC corresponding to ~0.26 nM of SIRT1 in 20 μL of final lysate are used for a standard experiment to measure the activity of SIRT1 with five time points in triplicate for two given sets of experiments. The amount of SIRT1 in each preparation is determined initially by Western-Blot analysis using different amounts of WBC with a given SIRT1 standard (purified SIRT1, bacterially expressed).

The WBC are thawed and collected in a single 15 mL falcon tube at 4 degrees Celsius. The assay buffer consists of 10× reaction buffer, 5 mM DTT and 0.05% BSA. The reaction buffer is prepared as a 10× stock and consists of 500 mM Tris HCl pH 8.0, 1370 mM NaCl, 27 mM KCl, and 10 mM $MgCl_2$. The buffer is stored at room temperature. Prior to use the final assay buffer is chilled at 4 degrees Celsius. 700 μL of assay buffer is added to the collected WBC and gently mixed. Cells are sonicated on ice for 2 minutes with intervals (15 seconds sonication, 30 seconds pause) at a power output level of 1.5 with a small sonicator probe (Virsonic sonicator). The sonicated cells are centrifuged for 5 minutes at 3000 rpm and the supernatant (referred to as "lysate") is removed for further use in the activity assay.

Alternatively, lysates can be prepared from tissue, such as liver, fat or muscle. Typically, two to six pieces of one liver (approx, 500 mg) or two pieces of muscle (approx, 180 mg) corresponding to ~0.26 nM of SIRT1 in 20 μL of final lysate are used for a standard experiment to measure the activity of SIRT1 with five time points in triplicate for two given sets of experiment. The amount of SIRT1 in each preparation is again determined initially by Western-Blot analysis using different amounts of mouse liver lysates or muscle lysates with a given SIRT1 standard (purified SIRT1, bacterially expressed). 700 μL of assay buffer are added to the collected tissues and gently mixed. Then these tissues are homogenized on ice using a Polytron for 20 seconds at maximum speed. (Omni International GLH). The homogenized tissues are centrifuged for 5 minutes at 13,000 rpm and the supernatant (referred to as "lysate") is removed for further use in the activity assay.

Finally, lysates can also be prepared from cell lines, such as those derived from liver, muscle, fat etc. The following describes preparation of lysates from myoblast C2C12 cell line. Myoblast cells are grown to 80% confluence and harvested with TrypLE (Invitrogen), then washed twice with PBS buffer (Invitrogen) and stored at −80 degree Celsius prior to use. A C2C12 myoblast cell pellet ~100 to 200 mg corresponding to ~0.26 nM of SIRT1 in 20 μL of final lysate is used for a standard experiment to measure the activity of SIRT1 with five time points in triplicate for two given sets of experiment. The amount of SIRT1 in each preparation is determined initially by Western-Blot analysis using different amounts of cells with a given SIRT1 standard (purified SIRT1, bacterially expressed). 700 μL of assay buffer are added to the collected myoblast cells and gently mixed. Then these cells are sonicated on ice for 2 minutes with intervals (15 seconds sonication, 30 seconds pause) at a power output level of 1.5 with a small sonicator probe (Virsonic sonicator). The sonicated cells are centrifuged for 5 minutes at 3000 rpm and the supernatant (referred as "lysate") is removed for further use in the activity assay. 20 uL of lysate are taken typically for one well of a 96 well plate with a final total reaction volume of 100 uL.

20 uL of lysate are taken typically for one well of a 96 well plate with a final total reaction volume of 100 uL. 1 μL of DMSO is added to each of the wells to give a final concentration of 1%. 29 uL of assay buffer are added to an initial volume of 50 uL. Stop buffer (10% trichloroacetic acid and 500 mM Nicotinamide) is added to the wells designated to zero time points. The activity assay is started by adding 50 uL of substrate buffer to each well. The substrate buffer consists of 20 μM Tamra peptide Ac-Glu-Glu-Lys(Biotin)-Gly-Gln-Ser-Thr-Ser-Ser-His-Ser-Lys(Ac)-Nle-Ser-Thr-Glu-Gly-Lys (5TMR)-Glu-Glu-NH2 (SEQ ID NO: 34) wherein K(Ac) is an acetylated lysine residue and Nle is a norleucine. The peptide is labeled with the fluorophore 5TMR (excitation 540 nm/emission 580 nm) at the C-terminus for use in the FP assay described above. The peptide substrate is prepared as a 1 mM stock in distilled water and stored in aliquots at −20° C.), 5 mM DTT, 0.05% BSA, 4 mM $NAD^+$ and 10× reaction buffer. The reaction is performed at room temperature. For each time point the reaction will be stopped with stop buffer. After the final time point is collected the plates are sealed and analyzed by mass spectrometry.

As controls, specific SIRT1 and HDAC inhibitors are also included in the assay. Lysate volumes are adjusted accordingly to the amount needed for this inhibition assay. The following inhibitors are used with their respective final concentrations: 6-chloro-2,3,4,9-tetrahydro-1-H-carbazole-1-carboxamide (5 μM), TSA (1 μM) and nicotinamide (5 mM). 6-chloro-2,3,4,9-tetrahydro-1-H-carbazole-1-carboxamide and TSA are prepared in DMSO. Nicotinamide preparations are made in water. The final concentration of DMSO in each well is 1%. 1 μL of DMSO is added to wells containing Nicotinamide as inhibitor. The reactions are run in duplicate over a time period of 90 to 120 minutes with at least 5 time points taken.

Assay plates are transferred to BioTrove, Inc. (Woburn, Mass.) on dry ice for mass spectrometry analysis. Thawed reactions are analyzed using an Agilent 1100 HPLC with a microplate autosampler linked in series with a Sciex API-4000 mass spectrometer. Proprietary equipment (developed by BioTrove, Inc.) has been incorporated into this LC-MS system to allow for rapid sampling and rapid sample clean-up (4-5 sec per well). Both substrate and product are tracked in the MS and the area of the MS curve for both product and substrate are reported back in arbitrary units.

Using Microsoft Excel, plot product on the x axis and reaction time on the y axis of a xy scatter plot. The reaction is run at saturating substrate conditions with deliver a maximal turnover of substrate to product over a fixed time period, necessary for the detection of the activity of SIRT1. The final readout will be a number/slope describing product accumulation/time/ng of enzyme. Inhibition of the enzymatic activity of SIRT1 results in low product yields that enable the differentiation between HDAC's and SIRT1.

Figure 16A:
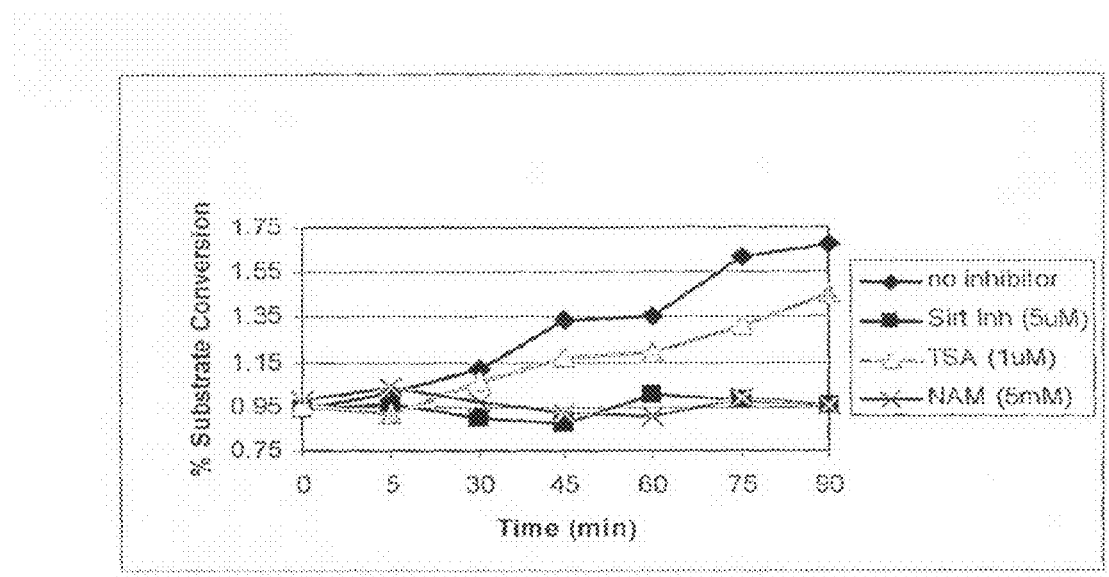
FIGS. 16A and 16B shows the effect of pretreatment of lysates prepared from C2C12 cells (FIG. 16A) or human peripheral white blood cells (FIG. 16B) with 6-chloro-2,3,4, 9-tetrahydro-1-H-carbazole-1-carboxamide (Sirt Inh, 5 µM), TSA (1 µM) and nicotinamide (NAM, 5 mM) on deacetylase activity as described in Example 12.
Figure 16B:
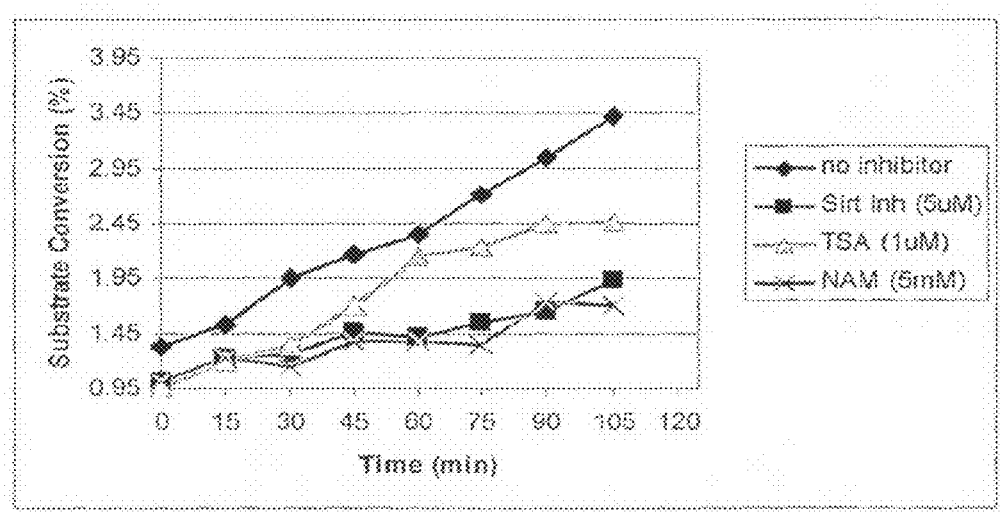

FIGS. 16A and 16B show the results of sirtuin activity in cell lysates as determined using mass spectrometry. FIG. 16A shows sirtuin activity in lysates of C2C12 cells that were pretreated as indicated and FIG. 16B shows sirtuin activity in lysates of human peripheral white blood cells that were pretreated as indicated.

EQUIVALENTS

The present invention provides among other things assays for determining acetylase and/or deacetylase activity and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih-.gov).

The ASCII text file SIRT023_US_Sequence listing.txt, created Sep. 25, 2012 and 16 kilobytes in size, is hereby incorporated-by-reference in its entirety.

The invention claimed is:

1. A method for identifying a compound that activates a deacetylase, comprising:
   contacting a peptide substrate pool with a deacetylase in the presence of a test compound in vitro, wherein the concentration of peptide substrate in the peptide substrate pool is below the $K_m$ of the deacetylase for the peptide substrate, and wherein members of said peptide substrate pool comprise at least one acetylated lysine residue, and
   determining the level of acetylation of the peptide substrate pool using mass spectrometry, wherein a decrease in the level of acetylation of the peptide substrate pool in the presence of the test compound as compared to a control reaction in which the test compound is not included indicates that the test compound activates the deacetylase.

2. The method of claim 1, wherein the concentration of peptide substrate in the peptide substrate pool is at least two fold below the $K_m$ of the deacetylase for the peptide substrate.

3. The method of claim 2, wherein the concentration of peptide substrate in the peptide substrate pool is at least 10 fold below the $K_m$ of the deacetylase for the peptide substrate.

4. The method of claim 1, wherein the sequence of the peptide substrate is derived from a histone, an HMG protein, p53, c-Myb, GATA-1, EKLF, MyoD, E2F, dTCF, or HIV Tat, or a fragment thereof.

5. The method of claim 1, wherein the substrate peptide pool comprises a single peptide species.

6. The method of claim 1, wherein the substrate peptide pool comprises a mixture of two or more peptides.

7. The method of claim 1, wherein the deacetylase is a histone deacetylase (HDAC) or a sirtuin.

8. The method of claim 7, wherein the sirtuin is a SIRT1 protein.

9. The method of claim 1, wherein a compound that activates a sirtuin to a greater extent than resveratrol is identified.

10. The method of claim 9, wherein a compound that has sirtuin activating activity at least 5-fold greater than the sirtuin activating activity of resveratrol is identified.

11. The method of claim 1, wherein the mass spectrometry is electrospray ionization (ESI) mass spectrometry or matrix-assisted laser desorption/ionization (MALDI) mass spectrometry.

12. The method of claim 1, wherein the compound is a small molecule.

13. The method of claim 1, which is performed in high-throughput format.

14. The method of claim 1, wherein the concentration of peptide substrate in the peptide substrate pool is at least 5 fold below the Km of the deacetylase for the peptide substrate.

15. The method of claim 1, wherein the concentration of peptide substrate in the peptide substrate pool is at least 20 fold below the Km of the deacetylase for the peptide substrate.

* * * * *

SEQUENCE LISTING

```
<160> NUMBER OF SEQ ID NOS: 35

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Lys(Ac)
<220> FEATURE:
<221> NAME/KEY: MOD_RES
<222> LOCATION: (13)
<223> OTHER INFORMATION: Nle
<220> FEATURE:
<221> NAME/KEY: MOD_RES
<222> LOCATION: (18)
<223> OTHER INFORMATION: Lys(MR121)

<400> SEQUENCE: 1

Glu Glu Lys Gly Gln Ser Thr Ser Ser His Ser Lys Xaa Ser Thr Glu
 1               5                  10                  15

Gly Lys Glu Glu
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Lys(Ac)
<220> FEATURE:
<221> NAME/KEY: MOD_RES
<222> LOCATION: (13)
<223> OTHER INFORMATION: Nle
<220> FEATURE:
<221> NAME/KEY: MOD_RES
<222> LOCATION: (18)
```

-continued

```
<223> OTHER INFORMATION: Lys(5-TMR)

<400> SEQUENCE: 2

Glu Glu Lys Gly Gln Ser Thr Ser Ser His Ser Lys Xaa Ser Thr Glu
  1               5                  10                  15

Gly Lys Glu Glu
            20

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Lys(Ac)
<220> FEATURE:
<221> NAME/KEY: MOD_RES
<222> LOCATION: (12)
<223> OTHER INFORMATION: Lys(MR121)

<400> SEQUENCE: 3

Thr Asn Pro Ala Ile Val Lys Thr Glu Asn Ser Lys
  1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Lys(Ac)
<220> FEATURE:
<221> NAME/KEY: MOD_RES
<222> LOCATION: (12)
<223> OTHER INFORMATION: Lys(5-TMR)

<400> SEQUENCE: 4

Thr Asn Pro Ala Ile Val Lys Thr Glu Asn Ser Lys
  1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Lys(Ac)
<220> FEATURE:
<221> NAME/KEY: MOD_RES
<222> LOCATION: (12)
<223> OTHER INFORMATION: Lys(MR121)

<400> SEQUENCE: 5

Gln His Leu Gln Ala Lys Pro Thr Thr Leu Ser Lys
  1               5                  10

<210> SEQ ID NO 6
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Lys(Ac)
<220> FEATURE:
<221> NAME/KEY: MOD_RES
<222> LOCATION: (12)
<223> OTHER INFORMATION: Lys(5-TMR)

<400> SEQUENCE: 6

Gln His Leu Gln Ala Lys Pro Thr Thr Leu Ser Lys
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Lys(Ac)
<220> FEATURE:
<221> NAME/KEY: MOD_RES
<222> LOCATION: (10)
<223> OTHER INFORMATION: Lys(MR121)

<400> SEQUENCE: 7

Met Pro Ser Asp Lys Thr Ile Gly Gly Lys
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Lys(Ac)
<220> FEATURE:
<221> NAME/KEY: MOD_RES
<222> LOCATION: (10)
<223> OTHER INFORMATION: Lys(5-TMR)

<400> SEQUENCE: 8

Met Pro Ser Asp Lys Thr Ile Gly Gly Lys
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Nle
<220> FEATURE:
<221> NAME/KEY: MOD_RES
<222> LOCATION: (5)
<223> OTHER INFORMATION: Lys(Ac)
<220> FEATURE:
<221> NAME/KEY: MOD_RES
```

```
<222> LOCATION: (10)
<223> OTHER INFORMATION: Lys(MR121)

<400> SEQUENCE: 9

Xaa Pro Ser Asp Lys Thr Ile Gly Gly Lys
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Nle
<220> FEATURE:
<221> NAME/KEY: MOD_RES
<222> LOCATION: (5)
<223> OTHER INFORMATION: Lys(Ac)
<220> FEATURE:
<221> NAME/KEY: MOD_RES
<222> LOCATION: (10)
<223> OTHER INFORMATION: Lys(5-TMR)

<400> SEQUENCE: 10

Xaa Pro Ser Asp Lys Thr Ile Gly Gly Lys
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Nle
<220> FEATURE:
<221> NAME/KEY: MOD_RES
<222> LOCATION: (7)
<223> OTHER INFORMATION: Lys(Ac)
<220> FEATURE:
<221> NAME/KEY: MOD_RES
<222> LOCATION: (12)
<223> OTHER INFORMATION: Lys(MR121)

<400> SEQUENCE: 11

Gly Gln Xaa Pro Ser Asp Lys Thr Ile Gly Gly Lys
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Nle
<220> FEATURE:
<221> NAME/KEY: MOD_RES
<222> LOCATION: (7)
<223> OTHER INFORMATION: Lys(Ac)
<220> FEATURE:
<221> NAME/KEY: MOD_RES
<222> LOCATION: (12)
<223> OTHER INFORMATION: Lys(5-TMR)
```

<400> SEQUENCE: 12

Gly Gln Xaa Pro Ser Asp Lys Thr Ile Gly Gly Lys
 1               5                  10

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(Ac)
<220> FEATURE:
<221> NAME/KEY: MOD_RES
<222> LOCATION: (6)
<223> OTHER INFORMATION: Lys(MR121)

<400> SEQUENCE: 13

Ser Gly Lys Ile Met Lys
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(Ac)
<220> FEATURE:
<221> NAME/KEY: MOD_RES
<222> LOCATION: (6)
<223> OTHER INFORMATION: Lys(5-TMR)

<400> SEQUENCE: 14

Ser Gly Lys Ile Met Lys
 1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Lys(Ac)
<220> FEATURE:
<221> NAME/KEY: MOD_RES
<222> LOCATION: (7)
<223> OTHER INFORMATION: Nle
<220> FEATURE:
<221> NAME/KEY: MOD_RES
<222> LOCATION: (9)
<223> OTHER INFORMATION: Lys(MR121)

<400> SEQUENCE: 15

Thr Ser Ser Gly Lys Ile Xaa Ser Lys
 1               5

<210> SEQ ID NO 16
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Lys(Ac)
<220> FEATURE:
<221> NAME/KEY: MOD_RES
<222> LOCATION: (7)
<223> OTHER INFORMATION: Nle
<220> FEATURE:
<221> NAME/KEY: MOD_RES
<222> LOCATION: (9)
<223> OTHER INFORMATION: Lys(5-TMR)

<400> SEQUENCE: 16

Thr Ser Ser Gly Lys Ile Xaa Ser Lys
 1               5

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Lys(Ac)
<220> FEATURE:
<221> NAME/KEY: MOD_RES
<222> LOCATION: (9)
<223> OTHER INFORMATION: Nle
<220> FEATURE:
<221> NAME/KEY: MOD_RES
<222> LOCATION: (12)
<223> OTHER INFORMATION: Lys(MR121)

<400> SEQUENCE: 17

Pro Ser Thr Ser Ser Gly Lys Ile Xaa Ser Ser Lys
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Lys(Ac)
<220> FEATURE:
<221> NAME/KEY: MOD_RES
<222> LOCATION: (9)
<223> OTHER INFORMATION: Nle
<220> FEATURE:
<221> NAME/KEY: MOD_RES
<222> LOCATION: (12)
<223> OTHER INFORMATION: Lys(5-TMR)

<400> SEQUENCE: 18

Pro Ser Thr Ser Ser Gly Lys Ile Xaa Ser Ser Lys
 1               5                  10

<210> SEQ ID NO 19
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Lys(Ac)
<220> FEATURE:
<221> NAME/KEY: MOD_RES
<222> LOCATION: (9)
<223> OTHER INFORMATION: Lys(MR121)

<400> SEQUENCE: 19

Ser Gly Ser Gly Lys Gly Gly Ser Lys
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Lys(Ac)
<220> FEATURE:
<221> NAME/KEY: MOD_RES
<222> LOCATION: (9)
<223> OTHER INFORMATION: Lys(5-TMR)

<400> SEQUENCE: 20

Ser Gly Ser Gly Lys Gly Gly Ser Lys
 1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Lys(Ac)
<220> FEATURE:
<221> NAME/KEY: MOD_RES
<222> LOCATION: (10)
<223> OTHER INFORMATION: Lys(MR121)

<400> SEQUENCE: 21

Gly Ser Gly Gly Ala Lys Ser His Ser Lys
 1               5                  10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Lys(Ac)
<220> FEATURE:
<221> NAME/KEY: MOD_RES
<222> LOCATION: (10)
<223> OTHER INFORMATION: Lys(5-TMR)

<400> SEQUENCE: 22

Gly Ser Gly Gly Ala Lys Ser His Ser Lys
```

```
<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Lys(Ac)
<220> FEATURE:
<221> NAME/KEY: MOD_RES
<222> LOCATION: (10)
<223> OTHER INFORMATION: Lys(MR121)

<400> SEQUENCE: 23

Gly Ala Ser Ser His Ser Lys Val Leu Lys
  1               5                  10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Lys(Ac)
<220> FEATURE:
<221> NAME/KEY: MOD_RES
<222> LOCATION: (10)
<223> OTHER INFORMATION: Lys(5-TMR)

<400> SEQUENCE: 24

Gly Ala Ser Ser His Ser Lys Val Leu Lys
  1               5                  10

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Lys(Ac)
<220> FEATURE:
<221> NAME/KEY: MOD_RES
<222> LOCATION: (13)
<223> OTHER INFORMATION: Nle

<400> SEQUENCE: 25

Glu Glu Lys Gly Gln Ser Thr Ser Ser His Ser Lys Xaa Ser Thr Glu
  1               5                  10                  15

Gly Lys Trp Glu Glu
             20

<210> SEQ ID NO 26
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (12)
<223> OTHER INFORMATION: Lys(Ac)
<220> FEATURE:
<221> NAME/KEY: MOD_RES
<222> LOCATION: (13)
<223> OTHER INFORMATION: Nle

<400> SEQUENCE: 26

Glu Glu Lys Gly Gln Ser Thr Ser Ser His Ser Lys Xaa Ser Thr Glu
 1               5                  10                  15

Gly Lys Trp Ala Trp Glu Glu
            20

<210> SEQ ID NO 27
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Lys(Ac)
<220> FEATURE:
<221> NAME/KEY: MOD_RES
<222> LOCATION: (13)
<223> OTHER INFORMATION: Nle

<400> SEQUENCE: 27

Glu Glu Lys Gly Gln Ser Thr Ser Ser His Ser Lys Xaa Ser Thr Glu
 1               5                  10                  15

Gly Lys Trp Trp Phe Glu Glu
            20

<210> SEQ ID NO 28
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Lys(Ac)
<220> FEATURE:
<221> NAME/KEY: MOD_RES
<222> LOCATION: (13)
<223> OTHER INFORMATION: Nle

<400> SEQUENCE: 28

Glu Glu Lys Gly Gln Ser Thr Ser Ser His Ser Lys Xaa Ser Thr Glu
 1               5                  10                  15

Gly Lys Trp Trp Trp Glu Glu
            20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Lys(Ac)
<220> FEATURE:
<221> NAME/KEY: MOD_RES
```

```
<222> LOCATION: (13)
<223> OTHER INFORMATION: Nle

<400> SEQUENCE: 29

Glu Glu Lys Gly Gln Ser Thr Ser Ser His Ser Lys Xaa Ser Thr Glu
  1               5                  10                  15

Gly Trp Glu Glu
            20

<210> SEQ ID NO 30
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Lys(Ac)
<220> FEATURE:
<221> NAME/KEY: MOD_RES
<222> LOCATION: (13)
<223> OTHER INFORMATION: Nle

<400> SEQUENCE: 30

Glu Glu Lys Gly Gln Ser Thr Ser Ser His Ser Lys Xaa Ser Thr Glu
  1               5                  10                  15

Gly Trp Ala Trp Glu Glu
            20

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Lys(Ac)
<220> FEATURE:
<221> NAME/KEY: MOD_RES
<222> LOCATION: (13)
<223> OTHER INFORMATION: Nle

<400> SEQUENCE: 31

Glu Glu Lys Gly Gln Ser Thr Ser Ser His Ser Lys Xaa Ser Thr Glu
  1               5                  10                  15

Gly Trp Trp Phe Glu Glu
            20

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Lys(Ac)
<220> FEATURE:
<221> NAME/KEY: MOD_RES
<222> LOCATION: (13)
<223> OTHER INFORMATION: Nle

<400> SEQUENCE: 32
```

```
Glu Glu Lys Gly Gln Ser Thr Ser Ser His Ser Lys Xaa Ser Thr Glu
1               5                   10                  15

Gly Trp Trp Trp Glu Glu
            20
```

<210> SEQ ID NO 33
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Lys(Ac)
<220> FEATURE:
<221> NAME/KEY: MOD_RES
<222> LOCATION: (13)
<223> OTHER INFORMATION: Nle

<400> SEQUENCE: 33

```
Glu Glu Lys Gly Gln Ser Thr Ser Ser His Ser Lys Xaa Ser Thr Glu
1               5                   10                  15

Gly Lys Trp Trp Trp Trp Trp Glu Glu
            20                  25
```

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(biotin)
<220> FEATURE:
<221> NAME/KEY: MOD_RES
<222> LOCATION: (12)
<223> OTHER INFORMATION: Lys(Ac)
<220> FEATURE:
<221> NAME/KEY: MOD_RES
<222> LOCATION: (13)
<223> OTHER INFORMATION: Nle
<220> FEATURE:
<221> NAME/KEY: MOD_RES
<222> LOCATION: (18)
<223> OTHER INFORMATION: Lys(5TMR)

<400> SEQUENCE: 34

```
Glu Glu Lys Gly Gln Ser Thr Ser Ser His Ser Lys Xaa Ser Thr Glu
1               5                   10                  15

Gly Lys Glu Glu
            20
```

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(biotin)
<220> FEATURE:
<221> NAME/KEY: MOD_RES
<222> LOCATION: (13)
<223> OTHER INFORMATION: Nle

```
<220> FEATURE:
<221> NAME/KEY: MOD_RES
<222> LOCATION: (18)
<223> OTHER INFORMATION: Lys(5TMR)

<400> SEQUENCE: 35

Glu Glu Lys Gly Gln Ser Thr Ser Ser His Ser Lys Xaa Ser Thr Glu
 1               5                  10                  15

Gly Lys Glu Glu
            20
```